United States Patent
Stulen et al.

(10) Patent No.: US 10,368,892 B2
(45) Date of Patent: Aug. 6, 2019

(54) FEATURES FOR COUPLING SURGICAL INSTRUMENT SHAFT ASSEMBLY WITH INSTRUMENT BODY

(71) Applicant: Ethicon Endo-Surgery, Inc., Cincinnati, OH (US)

(72) Inventors: Foster B. Stulen, Mason, OH (US); Daniel W. Price, Loveland, OH (US); William E. Clem, Bozeman, MT (US); Cory G. Kimball, Cincinnati, OH (US); Timothy G. Dietz, Wayne, PA (US); Kevin L. Houser, Springboro, OH (US)

(73) Assignee: Ethicon LLC, Guaynabo, PR (US)

( * ) Notice: Subject to any disclaimer, the term of this patent is extended or adjusted under 35 U.S.C. 154(b) by 1298 days.

(21) Appl. No.: 14/087,383

(22) Filed: Nov. 22, 2013

(65) Prior Publication Data

US 2015/0148830 A1 May 28, 2015

(51) Int. Cl.
*A61B 17/32* (2006.01)
*A61B 17/00* (2006.01)
(Continued)

(52) U.S. Cl.
CPC ........... *A61B 17/320068* (2013.01); *A61B 17/320092* (2013.01); *A61B 2017/0046* (2013.01);
(Continued)

(58) Field of Classification Search
CPC .... A61B 17/320068; A61B 17/320092; A61B 2017/0046; A61B 2017/00473; A61B 2017/320096
See application file for complete search history.

(56) References Cited

U.S. PATENT DOCUMENTS 5,322,055 A 6/1994 Davison et al.
5,873,873 A 2/1999 Smith et al.
(Continued)

FOREIGN PATENT DOCUMENTS

EP 1674039 A2 6/2006
EP 1684039 A2 6/2006
(Continued)

OTHER PUBLICATIONS

U.S. Appl. No. 13/657,553, filed Oct. 22, 2012.
(Continued)

*Primary Examiner* — Todd J Scherbel
(74) *Attorney, Agent, or Firm* — Frost Brown Todd LLC

(57) ABSTRACT

A surgical apparatus comprises a body assembly, an ultrasonic transducer, a shaft assembly, a motor, and a locking feature. The ultrasonic transducer is operable to convert electrical power into ultrasonic vibrations. The shaft assembly comprises a waveguide operable to transmit ultrasonic vibrations. The motor is operable to rotate the ultrasonic transducer to thereby selectively couple the ultrasonic transducer with the waveguide. The locking feature is configured to selectively prevent rotation of at least a portion of the shaft assembly relative to the body assembly. The locking feature and the motor may be activated automatically in response to an operator positioning a proximal portion of the shaft assembly in a distal portion of the body assembly. The surgical apparatus may include a feature configured to alert a user when the waveguide has been adequately secured to the ultrasonic transducer.

20 Claims, 40 Drawing Sheets

(51) Int. Cl.
*A61B 17/29* (2006.01)
*A61B 90/00* (2016.01)

(52) U.S. Cl.
CPC .............. *A61B 2017/00477* (2013.01); *A61B 2017/00526* (2013.01); *A61B 2017/2929* (2013.01); *A61B 2017/320078* (2017.08); *A61B 2090/031* (2016.02); *A61B 2090/0812* (2016.02); *Y10T 29/49004* (2015.01)

(56) References Cited

U.S. PATENT DOCUMENTS

| | | |
|---|---|---|
| 5,947,984 A | 9/1999 | Whipple |
| 5,980,510 A | 11/1999 | Tsonton et al. |
| 6,017,354 A | 1/2000 | Culp et al. |
| 6,325,811 B1 | 12/2001 | Messerly |
| 6,773,444 B2 | 8/2004 | Messerly |
| 6,783,524 B2 | 8/2004 | Anderson et al. |
| 8,419,757 B2 | 4/2013 | Smith et al. |
| 8,461,744 B2 | 6/2013 | Wiener et al. |
| 8,591,536 B2 | 11/2013 | Robertson |
| 8,623,027 B2 | 1/2014 | Price et al. |
| 9,050,125 B2 | 6/2015 | Boudreaux et al. |
| 9,427,279 B2 | 8/2016 | Muniz-Medina et al. |
| 2006/0079874 A1 | 4/2006 | Faller et al. |
| 2007/0191713 A1 | 8/2007 | Eichmann et al. |
| 2007/0282333 A1 | 12/2007 | Fortson et al. |
| 2008/0200940 A1 | 8/2008 | Eichmann et al. |
| 2008/0269667 A1 | 10/2008 | Gencarelli |
| 2010/0069940 A1 | 3/2010 | Miller et al. |
| 2011/0087212 A1 | 4/2011 | Aldridge et al. |
| 2012/0112687 A1 | 5/2012 | Houser et al. |
| 2012/0116260 A1 | 5/2012 | Johnson et al. |
| 2012/0116265 A1 | 5/2012 | Houser et al. |
| 2012/0116396 A1* | 5/2012 | Price ................. A61B 17/00234 606/45 |
| 2013/0090577 A1* | 4/2013 | Boudreaux .... A61B 17/320092 601/2 |
| 2013/0324991 A1* | 12/2013 | Clem ............. A61B 17/320068 606/33 |
| 2013/0324998 A1 | 12/2013 | Kimball et al. |
| 2014/0005701 A1 | 1/2014 | Olson et al. |
| 2014/0263565 A1* | 9/2014 | Lytle, IV ............. A61B 17/068 227/180.1 |

FOREIGN PATENT DOCUMENTS

| | | |
|---|---|---|
| JP | 2002-159509 A | 6/2002 |
| JP | 2012-519023 A | 8/2012 |
| JP | 2012-223582 A | 11/2012 |
| JP | 2013-502998 A | 1/2013 |

OTHER PUBLICATIONS

U.S. Appl. No. 14/028,717, filed Sep. 17, 2013
U.S. Appl. No. 61/410,603, filed Nov. 5, 2010.
International Search Report and Written Opinion dated Jun. 26, 2015 re Application No. PCT/US2014/065623.
Chinese Office Action, Notification of the First Office Action, and Search Report dated Jan. 23, 2018 for Application No. CN 201480063584.5, 4 pgs.
European Communication, Intention to Grant, dated Dec. 1, 2017 for Application No. EP 14805456.2, 91 pgs.
Japanese Office Action, Notification of Reason for Refusal, and Search Report by Registered Searching Authority dated Oct. 16, 2018 for Application No. JP 2016-533142, 37 pgs.

* cited by examiner

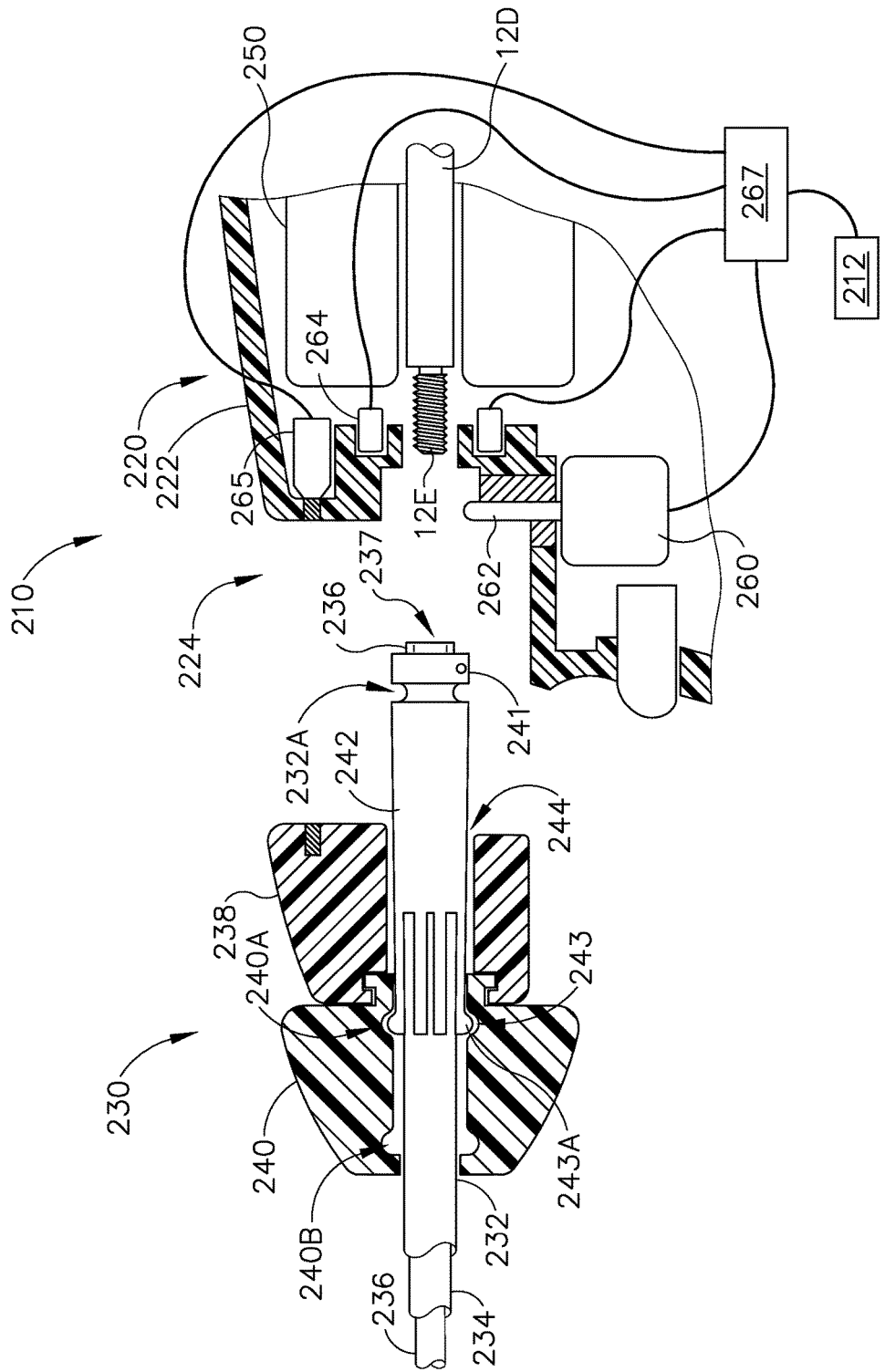

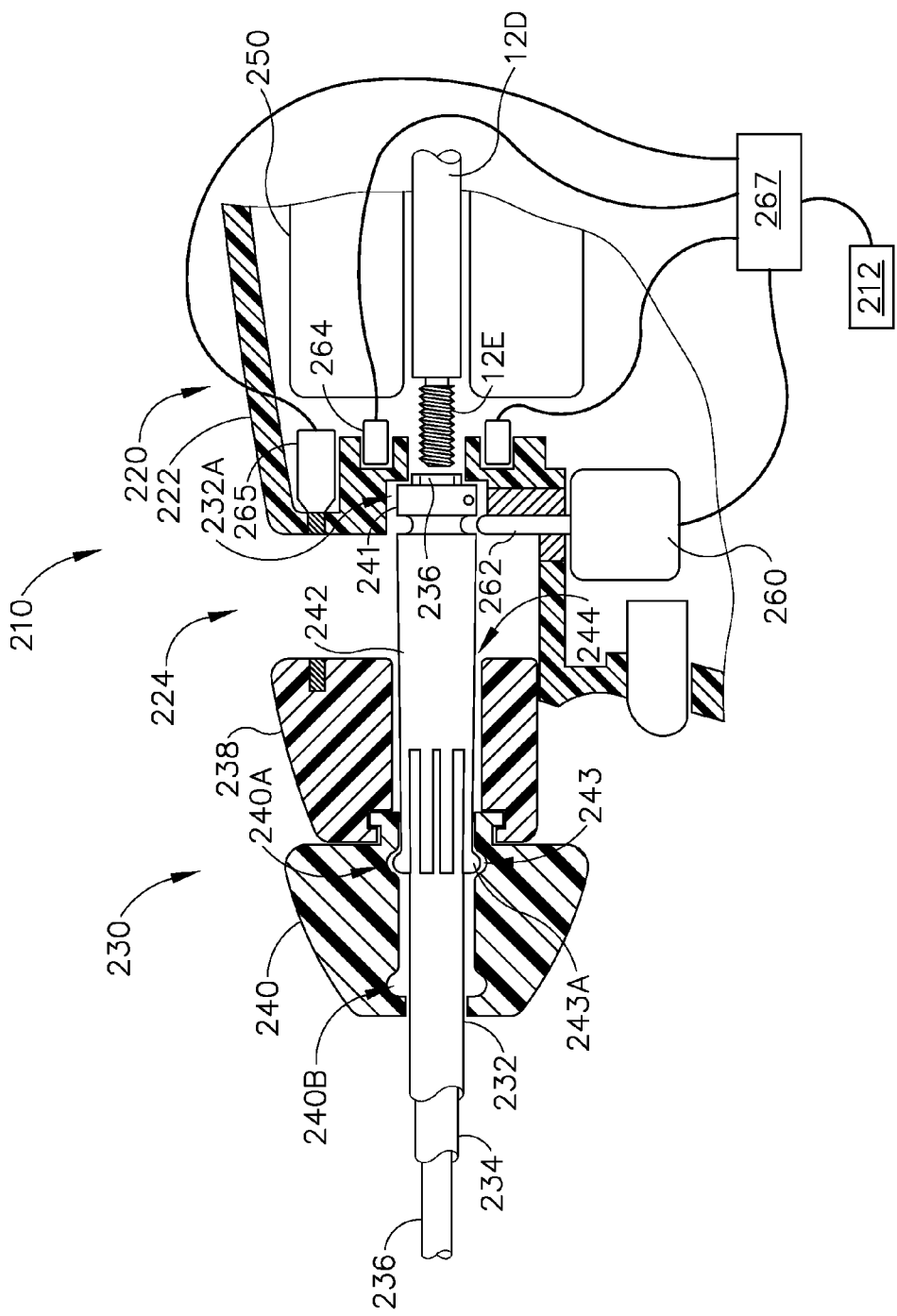

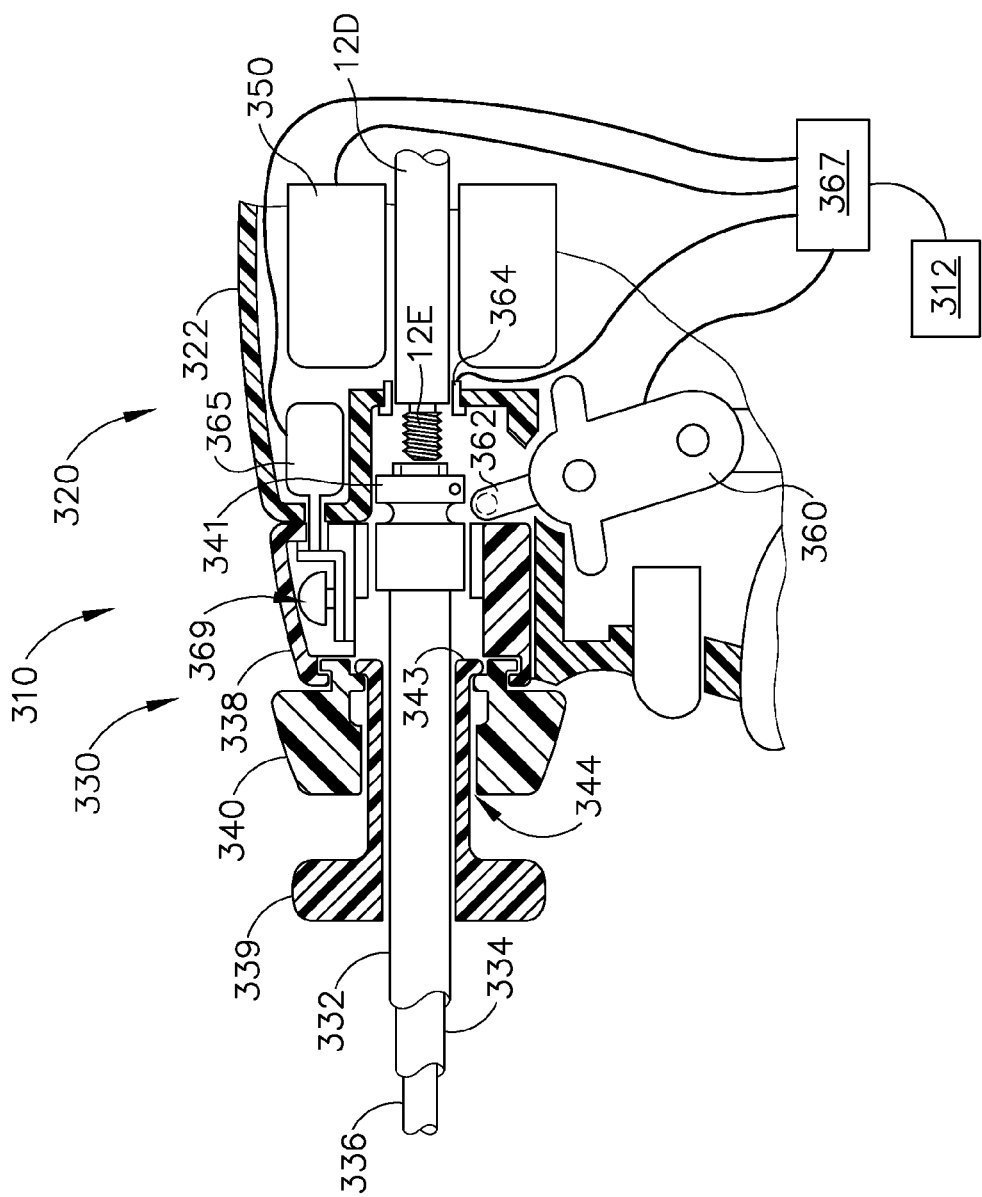

FEATURES FOR COUPLING SURGICAL INSTRUMENT SHAFT ASSEMBLY WITH INSTRUMENT BODY

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2009/0105750, entitled "Ergonomic Surgical Instruments," published Apr. 23, 2009, issued as U.S. Pat. No. 8,623,027 on Jan. 7, 2014, the disclosure of which is incorporated by reference herein; U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein; and U.S. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013, the disclosure of which is incorporated by reference herein; and U.S. Pub. No. 2012/0029546, entitled "Ultrasonic Surgical Instrument Blades," published Feb. 2, 2012, issued as U.S. Pat. No. 8,591,536 on Nov. 26, 2013, the disclosure of which is incorporated by reference herein.

Some of ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,058 on Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. patent application Ser. No. 13/538,588, filed Jun. 29, 2012, issued as U.S. Pat. No. 9,393,037 on Jul. 19, 2016, entitled "Surgical Instruments with Articulating Shafts," the disclosure of which is incorporated by reference herein; and U.S. patent application Ser. No. 13/657,553, filed Oct. 22, 2012, issued as U.S. Pat. No. 9,095,367 on Aug. 4, 2015, entitled "Flexible Harmonic Waveguides/Blades for Surgical Instruments," the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 9A depicts a partial cross-sectional view of the instrument of FIG. 8 with the shaft assembly in a first longitudinal position;

FIG. 9B depicts a partial cross-sectional view of the instrument of FIG. 8 with the shaft assembly moved into a second longitudinal position;

FIG. 13B depicts a partial cross-sectional view of the instrument of FIG. 12 with the shaft assembly moved into a second longitudinal position;

Figure 1:
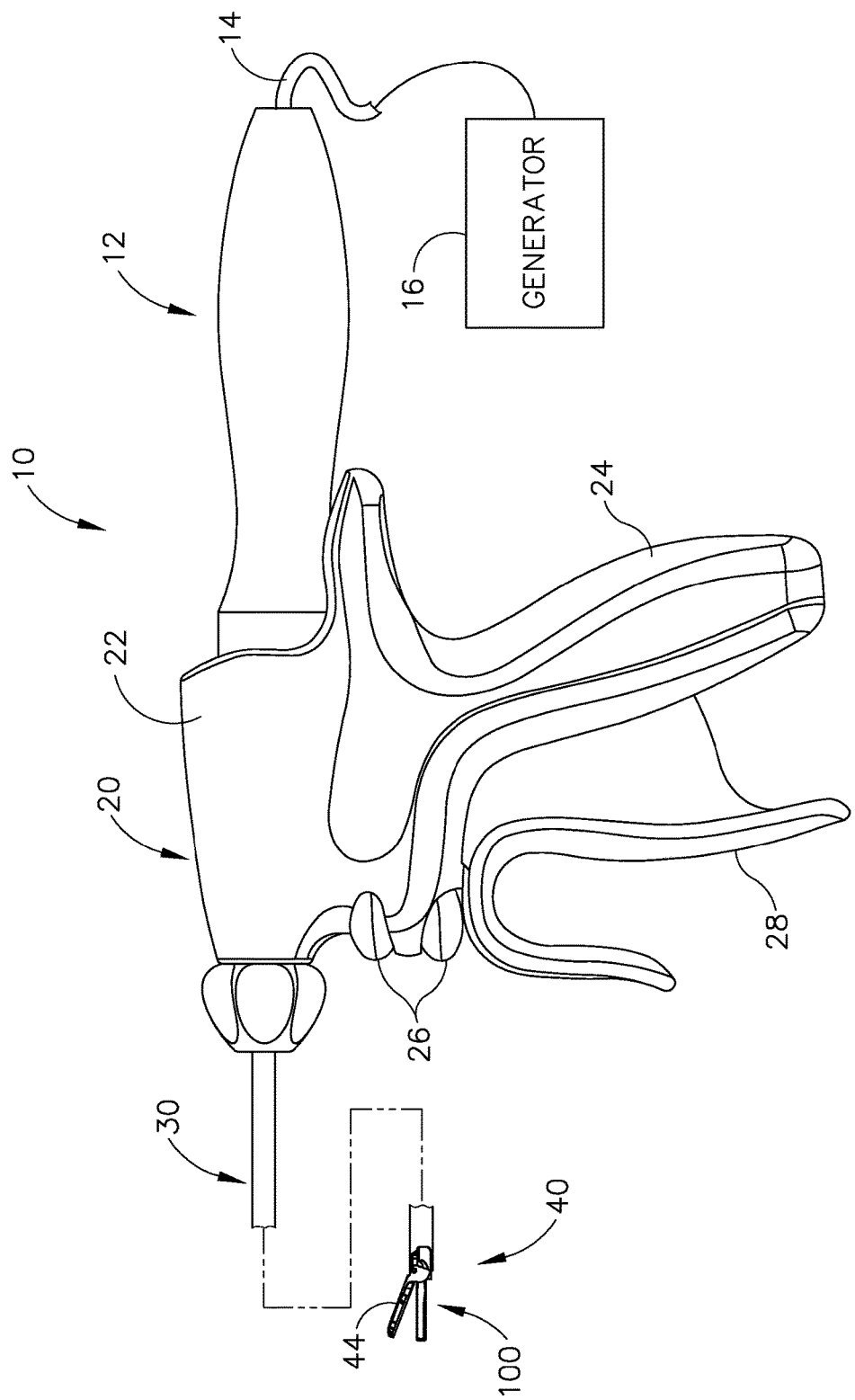
FIG. 1 depicts a side elevational view of an exemplary surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. Exemplary Ultrasonic Surgical Instrument

FIG. 1 illustrates an exemplary ultrasonic surgical instrument (10). At least part of instrument (10) may be constructed and operable in accordance with at least some of the teachings of U.S. Pat. No. 5,322,055; U.S. Pat. No. 5,873,873; U.S. Pat. No. 5,980,510; U.S. Pat. No. 6,325,811; U.S. Pat. No. 6,773,444; U.S. Pat. No. 6,783,524; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2009/0105750, issued as U.S. Pat. No. 8,623,027 on Jan. 7, 2014; U.S. Pub. No. 2010/0069940, issued as U.S. Pat. No. 9,023,071 on May 5, 2015; U.S. Pub. No. 2011/0015660, issued as U.S. Pat. No. 8,461,744 on Jun. 11, 2013; U.S. Pub. No. 2012/0112687, issued as U.S. Pat. No. 9,381,058 on Jul. 5, 2016; U.S. Pub. No. 2012/0116265, now abandoned; U.S. patent application Ser. No. 13/538,588, issued as U.S. Pat. No. 9,393,037 on Jul. 19, 2016; U.S. patent application Ser. No. 13/657,553, issued as U.S. Pat. No. 9,095,367 on Aug. 4, 2015; U.S. Pat. App. No. 61/410,603; and/or U.S. patent application Ser. No. 14/028,717, issued as U.S. Pat. No. 10,172,636 on Jan. 8, 2019. The disclosures of each of the foregoing patents, publications, and applications are incorporated by reference herein. As described therein and as will be described in greater detail below, instrument (10) is operable to cut tissue and seal or weld tissue (e.g., a blood vessel, etc.) substantially simultaneously. It should also be understood that instrument (10) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (10) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instrument (10), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Figure 2:
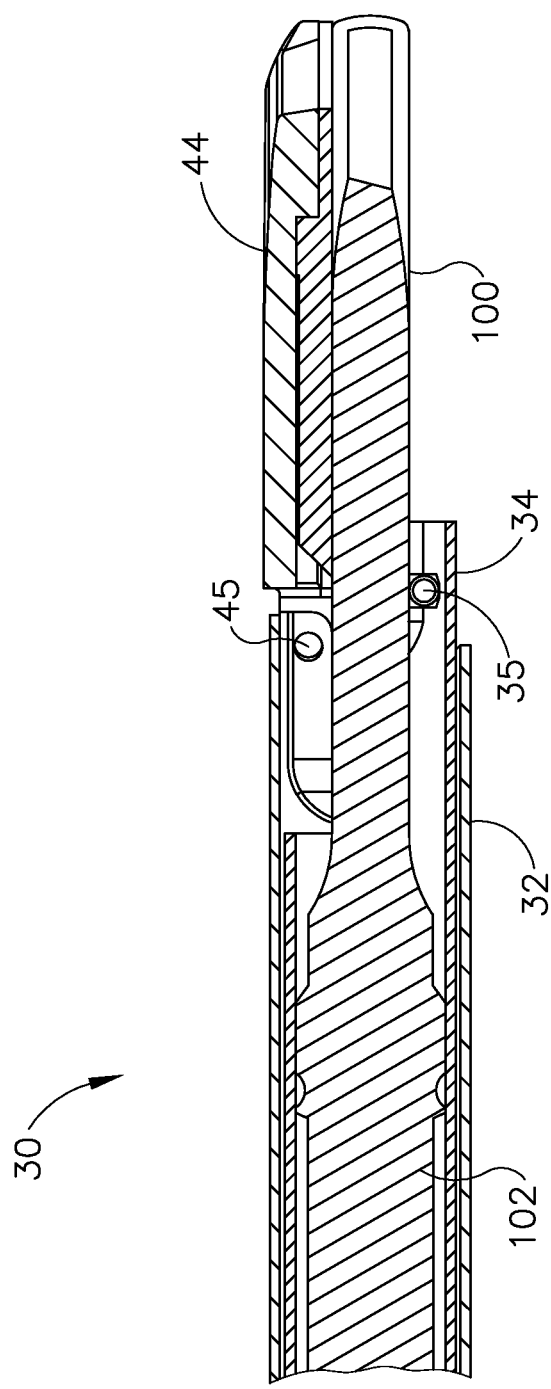
FIG. 2 depicts a cross-sectional view of an end effector of the instrument of FIG. 1 in a closed position.
Figure 3:
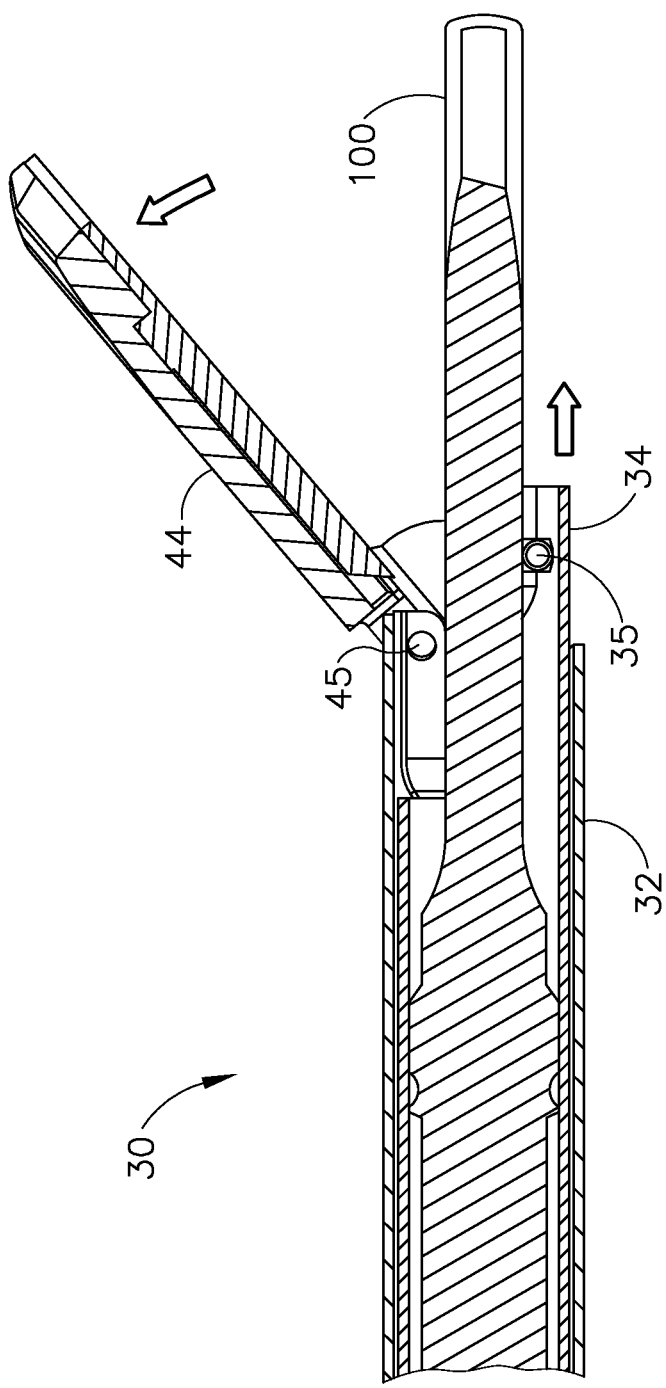
FIG. 3 depicts a cross-sectional view of an end effector of the instrument of FIG. 1 in an open position.
Figure 4:
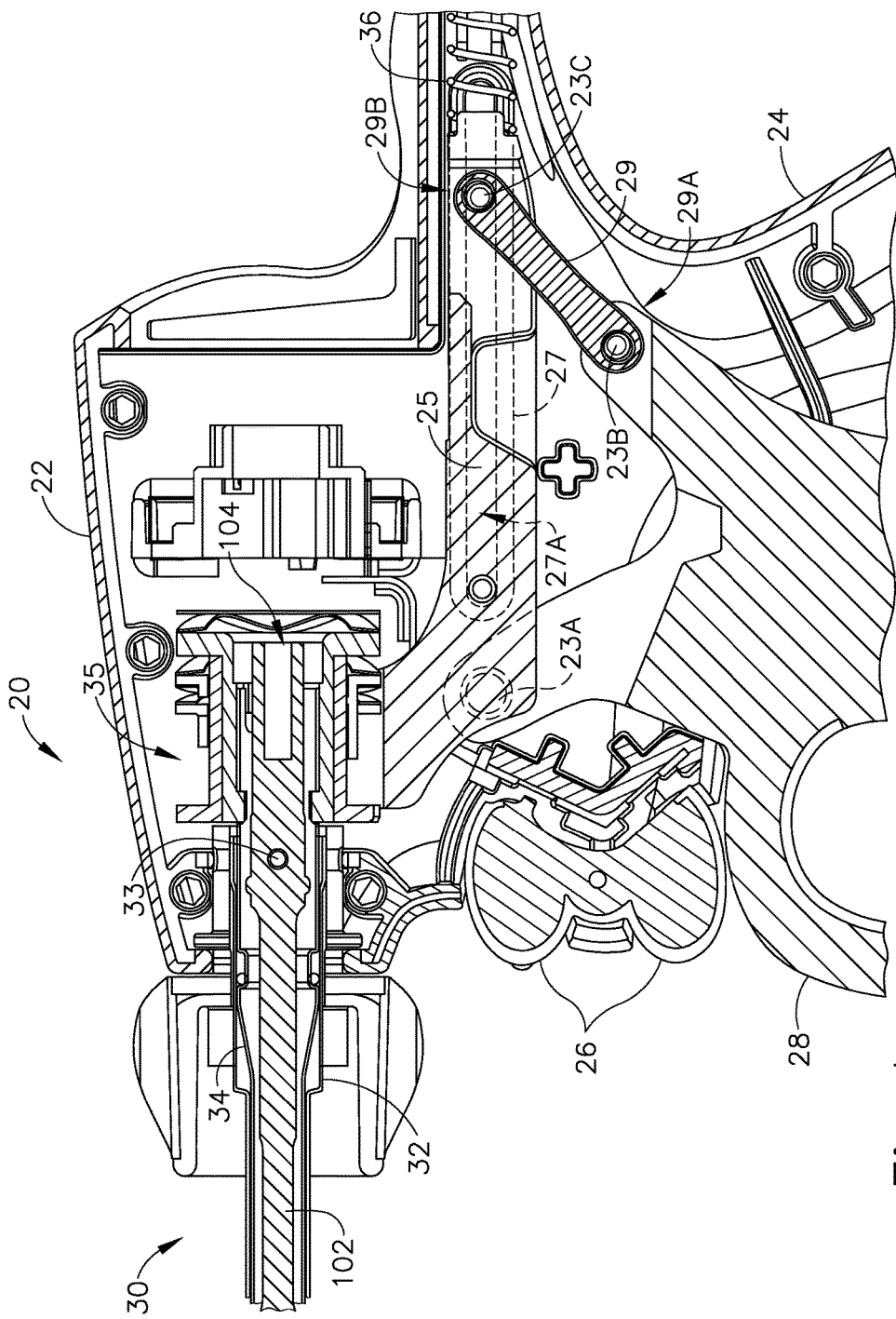
FIG. 4 depicts a cross-sectional view of a handle assembly of the instrument of FIG. 1.

Instrument (10) of the present example comprises a handle assembly (20), a shaft assembly (30), and an end effector (40). As shown in FIGS. 2-4, shaft assembly (30) comprises an outer sheath (32), an inner tube (34) slidably disposed within outer sheath (32), and a waveguide (102) disposed within inner tube (34). As will be discussed in more detail below, longitudinal translation of inner tube (34) causes actuation of clamp arm (44) at end effector (40). Handle assembly (20) comprises a body (22) including a pistol grip (24) and a pair of buttons (26). Handle assembly (20) also includes a trigger (28) that is pivotable toward and away from pistol grip (24). It should be understood, however, that various other suitable configurations may be used, including but not limited to a scissor grip configuration. As shown in FIG. 4, trigger (28) is pivotably coupled to handle assembly (20) via a pin (23A) such that trigger (28) rotates about an axis located below shaft assembly (30).

Trigger (28) is coupled with a yoke (25) via a linkage (29) such that rotation of trigger (28) about pin (23A) causes longitudinal translation of yoke (25). A first end (29A) of linkage (29) is rotatably coupled with a proximal portion of trigger (28) via a pin (23B). A second end (29B) of linkage (29) is rotatably coupled with a proximal portion of yoke (25) via a pin (23C). A pair of elongate oval-shaped projections (27) extend inwardly from interior surfaces of body (22). An interior surface of each oval-shaped projection (27) defines an elongate oval-shaped slot (27A). Pin (23C) passes completely through the proximal portion of yoke (25) and second end (29B) of linkage (29) such that ends of pin (23C) extend from opposite sides of yoke (25). These ends of pin (23C) are slidably and rotatably disposed within oval-shaped slots (27A). A pin (23D) passes completely through a distal portion of yoke (25) such that ends of pin (23D) extend from opposite sides of yoke (25). These ends of pin (23D) are slidably and rotatably disposed within oval-shaped slots (27A). It should therefore be understood that yoke (25) is longitudinally translatable via pins (23C, 23D) within oval-shaped slots (27A) between a proximal longitudinal position and a distal longitudinal position. Furthermore, because the proximal portion of trigger (28) is coupled with yoke (25) via linkage (29), it should be understood that pivoting of trigger (28) toward pistol grip (24) will cause proximal longitudinal translation of yoke (25) within oval-shaped slots (27A); and that pivoting of trigger (28) away from pistol grip (24) will cause distal longitudinal translation of yoke (25) within oval-shaped slots (27A).

A distal portion of yoke (25) is coupled with inner tube (34) of shaft assembly (30) via a coupling assembly (35). As discussed above, inner tube (34) is longitudinally translatable within outer sheath (32). It should therefore be understood that inner tube (34) is configured to longitudinally translate concurrently with yoke (25). Furthermore, because pivoting of trigger (28) toward pistol grip (24) causes proximal longitudinal translation of yoke (25), it should be understood that pivoting of trigger (28) toward pistol grip (24) will cause proximal longitudinal translation of inner tube (34) relative to outer sheath (32) and handle assembly (20). Finally, because pivoting of trigger (28) away from pistol grip (24) causes distal longitudinal translation of yoke (25), it should be understood that and that pivoting of trigger (28) away from pistol grip (24) will cause distal longitudinal translation of inner tube (34) relative to outer sheath (32) and handle assembly (20). As shown in FIG. 4, a spring (36) is positioned within a proximal end of body (22) of handle assembly (20). Spring (36) bears against a portion of body (22) and a proximal end of yoke (25) to thereby bias yoke (25) toward the distal position. Biasing of yoke (25) toward the distal position causes inner tube (34) to be biased distally and further causes trigger (28) to be biased away from pistol grip (24).

As shown in FIGS. 2 and 3, end effector (40) includes an ultrasonic blade (100) and a pivoting clamp arm (44). Clamp arm (44) is pivotably coupled with a distal end of outer sheath (32) of shaft assembly (30) above ultrasonic blade (100) via a pin (45). As best seen in FIG. 3, a distal end of inner tube (34) is rotatably coupled with a proximal end of clamp arm (44) below ultrasonic blade (100) via a pin (33) such that longitudinal translation of inner tube (34) relative to outer sheath (32) and handle assembly (20) causes rotation of clamp arm (44) about pin (45) toward and away from ultrasonic blade (100) to thereby clamp tissue between clamp arm (44) and ultrasonic blade (100) to cut and/or seal the tissue. In particular, proximal longitudinal translation of inner tube (34) relative to outer sheath (32) and handle assembly (20) causes clamp arm (44) to move toward ultrasonic blade (100); and distal longitudinal translation of inner tube (34) relative to outer sheath (32) and handle assembly (20) causes clamp arm (44) to move away from ultrasonic blade (100). It should therefore be understood that pivoting of trigger (28) toward pistol grip (24) will cause clamp arm (44) to move toward ultrasonic blade (100); and that pivoting of trigger (28) away from pistol grip (24) will cause clamp arm (44) to move away from ultrasonic blade (100).

An ultrasonic transducer assembly (12) extends proximally from body (22) of handle assembly (20). As will be discussed in more detail below, transducer assembly (12) receives electrical power from generator (16) and converts that power into ultrasonic vibrations through piezoelectric principles. Generator (16) may include a power source and control module that is configured to provide a power profile to transducer assembly (12) that is particularly suited for the generation of ultrasonic vibrations through transducer assembly (12). By way of example only, generator (16) may comprise a GEN 300 sold by Ethicon Endo-Surgery, Inc. of Cincinnati, Ohio. In addition or in the alternative, generator (16) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. It should also be understood that at least some of the functionality of generator (16) may be integrated into handle assembly (20), and that handle assembly (20) may even include a battery or other on-board power source such that cable (14) is omitted. Still other suitable forms that generator (16) may take, as well as various features and operabilities that generator (16) may provide, will be apparent to those of ordinary skill in the art in view of the teachings herein.

Figure 5:
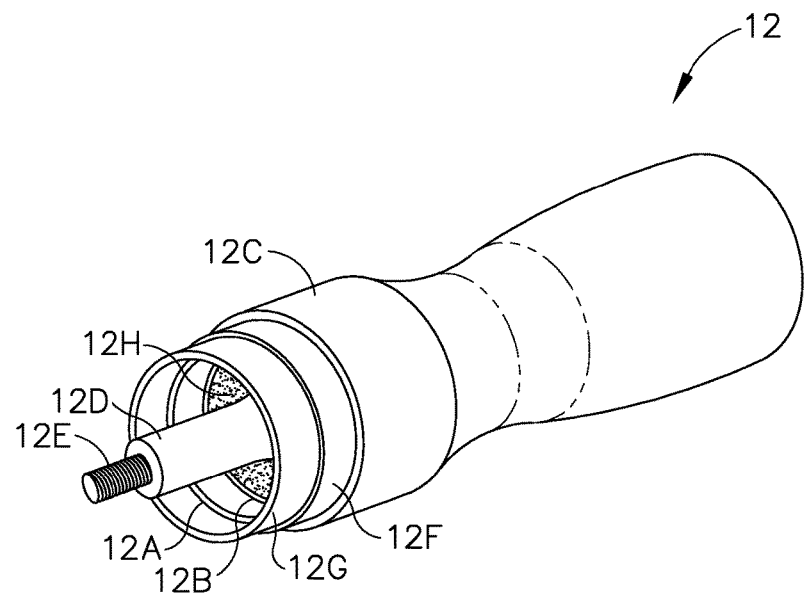
FIG. 5 depicts a perspective view of an exemplary transducer assembly of the instrument of FIG. 1.

As shown in FIG. 1, transducer assembly (12) of the present example is a tubular component that is coupled to generator (16) via cable (14), though it should be understood that transducer assembly (12) may be a cordless transducer. In FIG. 5, transducer assembly (12) is shown in a housing (12C). Focusing on the distal end of transducer assembly (12), transducer assembly (12) includes a first conductive ring (12A) and a second conductive ring (12B) which are disposed within housing (12C) of transducer assembly (12). In one configuration, first conductive ring (12A) comprises a ring member that is disposed between housing (12C) and a horn (12D) extending distally from housing (12C). As will be discussed in more detail below, horn (12D) comprises a threaded stud (12E) extending distally therefrom such that horn (12D) is coupleable to a threaded bore (104) formed in a proximal end of waveguide (102). First conductive ring (12A) is formed adjacent to, or as part of a flange (12F) within a transducer cavity (12G) such that first conductive ring (12A) is electrically isolated from second conductive ring (12B) and other conductive components of transducer assembly (12). First conductive ring (12A) is located on a non-conductive platform extending distally from housing (12C). First conductive ring (12A) is electrically coupled to cable (14), shown in FIG. 1, by one or more electrical wires or conductive etchings (not shown) within housing (12C).

Second conductive ring (12B) of transducer assembly (12) similarly comprises a ring member that is disposed between housing (12C) and horn (12D). Second conductive ring (12B) is disposed between first conductive ring (12A) and horn (12D). As is shown in FIG. 5, first and second conductive rings (12A, 12B) are concentric members that are longitudinally offset from each other, with conductive ring (12A) also being positioned at a greater radial distance from the central axis shared by conductive rings (12A, 12B). Second conductive ring (12B) is likewise electrically isolated from first conductive ring (12A) and other conductive components of transducer assembly (12). Similar to first conductive ring (12A), second conductive ring (12B) extends from the non-conductive platform. One or more washer-shaped spacers (12H) may be disposed between first and second conductive rings (12A, 12B) or between the rings (12A, 12B) and other members of transducer assembly (12). Second conductive ring (12B) is also electrically coupled to cable (14), shown in FIG. 1, by one or more electrical wires or conductive etchings (not shown) within housing (12C). One merely exemplary suitable ultrasonic transducer assembly (12) is Model No. HP054, sold by Ethicon Endo-Surgery, Inc. of Cincinnati, Ohio.

As previously discussed, the distal end of transducer assembly (12) threadably couples with a threaded bore (104) formed in the proximal end of waveguide (120) via threaded stud (12E) of horn (12D). The distal end of transducer assembly (12) also interfaces with one or more electrical connections (not shown) via first and second conductive rings (12A, 12B) to electrically couple transducer assembly (12) to buttons (26) to provide a user with finger-activated controls for activating transducer assembly (12) while using surgical instrument (10). Still other configurations for transducer assembly (12) will be apparent to one of ordinary skill in the art in view of the teachings herein. For instance, first and second conductive rings (12A, 12B) may be omitted from the distal end of transducer assembly (12) and the electrical coupling of transducer assembly (12) to buttons (26) may be accomplished by alternative methods, such as conductors at the proximal end of transducer assembly (12), conductors located along the side of housing (12C) of transducer assembly (12), directly from cable (14), and/or any other structures and configurations as will be apparent to one of ordinary skill in the art in view of the teachings herein.

Figure 6:
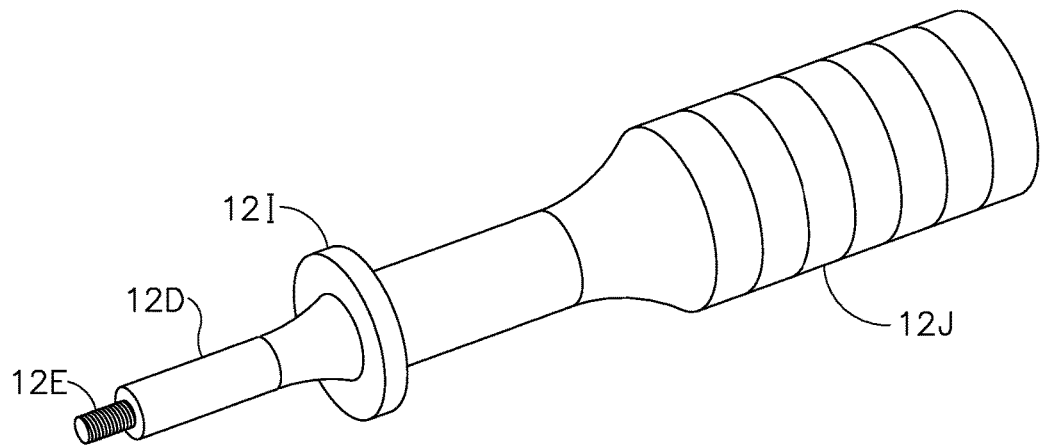
FIG. 6 depicts a perspective view of the transducer of FIG. 5 with a transducer housing removed.

FIG. 6 depicts transducer assembly (12) with housing (12C) removed. Mounting flange (12I) near the distal end of transducer assembly (12) and piezoelectric stack (12J) at the proximal end of transducer assembly (12) can be viewed with housing (12C) removed. When transducer assembly (12) of the present example is activated via a button (26), an electric field is created in piezoelectric stack (12J), causing piezoelectric stack (12J) and horn (12D) to oscillate within and relative to housing (12C). Mounting flange (12I) is used to couple horn (12D) to housing (12C), to thereby support piezoelectric stack (12J) in housing (12C). Mounting flange (12I) is located at a node associated with resonant ultrasonic vibrations communicated from piezoelectric stack (12J) to horn (12D). Transducer assembly (12) is operable to create mechanical energy, or vibrations, at an ultrasonic frequency (such as 55.5 kHz). If transducer assembly (12) is coupled to waveguide (102) via horn (12D), then these mechanical oscillations are transmitted through waveguide (102) to ultrasonic blade (100) of end effector (40). In the present example, ultrasonic blade (100), being coupled to waveguide (102), oscillates at the ultrasonic frequency. Thus, when tissue is secured between ultrasonic blade (100) and clamp arm (44), the ultrasonic oscillation of ultrasonic blade (100) may sever and/or seal the tissue. An electrical current may also be provided through one or both of ultrasonic blade (100) and clamp arm (44) to cauterize the tissue. For instance, monopolar or bipolar RF energy may be provided through one or both of ultrasonic blade (100) and clamp arm (44). While some configurations for transducer assembly (12) have been described, still other suitable configurations for transducer assembly (12) will be apparent to one of ordinary skill in the art in view of the teachings herein.

Figure 7:
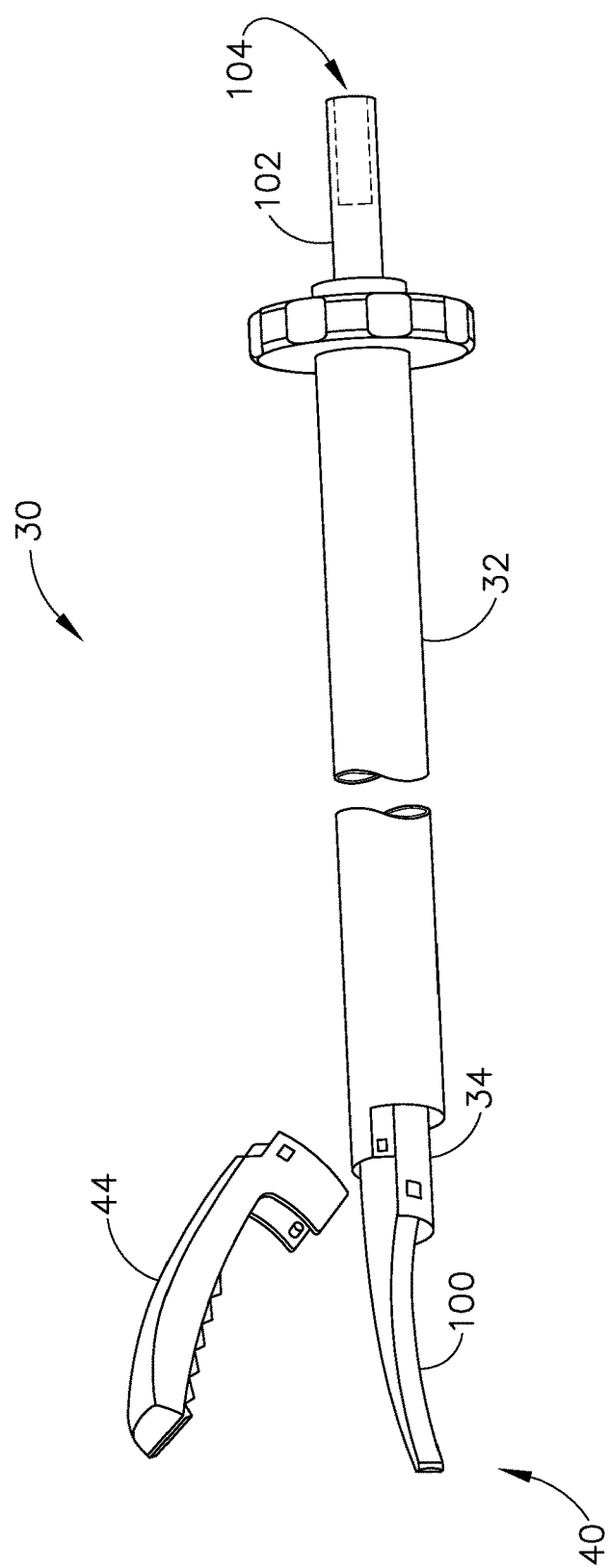
FIG. 7 depicts a perspective view of an exemplary transmission assembly of the instrument of FIG. 1.

FIG. 7 shows shaft assembly (30) and end effector (40). Ultrasonic vibrations that are generated by transducer assembly (12) are communicated along an acoustic waveguide (102), which extends through shaft assembly (30) to reach ultrasonic blade (100). Waveguide (102) is secured within shaft assembly (30) via a pin (33), which passes through waveguide (102) and shaft assembly (30). Pin (33) is located at a position along the length of waveguide (102) corresponding to a node associated with resonant ultrasonic vibrations communicated through waveguide (102). As noted above, when ultrasonic blade (100) is in an activated state (i.e., vibrating ultrasonically), ultrasonic blade (100) is operable to effectively cut through and seal tissue, particularly when the tissue is being clamped between clamp arm (44) and ultrasonic blade (100). It should be understood that waveguide (102) may be configured to amplify mechanical vibrations transmitted through waveguide (102). Furthermore, waveguide (102) may include features operable to control the gain of the longitudinal vibrations along waveguide (102) and/or features to tune waveguide (102) to the resonant frequency of the system.

In the present example, the distal end of ultrasonic blade (100) is located at a position corresponding to an anti-node associated with resonant ultrasonic vibrations communicated through waveguide (102), in order to tune the acoustic assembly to a preferred resonant frequency $f_o$ when the acoustic assembly is not loaded by tissue. When transducer assembly (12) is energized, the distal end of ultrasonic blade (100) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (12) of the present example is activated, these mechanical oscillations are transmitted through the waveguide to reach ultrasonic blade (102), thereby providing oscillation of ultrasonic blade (102) at the resonant ultrasonic frequency. Thus, when tissue is secured between ultrasonic blade (102) and clamp arm (54), the ultrasonic oscillation of ultrasonic blade (102) may simultaneously sever the tissue and denature the proteins in adjacent tissue cells, thereby providing a coagulative effect with relatively little thermal spread. In some versions, an electrical current may also be provided through ultrasonic blade (102) and clamp arm (44) to also cauterize the tissue. While some configurations for an acoustic transmission assembly and transducer assembly (12) have been described, still other suitable configurations for an acoustic transmission assembly and transducer assembly (12) will be apparent to one or ordinary skill in the art in view of the teachings herein. Similarly, other suitable configurations for end effector (40) will be apparent to those of ordinary skill in the art in view of the teachings herein.

An operator may activate buttons (26) to selectively activate transducer assembly (12) to activate ultrasonic blade (100). In the present example, two buttons (26) are provided—one for activating ultrasonic blade (100) at a low power and another for activating ultrasonic blade (100) at a high power. However, it should be understood that any other suitable number of buttons and/or otherwise selectable power levels may be provided. For instance, a foot pedal may be provided to selectively activate transducer assembly (12). Buttons (26) of the present example are positioned such that an operator may readily fully operate instrument (10) with a single hand. For instance, the operator may position their thumb about pistol grip (24), position their middle, ring, and/or little finger about trigger (28), and manipulate buttons (26) using their index finger. Of course, any other suitable techniques may be used to grip and operate instrument (10); and buttons (26) may be located at any other suitable positions.

The foregoing components and operabilities of instrument (10) are merely illustrative. Instrument (10) may be configured in numerous other ways as will be apparent to those of ordinary skill in the art in view of the teachings herein. By way of example only, at least part of instrument (10) may be constructed and/or operable in accordance with at least some of the teachings of any of the following, the disclosures of which are all incorporated by reference herein: U.S. Pat. No. 5,322,055; U.S. Pat. No. 5,873,873; U.S. Pat. No. 5,980,510; U.S. Pat. No. 6,325,811; U.S. Pat. No. 6,783,524; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2010/0069940, issued as U.S. Pat. No. 9,023,071 on May 5, 2015; U.S. Pub. No. 2011/0015660, issued as U.S. Pat. No. 8,461,744 on Jun. 11, 2013; U.S. Pub. No. 2012/0112687, issued as U.S. Pat. No. 9,381,058 on Jul. 5, 2016; U.S. Pub. No. 2012/0116265, now abandoned; U.S. patent application Ser. No. 13/538,588, issued as U.S. Pat. No. 9,393,037 on Jul. 19, 2016; and/or U.S. patent application Ser. No. 13/657,553, issued as U.S. Pat. No. 9,095,367 on Aug. 4, 2015. Additional merely illustrative variations for instrument (10) will be described in greater detail below. It should be understood that the below described variations may be readily applied to instrument (10) described above and any of the instruments referred to in any of the references that are cited herein, among others.

II. Exemplary Motorized Acoustic Assembly Attachment Apparatus

Some versions of instrument (10) provide selective coupling of waveguide (102) with transducer assembly (12) via manual rotation of shaft assembly (30) relative to transducer assembly (12), which may require the operator to hold both transducer assembly (12) and handle assembly (20) stationary while rotating shaft assembly (30). In such versions of instrument (10), an operator may be required to manually apply a proper amount of torque to shaft assembly (30) to ensure appropriate connectivity of waveguide (102) and transducer assembly (12). It may therefore be desirable to provide an assembly that automates the coupling of waveguide (102) with transducer assembly (12). For instance, one feature may selectively fix shaft assembly (30) relative to handle assembly (20) while a motor rotates transducer assembly (12) to thereby threadably couple waveguide (102) with transducer assembly (12). Various illustrative examples of an instrument that includes such features will be described in greater detail below, while other examples will be apparent to those of ordinary skill in the art in view of the teachings herein. It should be understood that the below examples may be viewed as variations of instrument (10), such that various teachings below may be readily combined with various teachings above as will be apparent to those of ordinary skill in the art.

It should also be understood that, in versions of instrument (10) providing motorized coupling of transducer assembly (12) with waveguide (102) such as the examples described below, the motor may be configured to apply the proper amount of torque to transducer assembly (12) to ensure appropriate connectivity of waveguide (102) and transducer assembly (12), then stop rotating to avoid applying too much torque. For instance, instrument (10) may be configured to sense back electromotive force ("back EMF") of the motor to determine torque and deactivate the motor once the back EMF indicates that a desired torque value has been achieved. In addition or in the alternative, instrument (10) may use an encoder or other type of position sensor to stop the motor after achieving a predetermined amount of angular travel associated with a desired torque value. Other suitable ways in which a motor may be automatically stopped upon achieving a desired level of torque in the coupling of waveguide (102) with transducer assembly (12) will be apparent to those of ordinary skill in the art in view of the teachings herein.

A. First Exemplary Motorized Acoustic Assembly Attachment Apparatus

Figure 8:
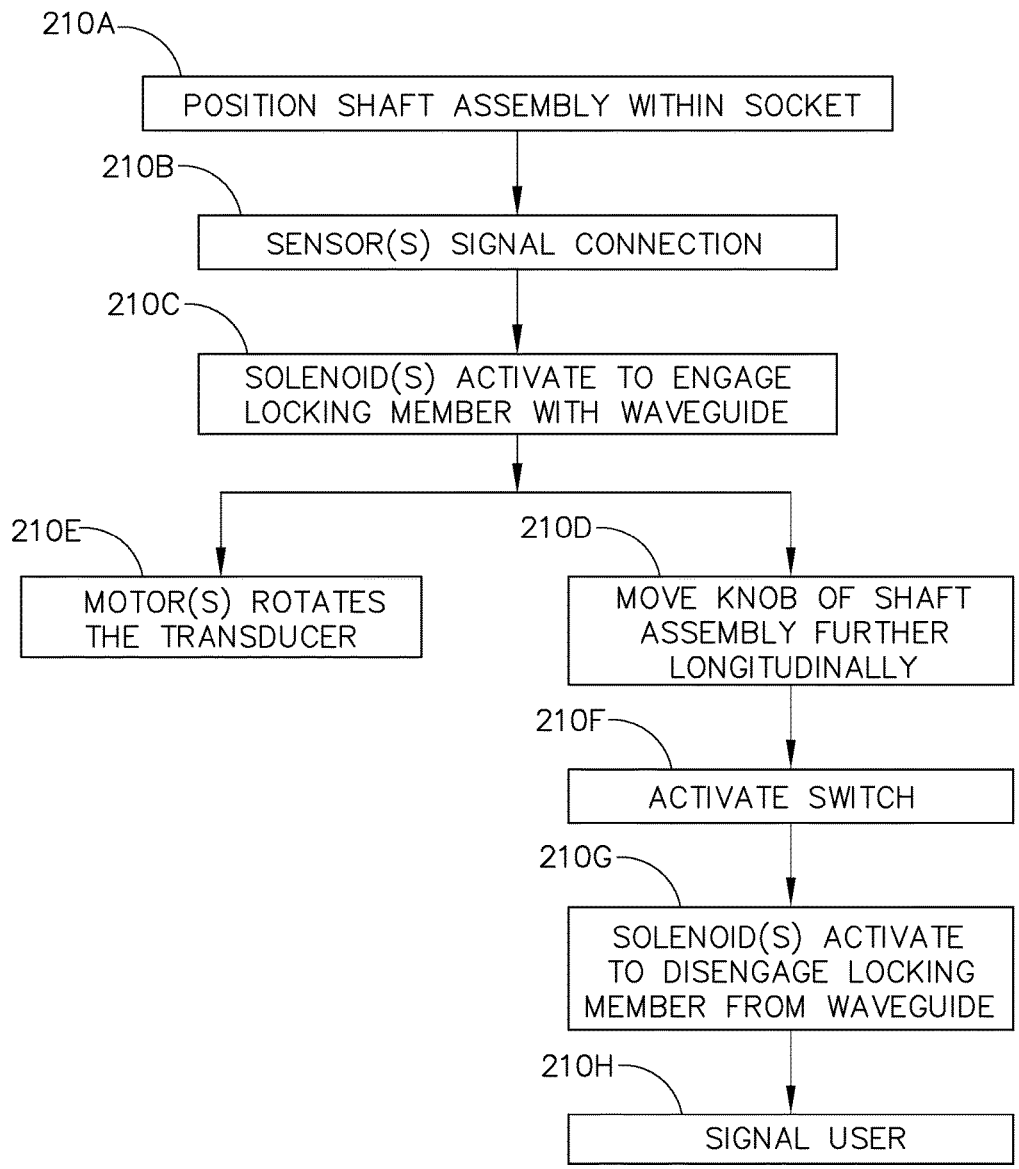
FIG. 8 depicts a flowchart showing steps of attaching an exemplary shaft assembly to a handle assembly of an exemplary variation of the instrument of FIG. 1.
Figure 9C:
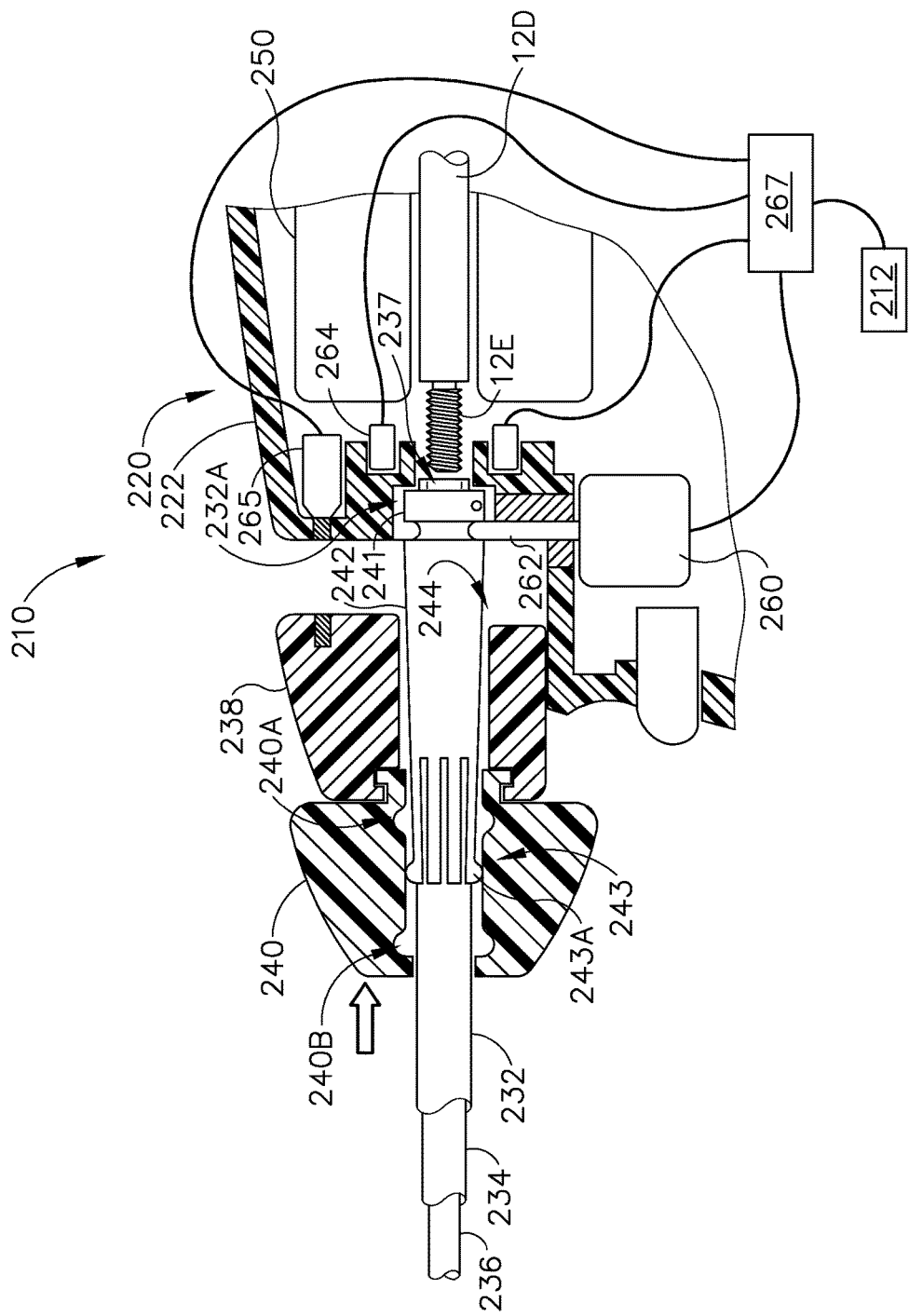
FIG. 9C depicts a partial cross-sectional view of the instrument of FIG. 8 with a locking member engaging the shaft assembly.
Figure 9D:
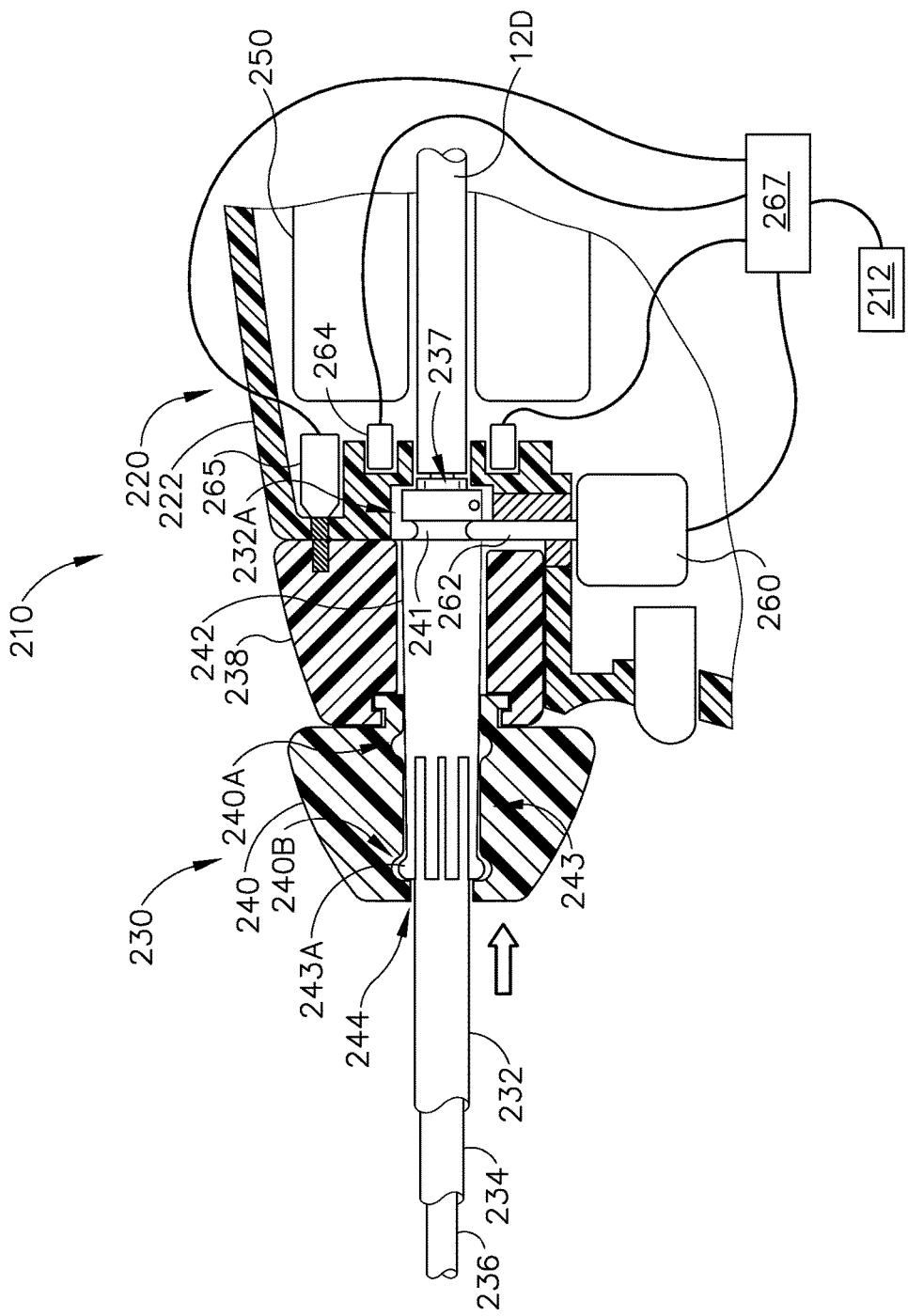
FIG. 9D depicts a partial cross-sectional view of the instrument of FIG. 8 with a knob of the shaft assembly moved into a third longitudinal position.

FIGS. 9A-9E and 11A-11E show an example of an instrument (210) having a motor (250) that mechanically rotates transducer assembly (12) to thereby threadably couple a waveguide (236) with transducer assembly (12). FIG. 8 shows an exemplary process for attaching a shaft assembly (230) to a handle assembly (220) and waveguide (236) to transducer assembly (12). FIG. 10 shows an exemplary process for removing shaft assembly (230) from handle assembly (220) and waveguide (236) from transducer assembly (12). Instrument (210) of the present example is configured to operate substantially similar to instrument (10) discussed above except for the differences discussed below. In particular, instrument (210) is configured to clamp tissue at a surgical site between a pivoting clamp arm (not shown) and an ultrasonic blade (not shown) to thereby cut and/or seal the tissue.

Instrument (210) comprises handle assembly (220) and shaft assembly (230). Shaft assembly (230) comprises an outer sheath (232), an inner tube (234) slidably disposed within outer sheath (232), and waveguide (236) disposed within inner tube (234). Waveguide (236) extends proximally from a proximal end (232A) of outer sheath (232). A threaded bore (237) is formed in a proximal end of waveguide (236). Shaft assembly (230) further comprises a body portion (238) and a rotatable knob (240). A proximal end of rotatable knob (240) is rotatably coupled with a distal end of body portion (238). An interior bore (244) passes longitudinally through both body portion (238) and knob (240). A first annular recess (240A) and a second annular recess (240B) are formed in an interior surface of interior bore (244) of knob (240). Outer sheath (232), inner tube (234), and waveguide (236) are slidably disposed within interior bore (244) such that body portion (238) and knob (240) are longitudinally translatable between a distal longitudinal position and a proximal longitudinal position relative to outer sheath (232), inner tube (234), and waveguide (236).

A proximal portion of outer sheath (232), inner tube (234), and waveguide (236) extends proximally from body portion (238). A metal ring (241) and a locking member (242) are secured to the proximal portion of outer sheath (232) and waveguide (236). Metal ring (241) is positioned proximally of locking member (242). Locking member (242) is positioned about the proximal portion of outer sheath (232) and extends distally into interior bore (244) of body portion (238) and knob (240). Body portion (238) and knob (240) are keyed within locking member (242) such that a locking member (242) will rotate with body portion (238) and knob (240); and such that body portion (238) and knob (240) are longitudinally slidable relative to locking member (242). A plurality of resilient arms (243) are defined within a distal portion of locking member (242). Resilient arms (243) are biased outwardly away from outer sheath (232). A tab (243A) extends from a distal end of each resilient arm (243) of plurality of resilient arms (243). Tabs (243A) are configured to rest within first annular recess (240A) when outer sheath (232), inner tube (234), and waveguide (236) are in the proximal position as shown in FIG. 9A-9C. Tabs (243A) are configured to rest within second annular recess (240B) when outer sheath (232), inner tube (234), and waveguide (236) are in the distal position as shown in FIG. 9D. Tabs (243A) cooperate with annular recesses (240A, 240B), similar to detent features, to selectively maintain the longitudinal position of body portion (238) and knob (240) relative to shaft assembly (230).

Handle assembly (220) comprises a housing (222). A distal portion of housing (222) defines a socket (224) configured to receive body portion (238) of shaft assembly (230). Threaded stud (12E) of horn (12D) of transducer assembly (12) extends through housing (222) into socket (224). Handle assembly (220) further comprises a control module (267), motor (250), a solenoid (260), and a magnet (264). Control module (267) is configured to control the operations of motor (250) and solenoid (260) based at least in part on signals from magnet (264) and switch (265). By way of example only, control module (267) may include a microprocessor, an ASIC, a printed circuit board, one or more features storing a control logic, and/or any other suitable components as will be apparent to those of ordinary skill in the art in view of the teachings herein. Control module (267) is further coupled with a power source (212), which may be provided by generator (16) and/or some other type of power source that is integrated within handle assembly (220) or external to handle assembly (220). Motor (250) is configured to rotate transducer assembly (12) within handle assembly (220). Motor (250) is operable to turn in both clockwise and counter clockwise directions as driven by control module (267). Motor (250) may comprise a hub motor, a hollow shaft motor, a hollow shaft pancake motor, or any other type of motor appropriate to cause rotation of transducer assembly (12). Methods and structures by which motor (250) may cause rotation of transducer assembly (12) will be apparent to those of ordinary skill in the art according to the teachings herein. By way of example only, motor (250) may be coupled with transducer assembly (12), to thereby cause rotation of transducer assembly (12), in accordance with at least some of the teachings of U.S. Pub. No. 2012/0116260, entitled "Surgical Instrument with Motorized Attachment Feature," published May 10, 2012, issued as U.S. Pat. No. 10,085,792 on Oct. 2, 2018, the disclosure of which is incorporated by reference herein; and/or U.S. patent application Ser. No. 13/484,547, entitled "Loading Cartridge for Surgical Instrument End Effector," filed May 5, 2012, issued as U.S. Pat. No. 9,301,772 on Apr. 5, 2016, the disclosure of which is incorporated by reference herein. Motor (250) may contact a portion of transducer assembly (12) at a node associated with resonant ultrasonic vibrations communicated from piezoelectric stack (12J) to horn (12D).

Solenoid (260) comprises a vertically translatable locking member (262). As will be discussed in more detail below, solenoid (260) is configured to drive locking member (262) vertically to engage and/or disengage shaft assembly (230) to thereby prevent rotation of shaft assembly (230) relative to handle assembly (220). Also as will be discussed in more detail below, magnet (264) is configured to sense the presence of metal ring (241) of shaft assembly (230) to thereby activate solenoid (260).

Figure 9E:
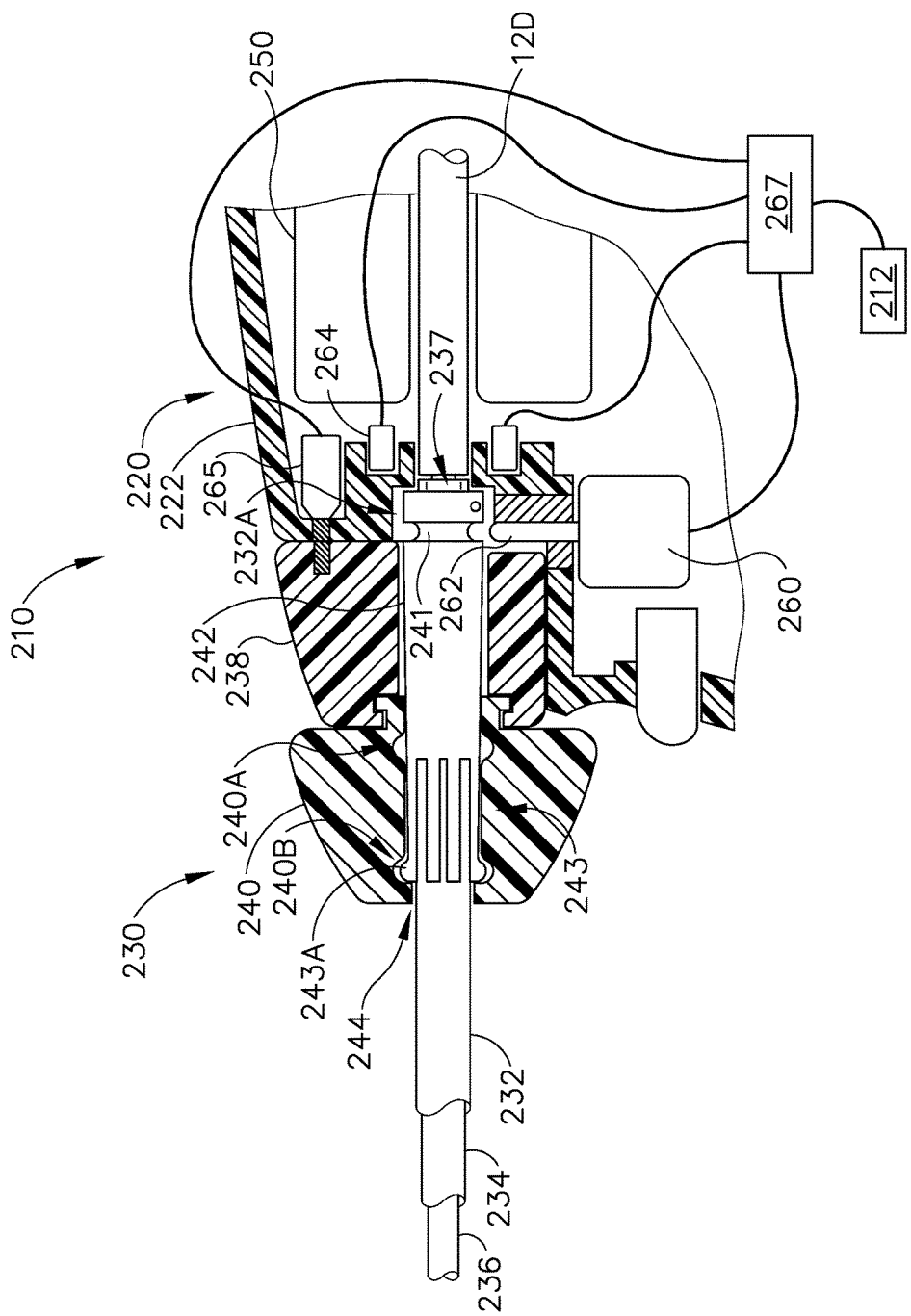
FIG. 9E depicts a partial cross-sectional view of the instrument of FIG. 8 with the locking member of FIG. 9C disengaged from the shaft assembly.
Figure 10:
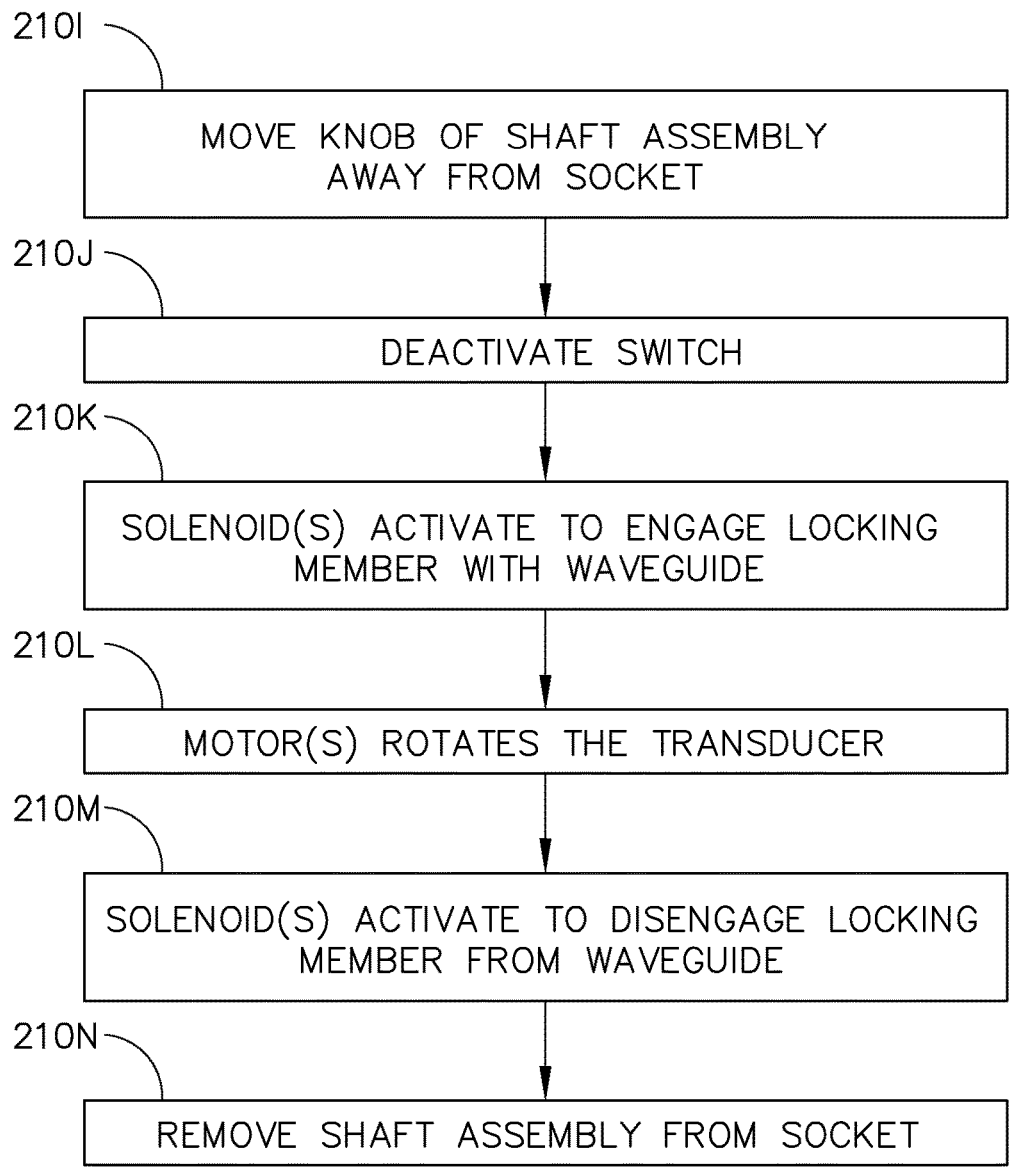
FIG. 10 depicts a flowchart showing steps of detaching the shaft assembly of FIG. 8 from the handle assembly of the instrument of FIG. 8.

FIGS. 8-9E show an exemplary set of the steps for attaching shaft assembly (230) to handle assembly (220) and waveguide (236) to transducer assembly (12). FIG. 9A shows shaft assembly (230) in a first longitudinal position relative to handle assembly (220). In this position, body portion (238) and knob (240) are in the distal longitudinal position relative to locking member (242), outer sheath (232), inner tube (234), and waveguide (236). The entire shaft assembly (230) is decoupled from handle assembly (220). FIG. 9B shows shaft assembly (230) moved into a second longitudinal position relative to handle assembly (220) (Block 210A of FIG. 8). In particular, the proximal end of shaft assembly (230) is inserted into socket (224) of housing (222). In this position, body portion (238) and knob (240) remain in the distal longitudinal position relative to locking member (242), outer sheath (232), inner tube (234), and waveguide (236). Also in this position, magnet (264) engages steel ring (241) and thereby holds shaft assembly (230) within socket (224). This engaging of steel ring (241) by magnet (264) provides tactile feedback to the user indicating that a connection has been made and causes a change in a magnetic field of magnet (264). Con troll module (267) senses the change in the magnetic field of magnet (264) (Block 210B of FIG. 8) and activates solenoid (260) to drive locking member (262) vertically upwardly from a first vertical position into a second vertical position (Block 210C of FIG. 8). FIG. 9C shows locking member (262) of solenoid (260) in the second vertical position. In the second vertical position, locking member (262) engages shaft assembly (230) and thereby prevents shaft assembly (230) from rotating relative to handle assembly (220).

As shown in FIG. 9D, with shaft assembly (230) held within socket (224) by magnet (264), the user continues to drive knob (240) and body portion (238) longitudinally proximally by overcoming the resistance caused by tabs (243A) of resilient arms (243) of locking member (242) within first annular recess (240A) (Block 210D of FIG. 8). Tabs (243A) are configured such that longitudinal force upon knob (240) and/or body portion (238) causes resilient arms (243) to move out of first annular recess (240A) inwardly and into interior bore (244). With tabs (243A) positioned in interior bore (244), knob (240) and body portion (238) may be translated longitudinally proximally until tabs (243A) of resilient arms (243) engage second annular recess (240B) as shown in FIG. 9D, such that body portion (238) and knob (240) are moved into the proximal longitudinal position relative to outer sheath (232), inner tube (234), and waveguide (236). During the time it takes for the user to drive knob (240) and body portion (238) longitudinally proximally, motor (250) rotates transducer assembly (12) such that threaded stud (12E) threads into threaded bore (237) (Block 210E of FIG. 8). It should be understood that motor (250) may be configured to rotate transducer assembly (12) a predetermined amount of times to achieve an appropriate connectivity between transducer assembly (12) and waveguide (236).

As noted above, motor (250) may be configured to rotate transducer assembly (12) until a predetermined amount of torque is sensed to achieve an appropriate connectivity between transducer assembly (12) and waveguide (236). For instance, control module (267) may be configured to stop rotation of motor (250) after a sensor senses a predetermined amount of back EMF of motor (250). In addition or in the alternative, control module (267) may stop rotation of motor (250) after a predetermined amount of angular travel of motor (250) or transducer assembly (12) is sensed by an encoder or other sensor. Other suitable ways in which an appropriate amount of torque may be detected or otherwise provided will be apparent to those of ordinary skill in the art in view of the teachings herein.

As shown in FIG. 9E, once knob (240) and body portion (238) have been driven longitudinally proximally such that tabs (243A) of resilient arms (243) have engaged second annular recess (240B), a proximal face of body portion (238) will be substantially engaged within a distal surface of housing (222) of handle assembly (220). In this substantially engaged position, a switch (265) within housing (222) of handle assembly (220) is activated (Block 210F of FIG. 8). Activation of switch (265) causes solenoid (260) to drive locking member (262) vertically downwardly from the second vertical position into the first vertical position such that locking member (262) disengages shaft assembly (230) and thereby allows shaft assembly (230) to rotate (Block 210G of FIG. 8) relative to handle assembly (220). It should be understood that, at this point, shaft assembly (230) is completely coupled with handle assembly (220); and further that waveguide (236) is acoustically coupled with transducer assembly (12) such that vibrations may be communicated from transducer assembly (12) along waveguide (236). Activation of switch (265) may further cause control module (267) to provide a signal that shaft assembly (230) has been successfully coupled with handle assembly (220) via an audible, tangible, and/or visible feedback feature (Block 210H of FIG. 8).

Figure 11A:
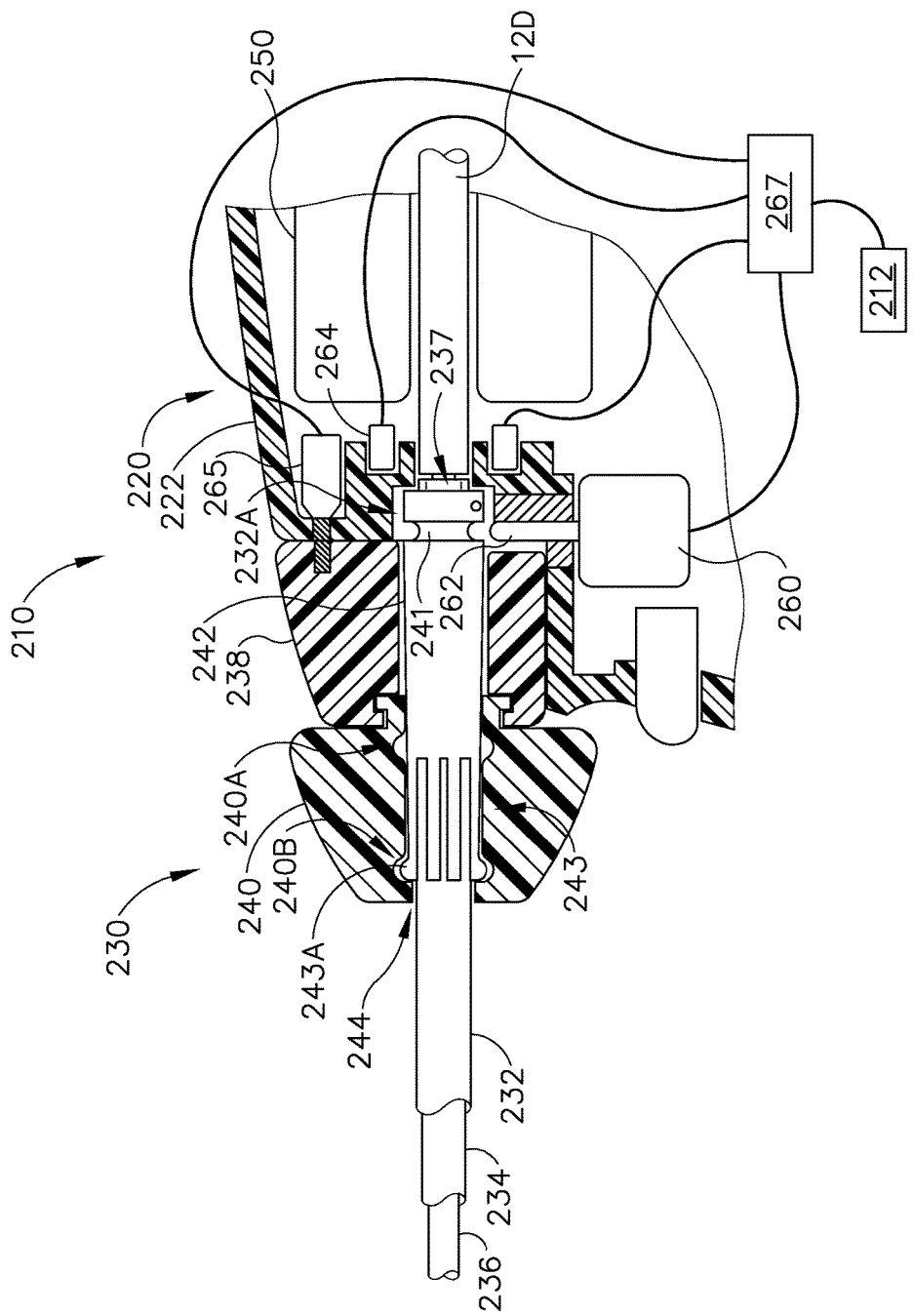
FIG. 11A depicts a partial cross-sectional view of the instrument of FIG. 8 with the shaft assembly in the second longitudinal position, the knob in the third longitudinal position, and with the locking member of FIG. 9C disengaged from the shaft assembly.
Figure 11B:
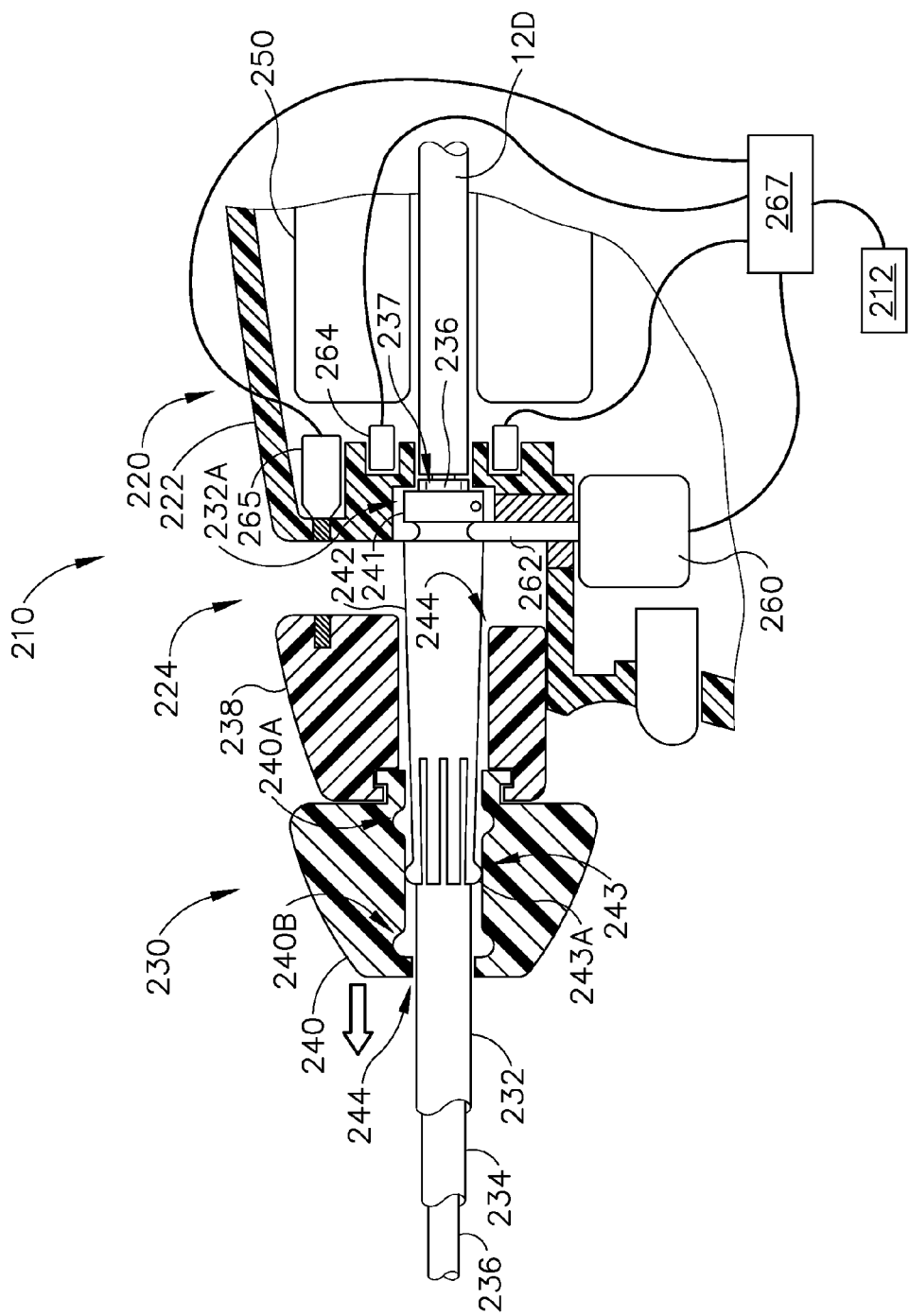
FIG. 11B depicts a partial cross-sectional view of the instrument of FIG. 8 with the locking member of FIG. 9C engaging the shaft assembly.
Figure 11C:
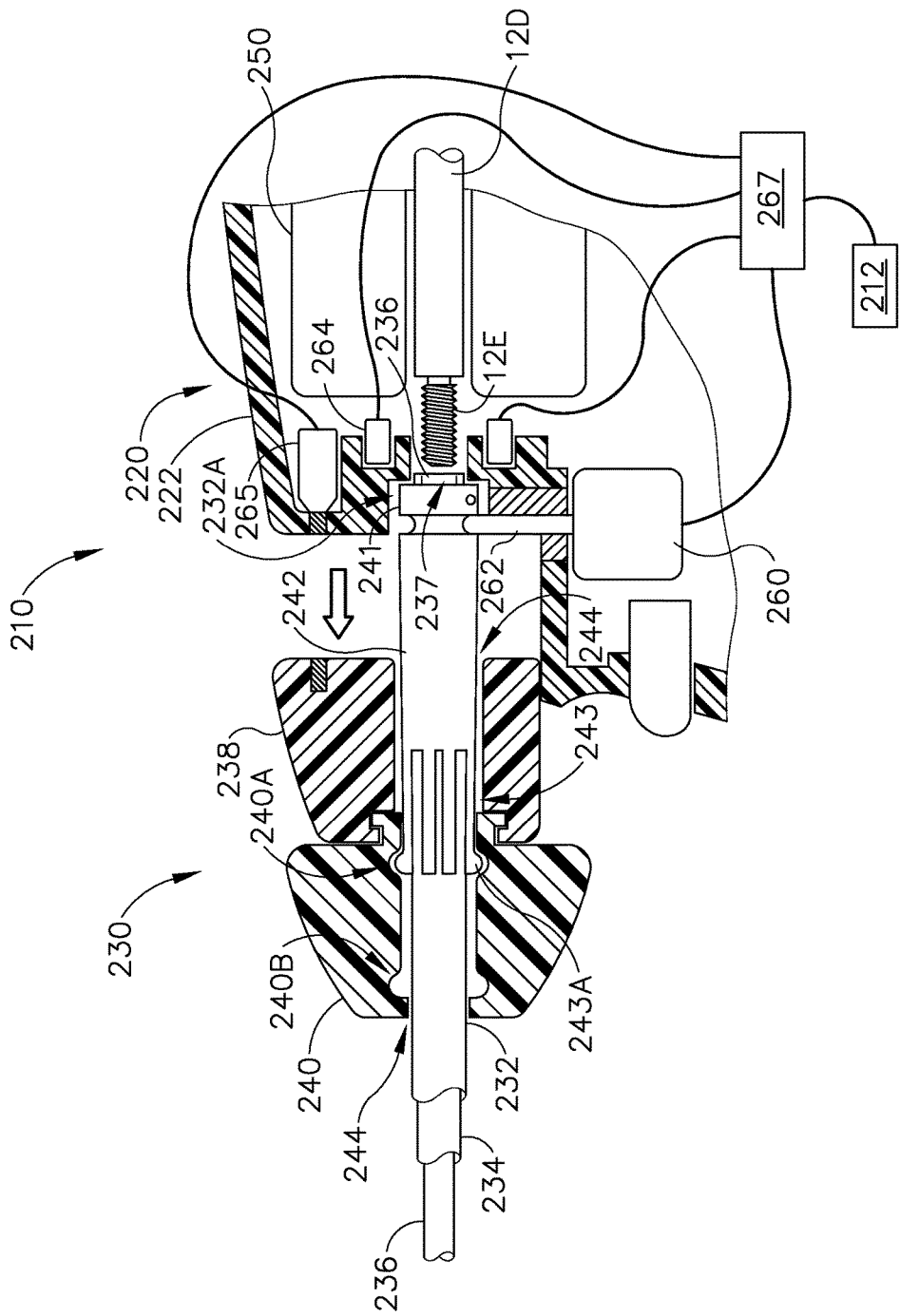
FIG. 11C depicts a partial cross-sectional view of the instrument of FIG. 8 with the knob of FIG. 9D moved back into the second longitudinal position.
Figure 11D:
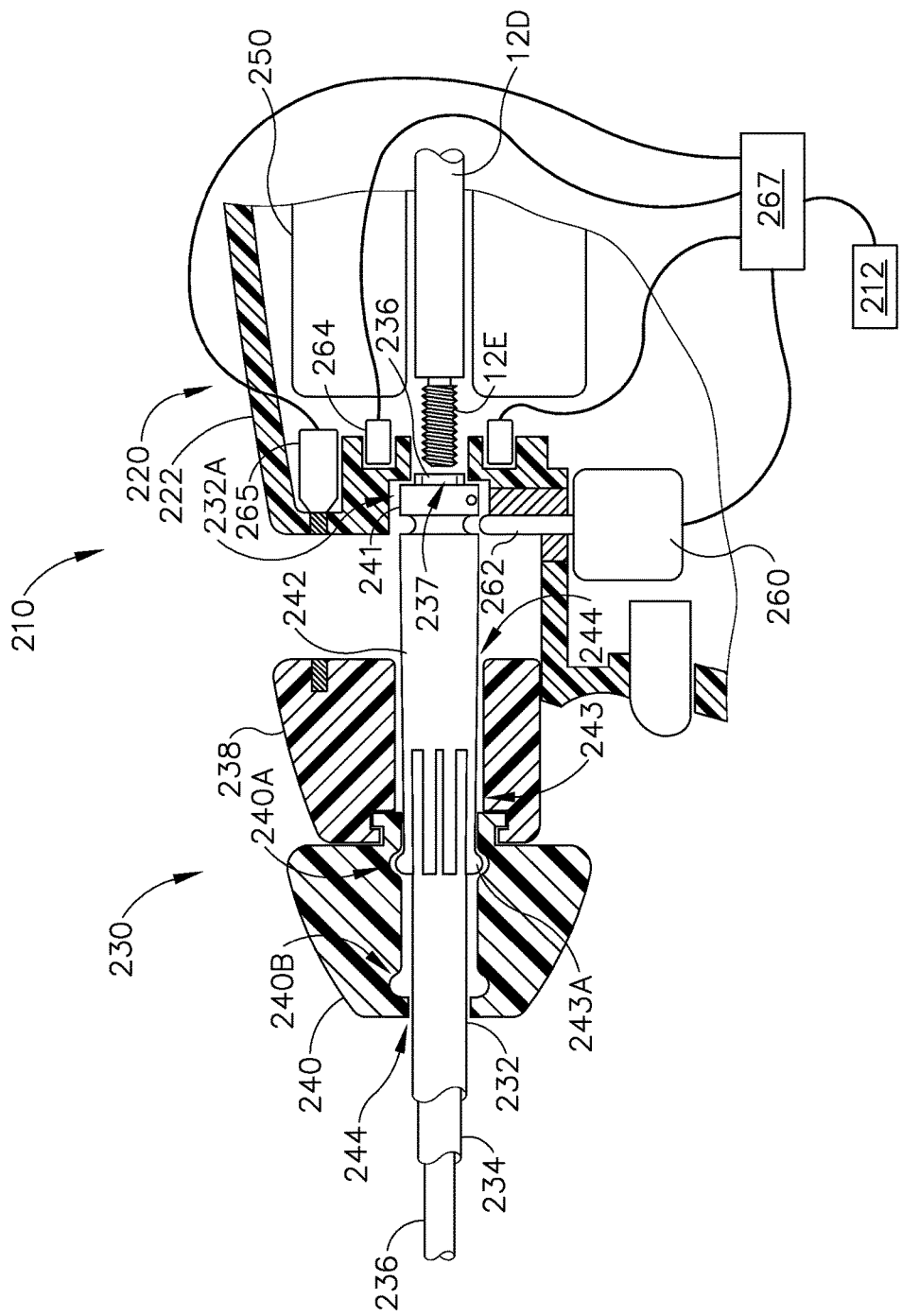
FIG. 11D depicts a partial cross-sectional view of the instrument of FIG. 8 with the locking member of FIG. 9C disengaged from the shaft assembly.
Figure 11E:
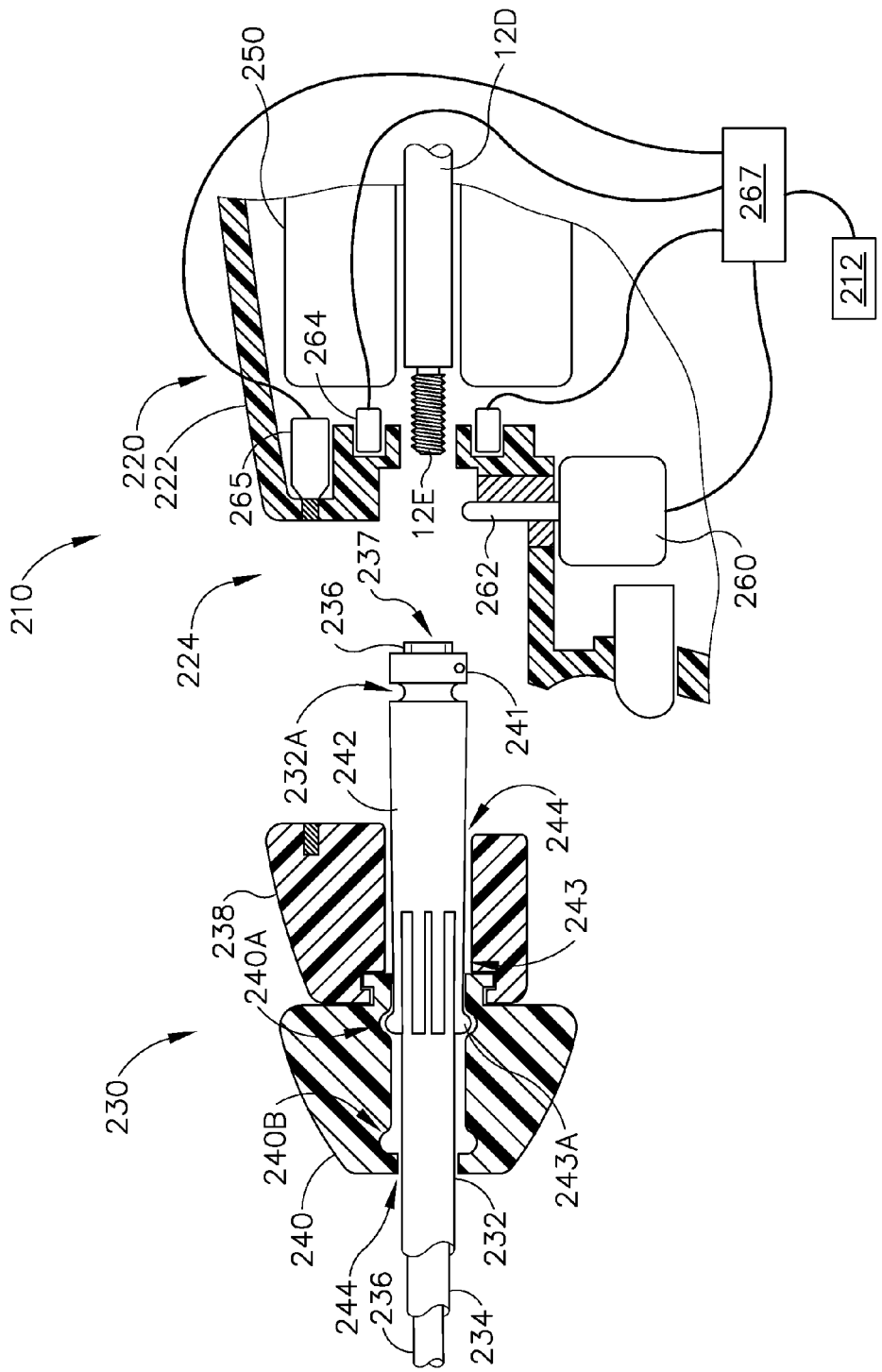
FIG. 11E depicts a partial cross-sectional view of the instrument of FIG. 8 with the shaft assembly moved back into the first longitudinal position.

FIGS. 10-11E show an exemplary set of steps for removing shaft assembly (230) from handle assembly (220) and waveguide (236) from transducer assembly (12). It should be understood that this process may be carried out during a surgical procedure (e.g., to replace one kind of shaft assembly (230) with another kind of shaft assembly (230)) or upon completion of a surgical procedure (e.g., to prepare handle assembly (220) and/or shaft assembly (230) for disposal and/or reclamation, etc.). FIG. 11A shows shaft assembly (230) in the second longitudinal position relative to handle assembly (220). In this position, body portion (238) and knob (240) are in the proximal longitudinal position relative to locking member (242), outer sheath (232), inner tube (234), and waveguide (236). To remove shaft assembly (230) from handle assembly (220), a user will apply distal longitudinal force upon knob (240) and/or body portion (238) (Block 210I of FIG. 10), overcoming the resistance provided by tabs (243A) of resilient arms (243) of locking member (242) within annular recess (240A), thereby translating body portion (238) and knob (240) toward the distal longitudinal position relative to locking member (242), outer sheath (232), inner tube (234), and waveguide (236) as shown in FIG. 11B. At this stage, waveguide (236) of shaft assembly (230) remains connected with threaded stud (12E) of transducer assembly (12). Thus, shaft assembly (230) remains substantially stationary relative to handle assembly (220) as body portion (238) and knob (240) move longitudinally distally. The distal longitudinal movement of body portion (238) and knob (240) will cause switch (265) to deactivate (Block 210J of FIG. 10). Deactivation of switch (265) causes solenoid (260) to drive locking member (262) vertically upwardly from the first vertical position into the second vertical position, as also shown in FIG. 11B, such that locking member (262) engages shaft assembly (230) and thereby prevents shaft assembly (230) from rotating (Block 210K of FIG. 10) relative to handle assembly (220). It should be understood that the activation of solenoid (260) and motor (250) may occur while knob (240) and body portion (238) are still transitioning from a proximal position as shown in FIG. 11A to an intermediate position as shown in FIG. 11B.

With shaft assembly (230) held within socket (224) by locking member (262), the user continues to drive knob (240) and body portion (238) longitudinally distally from the position shown in FIG. 11B to the position shown in FIG. 11C. As discussed above, tabs (243A) are configured such that longitudinal force upon knob (240) and/or body portion (238) has caused resilient arms (243) to move out of annular recess (240B) inwardly and into interior bore (244) at this stage. With tabs (243A) positioned in interior bore (244), knob (240) and body portion (238) may continue to be translated longitudinally distally until tabs (243A) of resilient arms (243) engage annular recess (240A) as shown in FIG. 11C, such that body portion (238) and knob (240) are moved into the distal longitudinal position relative to outer sheath (232), inner tube (234), and waveguide (236). During the time it takes for the user to drive knob (240) and body portion (238) longitudinally distally from the position shown in FIG. 11B to the position shown in FIG. 11C, motor (250) rotates transducer assembly (12) such that threaded stud (12E) threads out of threaded bore (237) (Block 210L of FIG. 10), thereby decoupling transducer assembly (12) from waveguide (236). After motor (250) has completely removed threaded stud (12E) from threaded bore (237) as shown in FIG. 11C, solenoid (260) drives locking member (262) vertically downwardly from the second vertical position into the first vertical position such that locking member (262) disengages shaft assembly (230) as shown in FIG. 11D (Block 210M of FIG. 10).

It should be understood that motor (250) may be configured to rotate transducer assembly (12) only until transducer assembly (12) and waveguide (236) are disconnected. For instance, control module (267) may be configured to stop rotation of motor (250), and then actuate solenoid (260) to retract locking member (262), after a sensor senses a predetermined amount of back EMF of motor (250) indicating that transducer assembly (12) has been disconnected from waveguide (236). Additionally or alternatively, control module (267) may be configured to stop rotation of motor (250), and then actuate solenoid (260) to retract locking member (262), after a predetermined amount of angular travel of motor (250) or transducer assembly (12) is sensed by an encoder or other sensor. For instance, if one full rotation of motor (250) is required to connect waveguide (236) with transducer assembly (12), control module (267) may be configured to permit two full rotations of motor (250) to disconnect waveguide (236) with transducer assembly (12) then stop further rotation of motor (250). Other suitable ways in which motor (250) may be automatically stopped and solenoid (260) may be automatically actuated will be apparent to those of ordinary skill in the art in view of the teachings herein.

With body portion (238) and knob (240) now in the distal longitudinal position relative to outer sheath (232), inner tube (234), and waveguide (236), and with shaft assembly (230) now disconnected from transducer assembly (12) and locking member (263), the user may remove shaft assembly (230) from socket (224) of handle assembly (220) (Block 210N of FIG. 10). FIG. 11E shows shaft assembly (230) disengaged from socket (224) of handle assembly (220) and moved back to the first longitudinal position relative to handle assembly (220). Shaft assembly (230) may then be disposed of, reprocessed, replaced, and/or otherwise dealt with.

B. Second Exemplary Motorized Acoustic Assembly Attachment Apparatus

Figure 12:
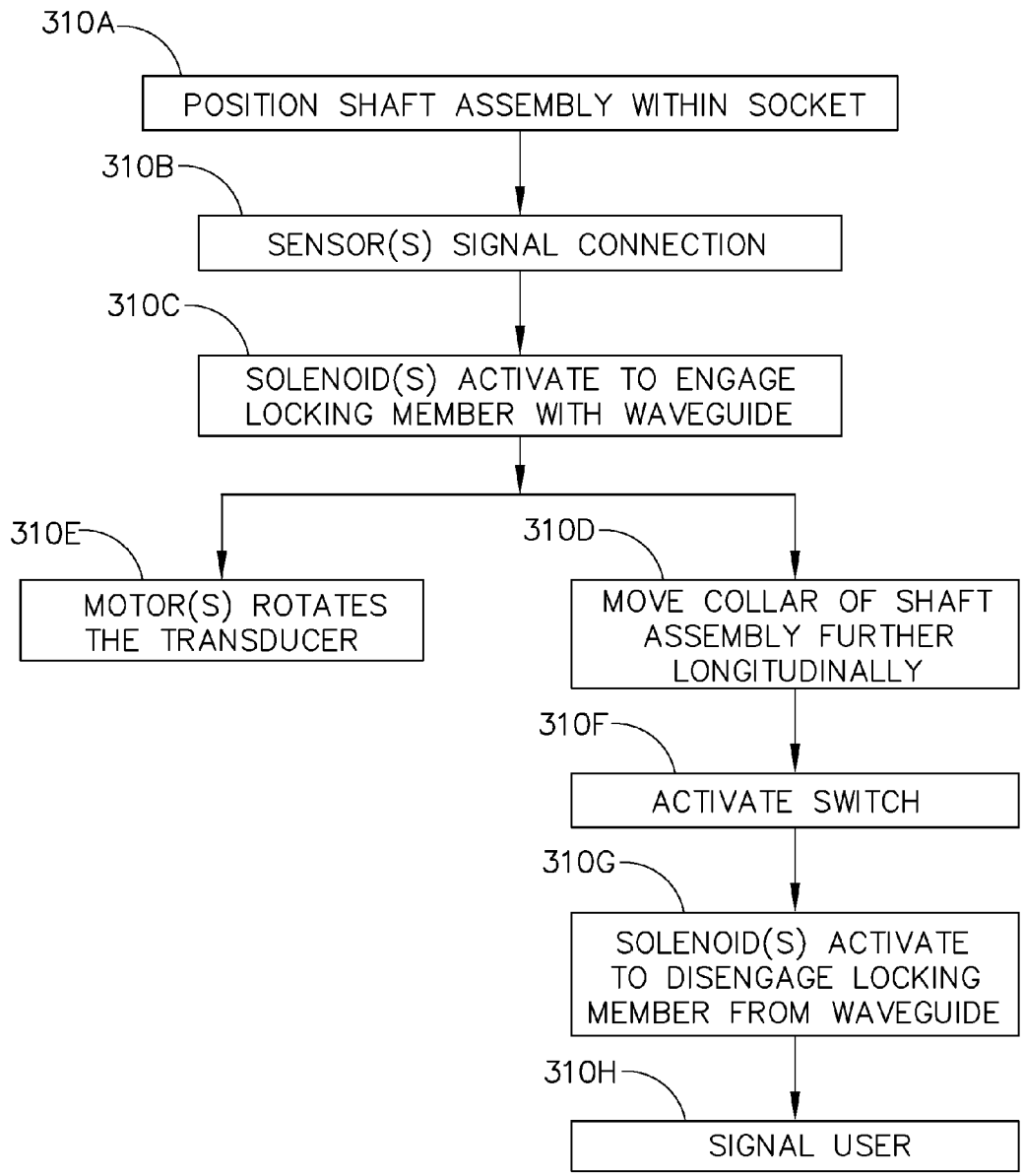
FIG. 12 depicts a flowchart showing steps of attaching an exemplary alternative shaft assembly to a handle assembly of another exemplary variation of the instrument of FIG. 1.

FIGS. 13A-13E and 15A-15E show an exemplary alternative instrument (310) having a motor (350) that mechanically rotates transducer assembly (12) to thereby threadably couple a waveguide (336) with transducer assembly (12). FIG. 12 shows an exemplary process for attaching a shaft assembly (330) to a handle assembly (320) and waveguide (336) to transducer assembly (12). FIG. 14 shows an exemplary process for removing shaft assembly (330) from handle assembly (320) and waveguide (336) from transducer assembly (12). Instrument (310) of the present example is configured to operate substantially similar to instruments (10, 210) discussed above except for the differences discussed below. In particular, instrument (310) is configured to clamp tissue at a surgical site between a pivoting clamp arm (not shown) and an ultrasonic blade (not shown) to thereby cut and/or seal the tissue.

Instrument (310) comprises a handle assembly (320) and a shaft assembly (330). Shaft assembly (330) comprises an outer sheath (332), an inner tube (334) slidably disposed within outer sheath (332), and a waveguide (336) disposed within inner tube (334). Waveguide (336) extends proximally from a proximal end (332A) of outer sheath (332). A threaded bore (337) is formed in a proximal end of waveguide (336). Shaft assembly (330) further comprises a body portion (338), a rotatable knob (340), and a longitudinally translatable collar (339). A proximal end of rotatable knob (340) is rotatably coupled with a distal end of body portion (338). An interior bore (344) passes longitudinally through both body portion (338) and knob (340). Collar (339) is slidably positioned within interior bore (344) such that collar (339) is longitudinally translatable between a distal position and a proximal position relative to body portion (338) and knob (340). As will be appreciated from the discussion below, when collar (339) is in the distal position relative to body portion (338) and knob (340), a proximal portion of collar (339) is disposed within interior bore (344) of body portion (338) and knob (340) while a distal portion of collar (339) remains exposed. When collar (339) is in the proximal position relative to body portion (338) and knob (340), a substantial portion of collar (339) is disposed within interior bore (344) of body portion (338) and knob (340). An annular tab (343) extends outwardly from a proximal end of collar (339). Tab (343) of collar (339) is configured to bear against an interior surface of interior bore (344) to thereby resist longitudinal translation of collar (339) relative to body portion (338) and knob (340). Outer sheath (332), inner tube (334), and waveguide (336) are secured within collar (339) and interior bore (344). A proximal portion of outer sheath (332), inner tube (334), and waveguide (336) extends proximally from body portion (338). A metal ring (341) is secured to the proximal portion of outer sheath (332) and waveguide (336).

Handle assembly (320) comprises a housing (322). A distal portion of housing (322) defines a socket (324) configured to receive body portion (338) of shaft assembly (330). Threaded stud (12E) of horn (12D) of transducer assembly (12) extends through housing (322) into socket (324). Handle assembly (320) further comprises a control module (367), a motor (350), a solenoid (360), and a magnet (364). Control module (367) is configured to control the operations of motor (350) and solenoid (360) based at least in part on signals from magnet (364) and switch (365). By way of example only, control module (367) may include a microprocessor, an ASIC, a printed circuit board, one or more features storing a control logic, and/or any other suitable components as will be apparent to those of ordinary skill in the art in view of the teachings herein. Control module (367) is further coupled with a power source (312), which may be provided by generator (16) and/or some other type of power source that is integrated within handle assembly (320) or external to handle assembly (320). Motor (350) is configured to rotate transducer assembly (12) within handle assembly (320). Motor (350) is operable to turn in both clockwise and counter clockwise directions as driven by control module (367). Motor (350) may comprise a hub motor, a hollow shaft motor, a hollow shaft pancake motor, or any other type of motor appropriate to cause rotation of transducer assembly (12). Methods and structures by which motor (350) may cause rotation of transducer assembly (12) will be apparent to those of ordinary skill in the art according to the teachings herein. By way of example only, motor (350) may be coupled with transducer assembly (12), to thereby cause rotation of transducer assembly (12), in accordance with at least some of the teachings of U.S. Pub. No. 2012/0116260, entitled "Surgical Instrument with Motorized Attachment Feature," published May 10, 2012, issued as U.S. Pat. No. 10,085,792 on Oct. 2, 2018, the disclosure of which is incorporated by reference herein; and/or U.S. patent application Ser. No. 13/484,547, entitled "Loading Cartridge for Surgical Instrument End Effector," filed May 5, 2012, issued as U.S. Pat. No. 9,301,772 on Apr. 5, 2016, the disclosure of which is incorporated by reference herein. Motor (350) may contact a portion of transducer assembly (12) at a node associated with resonant ultrasonic vibrations communicated from piezoelectric stack (12J) to horn (12D).

Solenoid (360) comprises a translatable locking member (362). As will be discussed in more detail below, solenoid (360) is configured to drive locking member (362) to engage and/or disengage shaft assembly (330) to thereby prevent rotation of shaft assembly (330) relative to handle assembly (320). Also as will be discussed in more detail below, magnet (364) is configured to sense the presence of metal ring (341) of shaft assembly (330) to thereby activate solenoid (360).

Figure 13A:
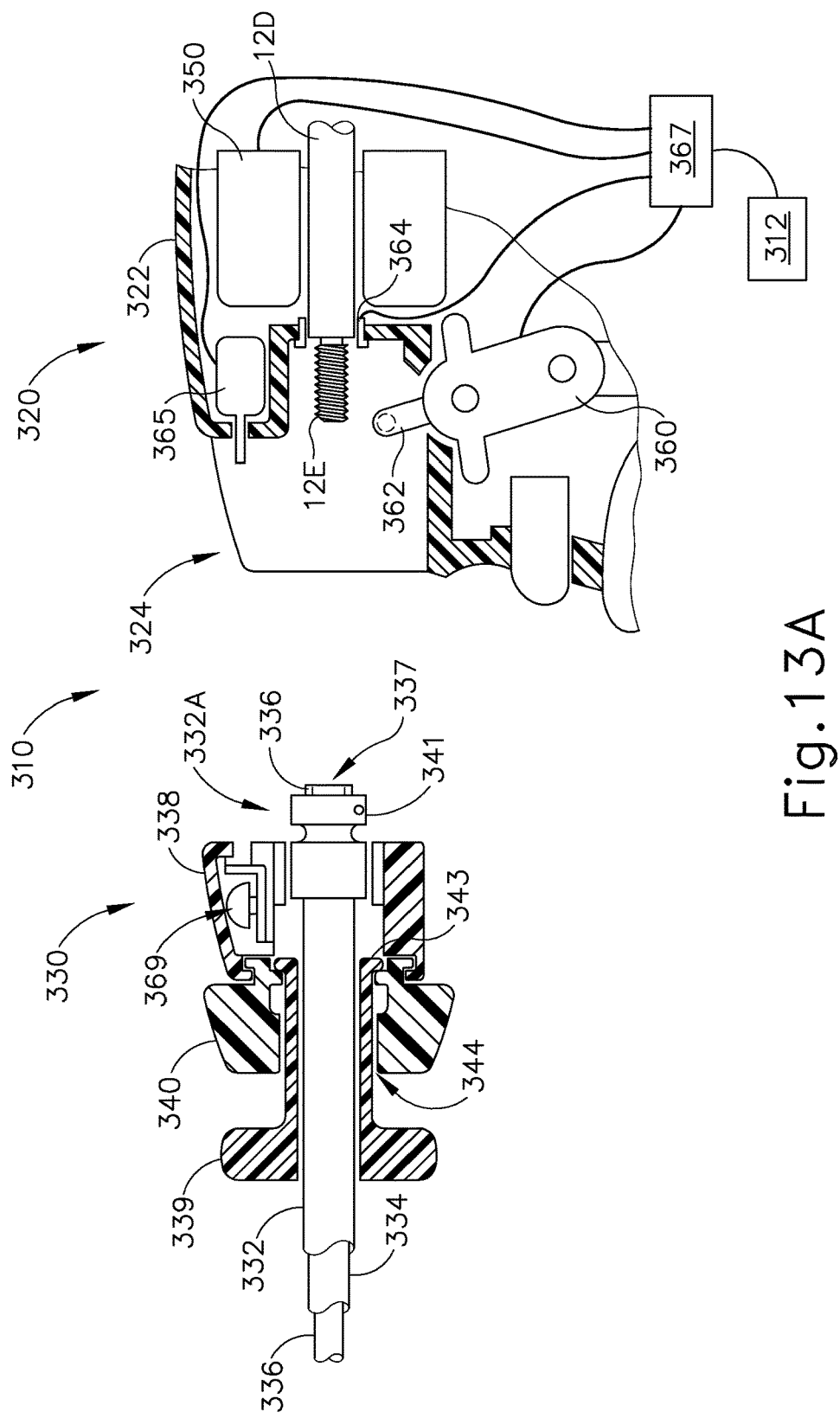
FIG. 13A depicts a partial cross-sectional view of the instrument of FIG. 12 with the shaft assembly in a first longitudinal position.
Figure 13C:
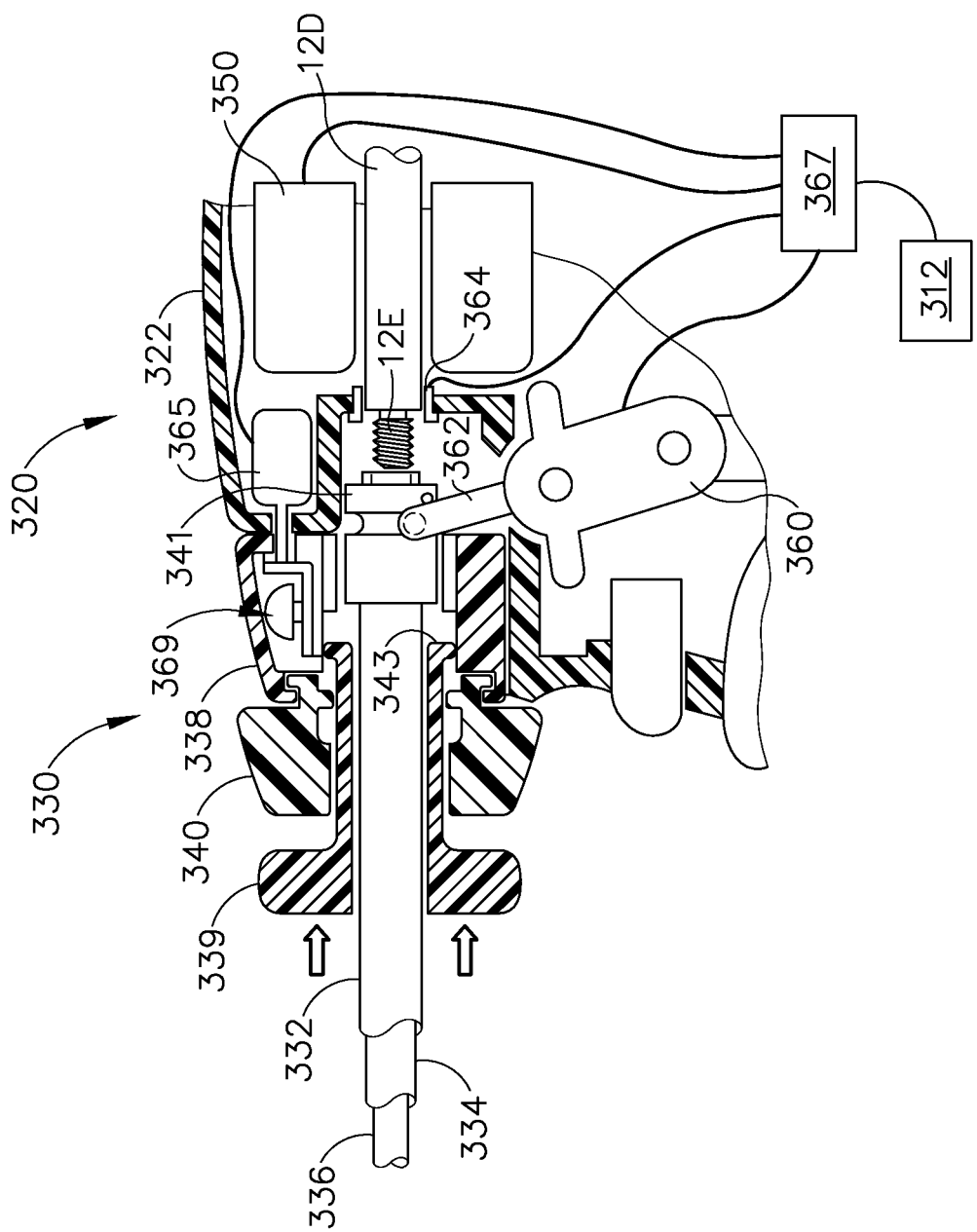
FIG. 13C depicts a partial cross-sectional view of the instrument of FIG. 12 with a locking member engaging the shaft assembly.
Figure 13D:
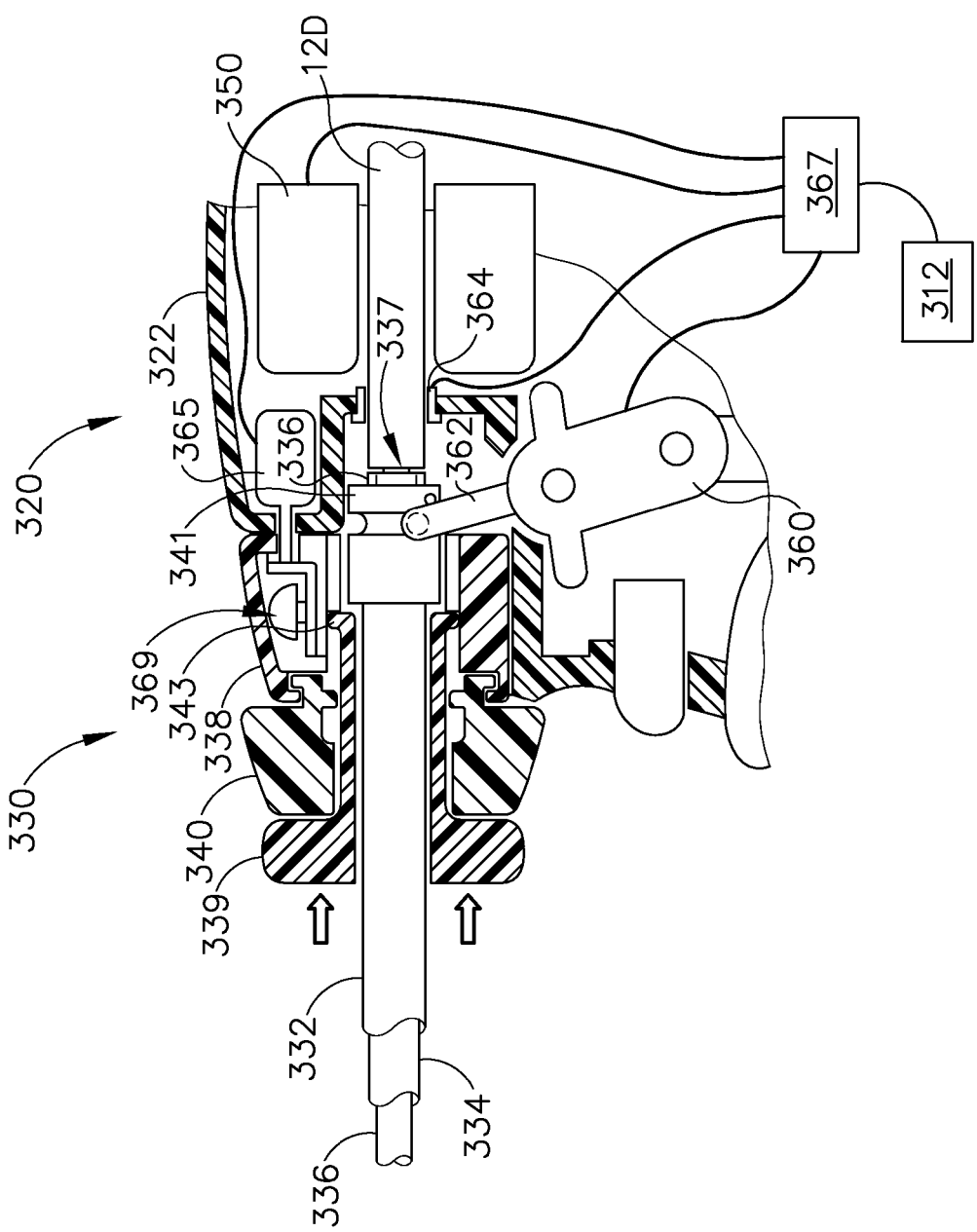
FIG. 13D depicts a partial cross-sectional view of the instrument of FIG. 12 with a collar of the shaft assembly moved into a third longitudinal position.
Figure 13E:
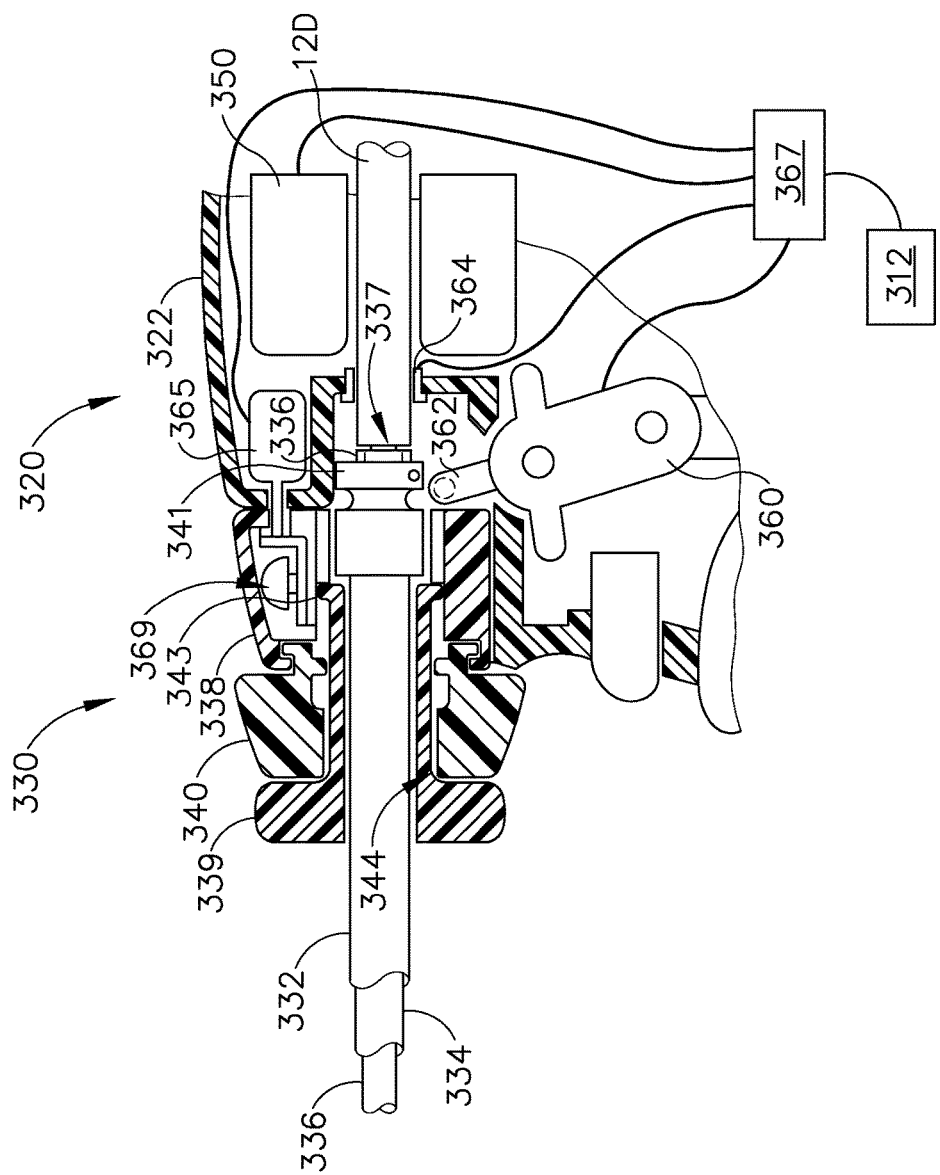
FIG. 13E depicts a partial cross-sectional view of the instrument of FIG. 12 with the locking member of FIG. 13C disengaged from the shaft assembly.
Figure 14:
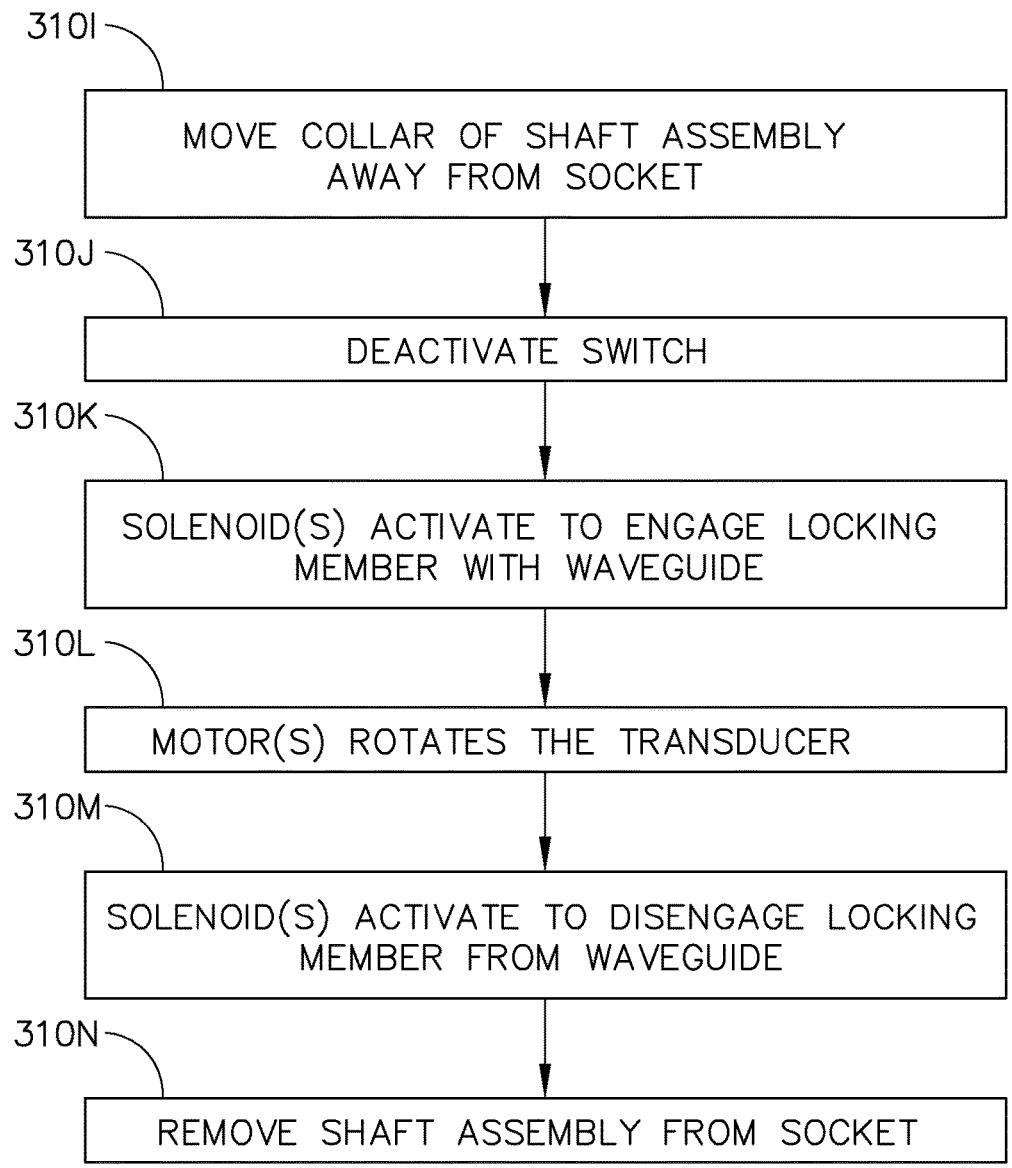
FIG. 14 depicts a flowchart showing steps of detaching the shaft assembly of FIG. 12 from the handle assembly of the instrument of FIG. 12.

FIGS. 12-13E show an exemplary set of the steps for attaching shaft assembly (330) to handle assembly (320) and waveguide (336) to transducer assembly (12). FIG. 13A shows shaft assembly (330) in a first longitudinal position relative to handle assembly (320). In this position, collar (339) is in the distal longitudinal position relative to body portion (338) and knob (340); and the entire shaft assembly (330) is decoupled from handle assembly (320). FIG. 13B shows shaft assembly (330) moved into a second longitudinal position relative to handle assembly (320) (Block 310A of FIG. 12). In particular, the proximal end of shaft assembly (330) is inserted into socket (324) of housing (322). At this stage, collar (339) remains in the distal longitudinal position relative to body portion (338) and knob (340). Also in this position, magnet (364) senses the presence of steel ring (341). This causes a change in a magnetic field of magnet (364). Control module (367) senses the change in the magnetic field of magnet (364) (Block 310B of FIG. 12) and activates solenoid (360) to drive locking member (362) upwardly from a first position into a second position (Block 310C of FIG. 12) as shown in FIG. 13C. In the second position, locking member (362) engages shaft assembly (330) and thereby prevents shaft assembly (330) from rotating relative to handle assembly (320). Once locking member (362) has engaged shaft assembly (330), control module (367) then activates motor (350) to rotate transducer assembly (12) relative to handle assembly (320). Motor (350) thereby drives threaded stud (12E) in threaded bore (337) (Block 310E of FIG. 12) to acoustically couple transducer assembly (12) with waveguide (336) as shown in FIG. 13D.

As also shown in FIG. 13C, the operator begins to translate collar (339) proximally relative to body portion (338) and knob (340) once body portion (338) is seated in socket (324) of housing (322). This may be done by overcoming the resistance caused by tab (343) against the interior surface of interior bore (344) (Block 310D of FIG. 12). As tab (343) reaches a proximal position as shown in FIG. 13D, a proximity switch (369) in body portion (338) senses the proximal positioning of tab (343). Proximity switch (369) is in communication with a switch (365) located within handle assembly (320), such that proximity switch (369) triggers switch (365) in response to detecting the proximal positioning of tab (343). Switch (365) in turn signals control module (367) to indicate the proximal positioning of tab (343), and control module (367) in turn activates solenoid to retract locking member (362) downwardly from the second position into the first position as shown in FIG. 13E, such that locking member (362) disengages shaft assembly (330) and thereby allows shaft assembly (330) to rotate (Block 310G of FIG. 12) relative to handle assembly (320). In some versions, during the time it takes for the user to drive collar (339) all the way to a proximal-most position (e.g., during the transition from the state shown in FIG. 13C to the state shown in FIG. 13D), motor (350) rotates transducer assembly (12) to a degree sufficient to fully couple transducer assembly (12) with waveguide (336).

It should be understood that motor (350) may be configured to rotate transducer assembly (12) a predetermined amount of times to achieve an appropriate connectivity between transducer assembly (12) and waveguide (336). It should also be understood that motor (350) may be configured to rotate transducer assembly (12) until a predetermined amount of torque is sensed to achieve an appropriate connectivity between transducer assembly (12) and waveguide (336). For instance, control module (367) may be configured to stop rotation of motor (350) after a sensor senses a predetermined amount of back EMF of motor (350). In addition or in the alternative, control module (367) may be configured to stop rotation of motor (350) after a predetermined amount of angular travel of motor (350) or transducer assembly (12) is sensed by an encoder or other sensor. Other suitable ways in which an appropriate amount of torque may be detected or otherwise provided will be apparent to those of ordinary skill in the art in view of the teachings herein.

It should also be understood that knob (340), collar (339), and other components of shaft assembly (330)—not including body portion (338)—rotate together relative to handle assembly (320), while body portion (338) does not rotate relative to handle assembly (320). It should also be understood that, at the stage shown in FIG. 13E, shaft assembly (330) is completely coupled with handle assembly (320); and further that waveguide (336) is acoustically coupled with transducer assembly (12) such that vibrations may be communicated from transducer assembly (12) along waveguide (336). Activation of switch (365) may further cause control module (367) to provide a signal that shaft assembly (330) has been successfully coupled with handle assembly (320) via an audible, tangible, and/or visible feedback feature (Block 310H of FIG. 12).

Figure 15A:
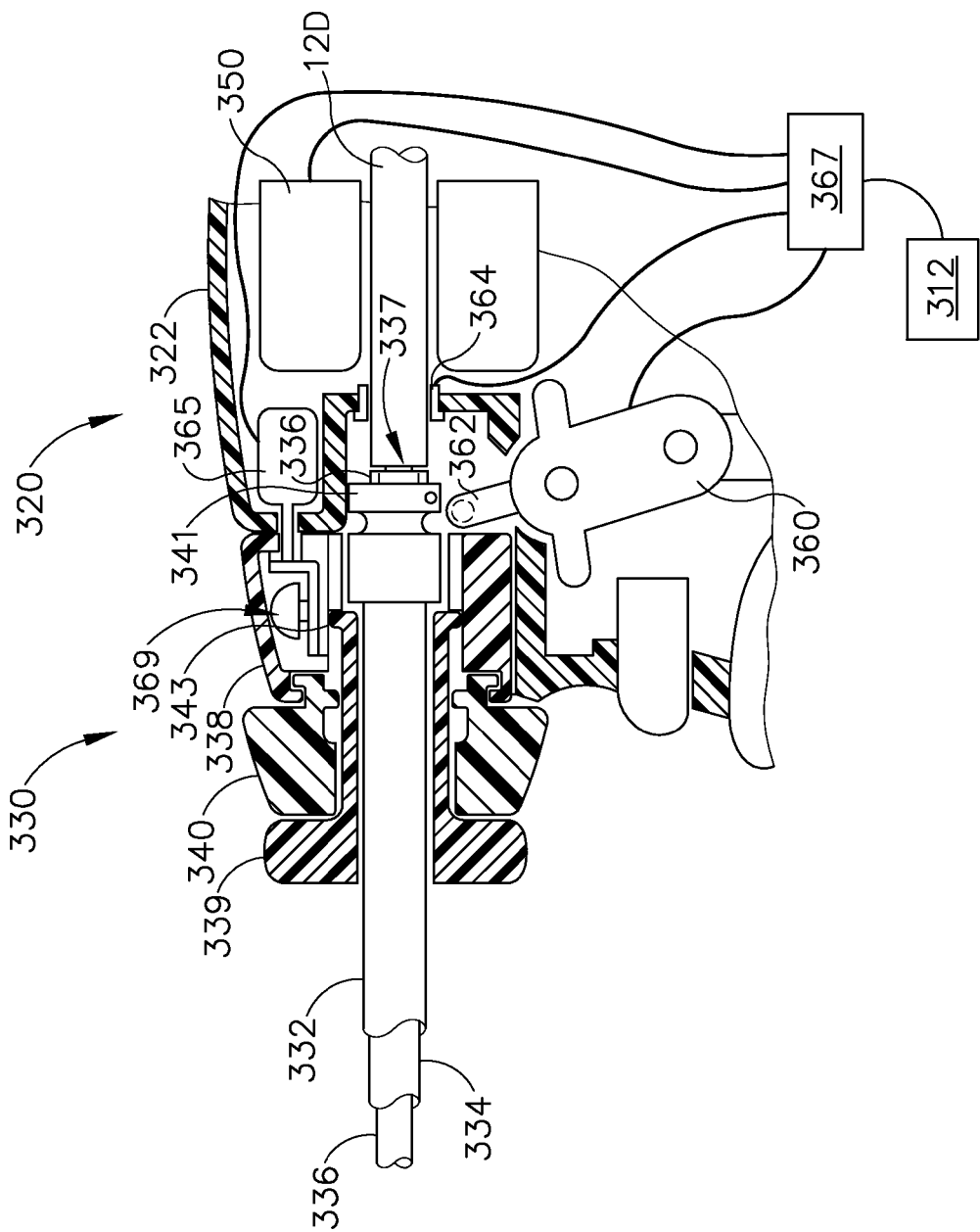
FIG. 15A depicts a partial cross-sectional view of the instrument of FIG. 12 with the shaft assembly in the second longitudinal position, the collar in the third longitudinal position, and with the locking member of FIG. 13C disengaged from the shaft assembly.
Figure 15B:
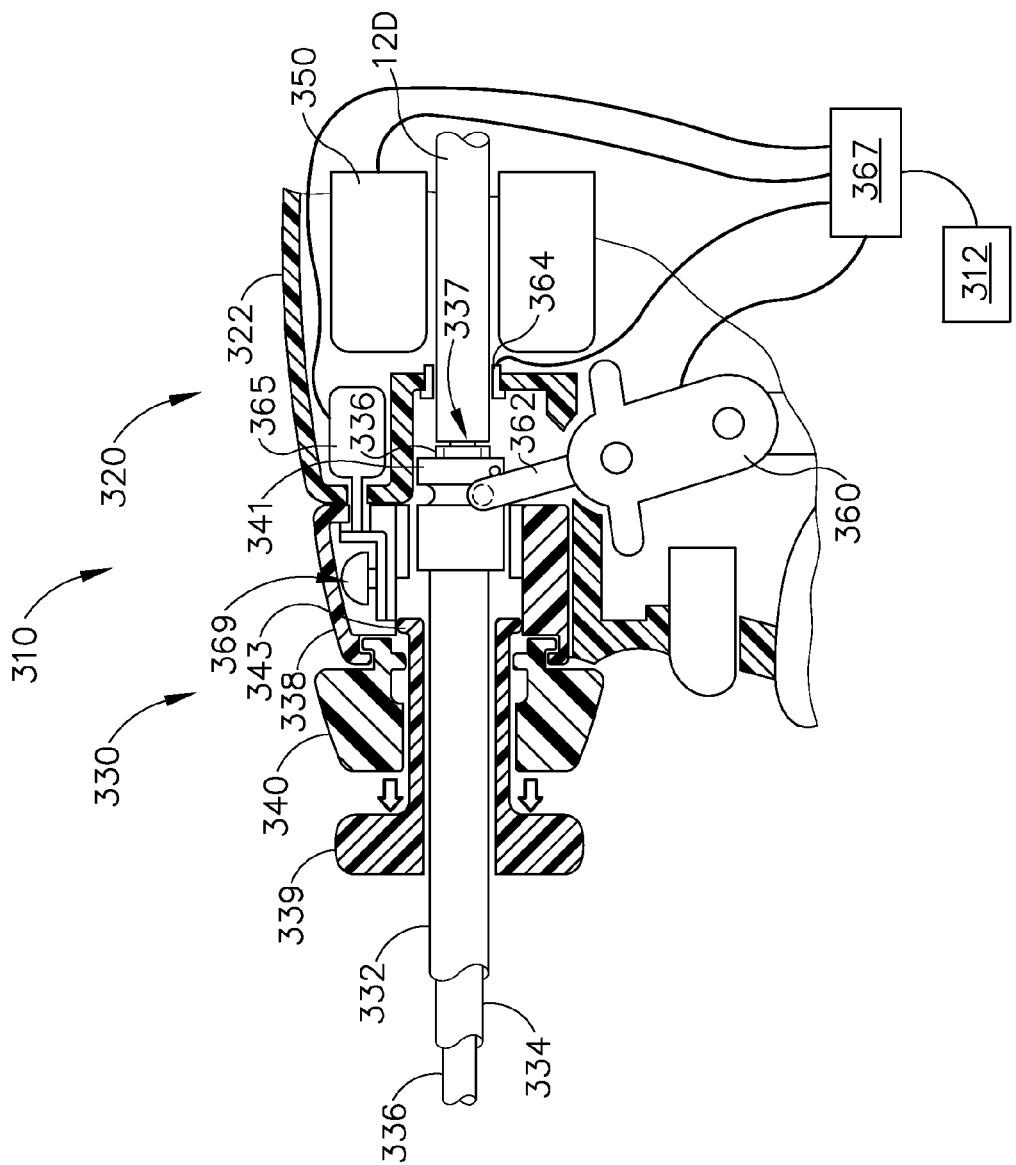
FIG. 15B depicts a partial cross-sectional view of the instrument of FIG. 12 with the locking member of FIG. 13C engaging the shaft assembly.
Figure 15C:
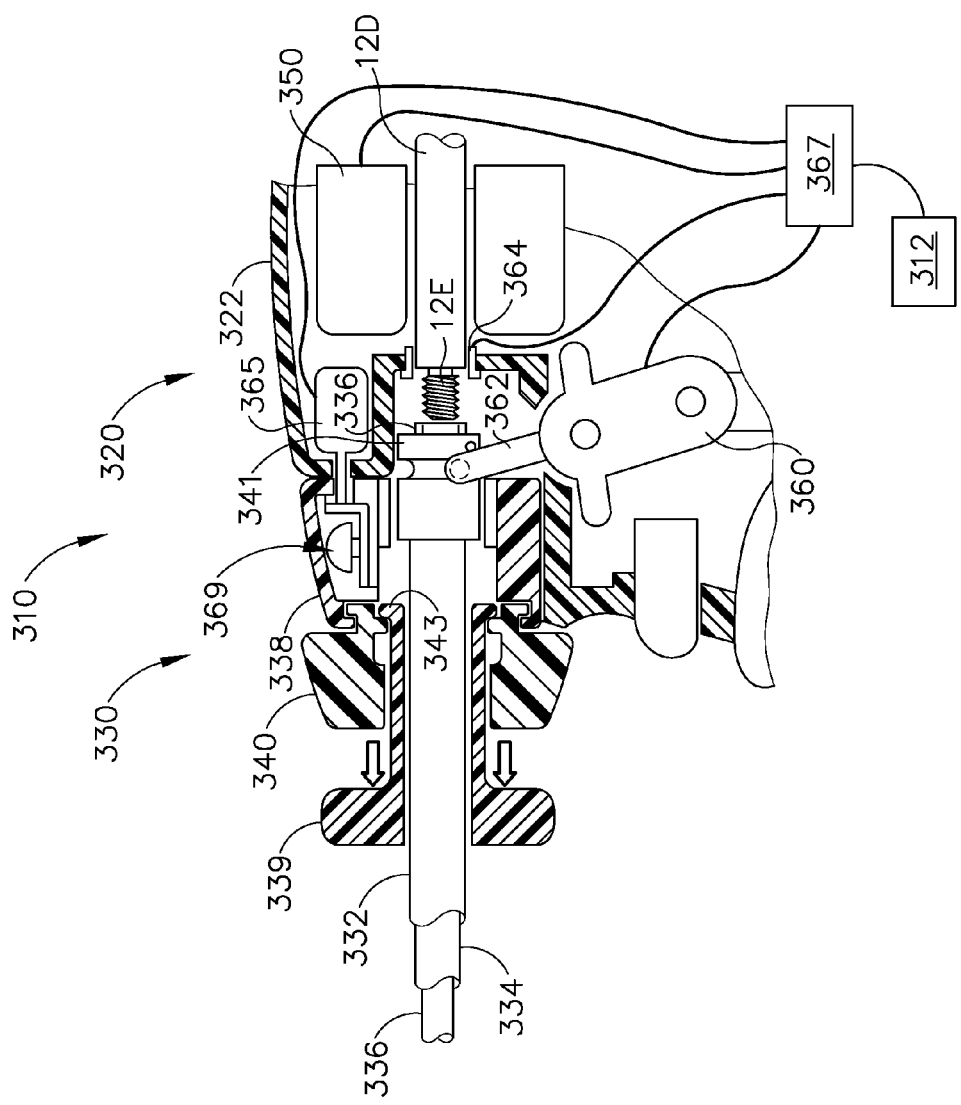
FIG. 15C depicts a partial cross-sectional view of the instrument of FIG. 12 with the collar of FIG. 13D moved back into the second longitudinal position.
Figure 15D:
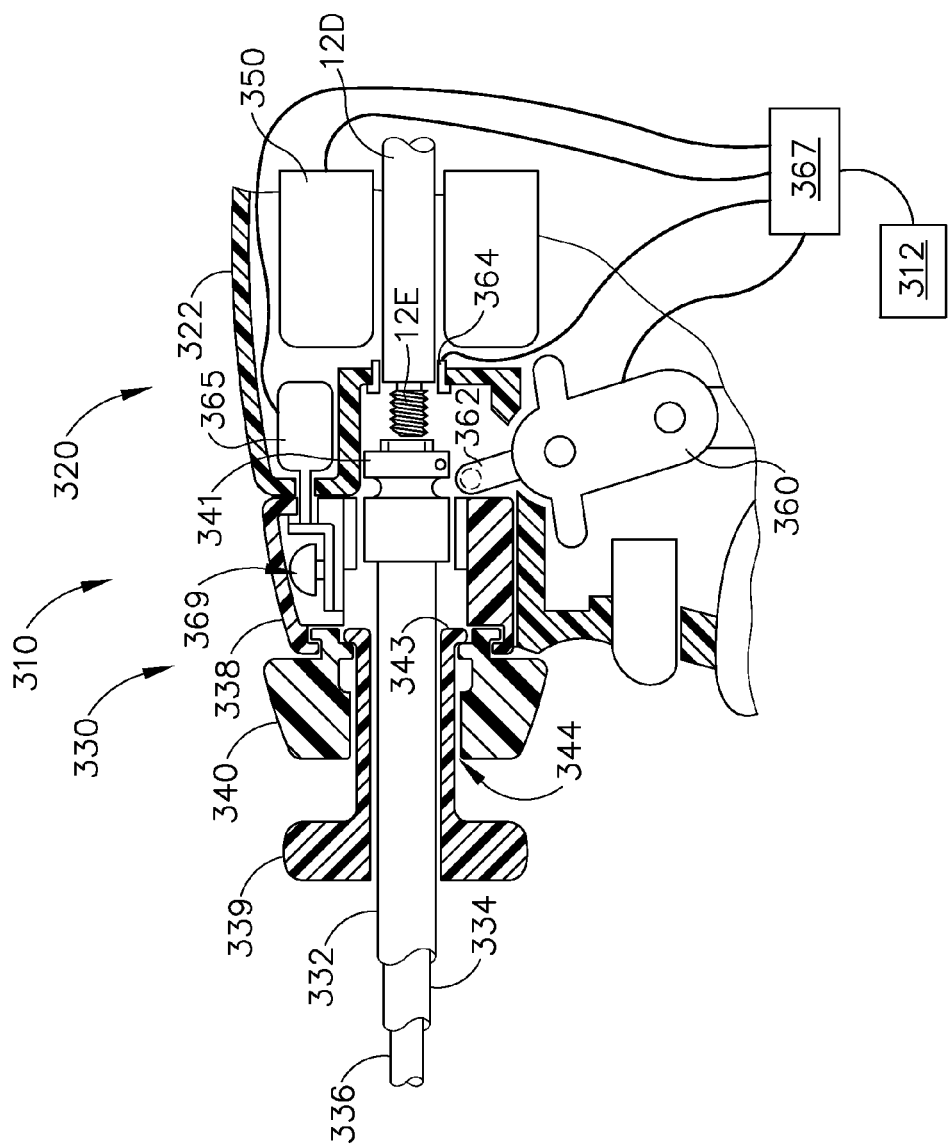
FIG. 15D depicts a partial cross-sectional view of the instrument of FIG. 12 with the locking member of FIG. 13C disengaged from the shaft assembly.
Figure 15E:
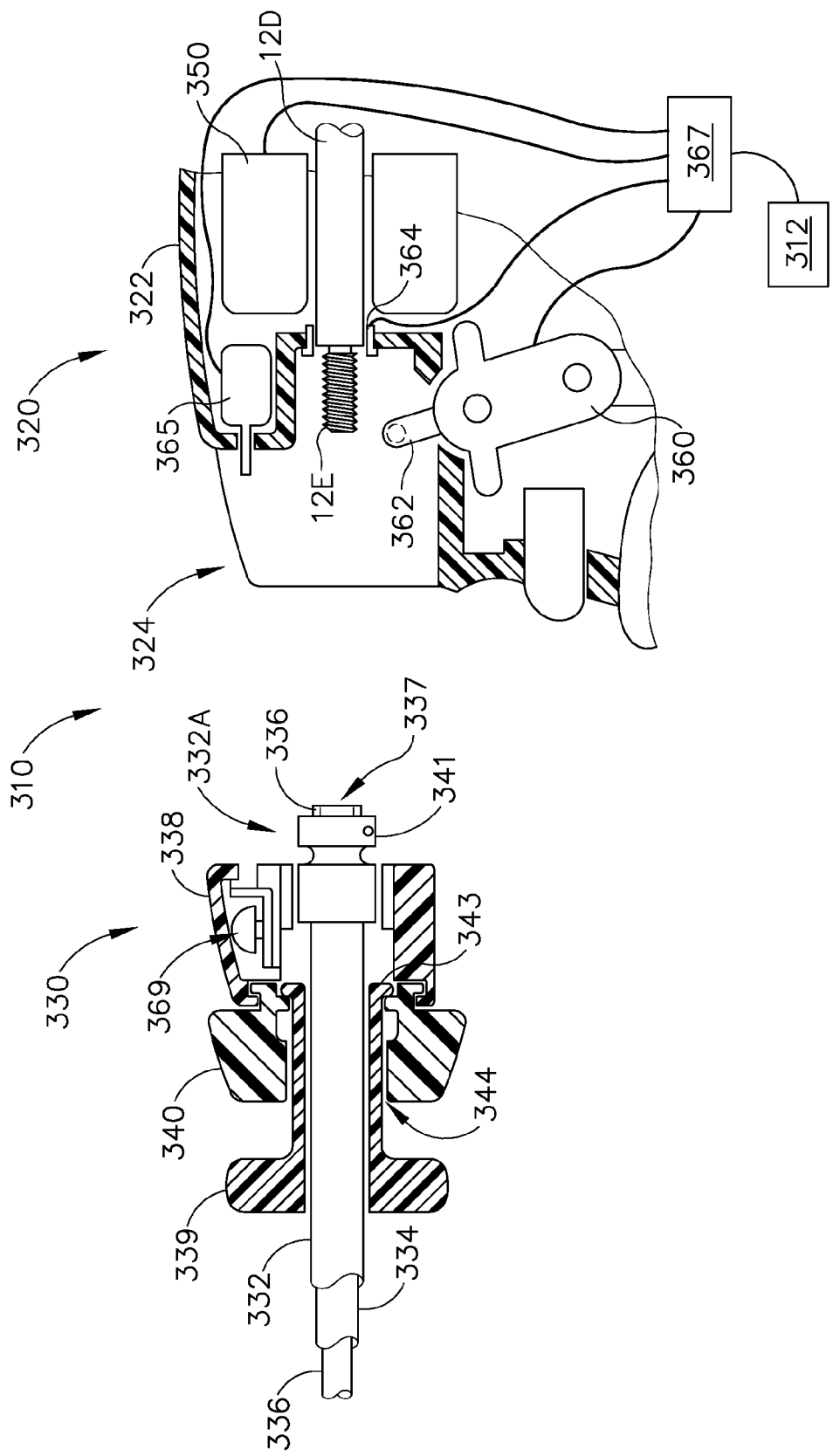
FIG. 15E depicts a partial cross-sectional view of the instrument of FIG. 12 with the shaft assembly moved back into the first longitudinal position.
Figure 16:
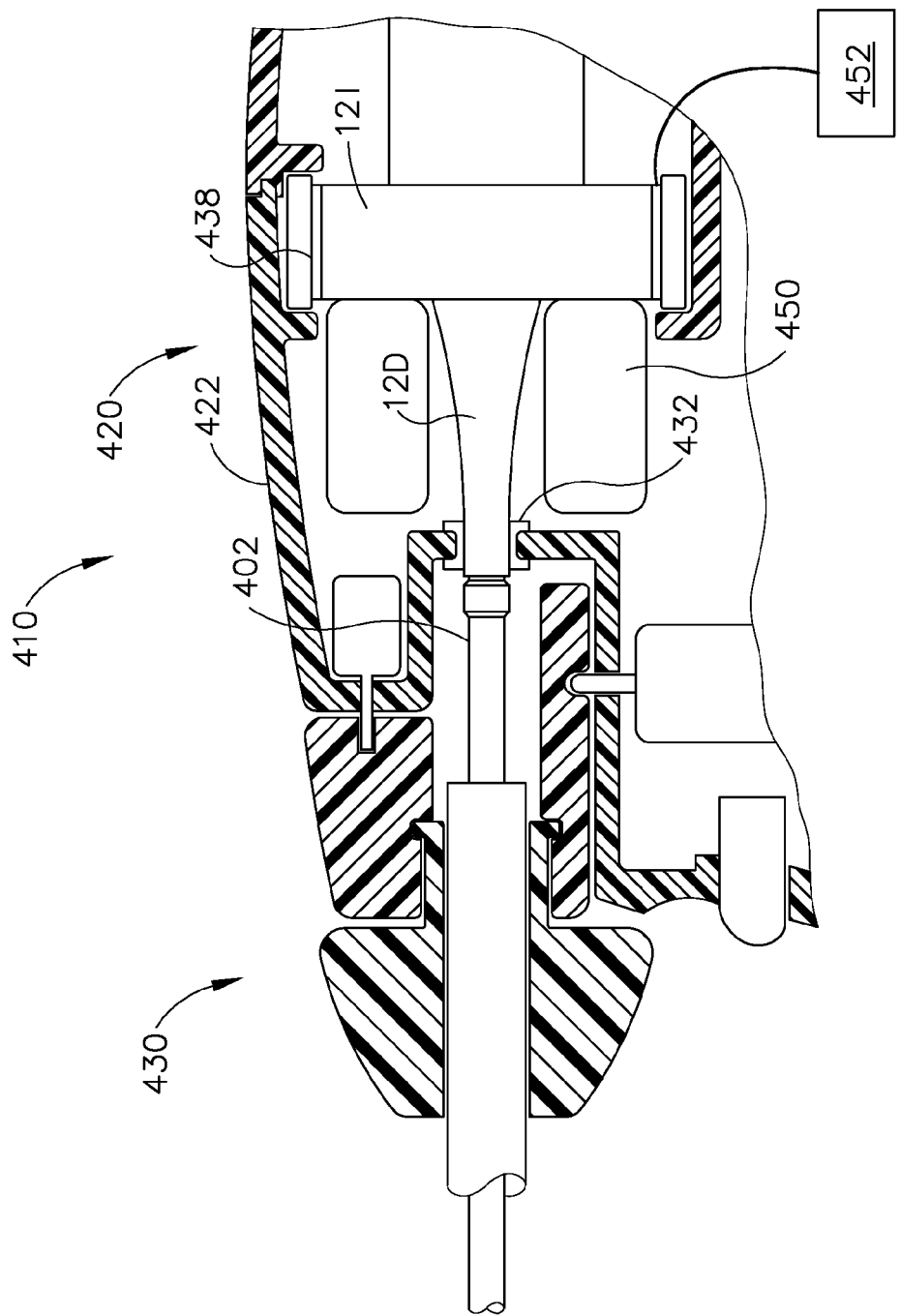
FIG. 16 depicts a partial cross-sectional view of yet another exemplary variation of the instrument of FIG. 1.

FIGS. 14-15E show an exemplary set of steps for removing shaft assembly (330) from handle assembly (320) and waveguide (336) from transducer assembly (12). It should be understood that this process may be carried out during a surgical procedure (e.g., to replace one kind of shaft assembly (330) with another kind of shaft assembly (330)) or upon completion of a surgical procedure (e.g., to prepare handle assembly (320) and/or shaft assembly (330) for disposal and/or reclamation, etc.). FIG. 15A shows shaft assembly (330) in the second longitudinal position relative to handle assembly (320). In this position, collar (339) is in the proximal longitudinal position relative to body portion (338) and knob (340). To remove shaft assembly (330) from handle assembly (320), a user will apply distal longitudinal force upon collar (339) (Block 310I of FIG. 14), overcoming the resistance caused by tab (343) against the interior surface of interior bore (344). At this stage, waveguide (336) of shaft assembly (330) remains connected with threaded stud (12E) of transducer assembly (12). Thus, shaft assembly (330) remains substantially stationary relative to handle assembly (320) as collar (339) moves longitudinally distally. The distal longitudinal movement of collar (339) relative to body portion (338) and knob (340) triggers proximity switch (369), which further deactivates switch (365) (Block 310J of FIG. 14). Deactivation of switch (365) in turn activates solenoid to advance locking member (362) upwardly from the first position to the second position as shown in FIG. 15B, such that locking member (362) engages shaft assembly (330) and thereby prevents shaft assembly (330) from rotating (Block 310K of FIG. 14) relative to handle assembly (320). Once locking member (362) is engaged with shaft assembly (330), control module (367) activates motor (350) to rotate transducer assembly (12) (Block 310L of FIG. 14), to thereby thread threaded stud (12E) out of threaded bore (337). It should be understood that the activation of solenoid (360) and motor (350) may occur while collar (339) is still transitioning from a proximal position as shown in FIG. 15A to an intermediate position as shown in FIG. 15B.

With shaft assembly (330) held within socket (324) by locking member (362), the user continues to drive collar (339) longitudinally distally from the position shown in FIG. 15B to the position shown in FIG. 15C. During the time it takes for the user to drive collar (339) longitudinally distally from the position shown in FIG. 15B to the position shown in FIG. 15C, motor (350) rotates transducer assembly (12) such that threaded stud (12E) threads out of threaded bore (337) (Block 310L of FIG. 14), thereby decoupling transducer assembly (12) from waveguide (336). After motor (350) has completely removed threaded stud (12E) from threaded bore (337) as shown in FIG. 15C, solenoid (360) drives locking member (362) downwardly from the second position into the first position such that locking member (362) disengages shaft assembly (330) as shown in FIG. 15D (Block 310M of FIG. 14).

It should be understood that motor (350) may be configured to rotate transducer assembly (12) only until transducer assembly (12) and waveguide (336) are disconnected. For instance, control module (367) may be configured to stop rotation of motor (350) and to actuate solenoid (360) to retract locking member (362), after a sensor senses a predetermined amount of back EMF of motor (350) indicating that transducer assembly (12) has been disconnected from waveguide (336). Additionally or alternatively, control module (367) may be configured to stop rotation of motor (350), and then actuate solenoid (360) to retract locking member (362), after a predetermined amount of angular travel of motor (350) or transducer assembly (12) is sensed by an encoder or other sensor. For instance, if one full rotation of motor (350) is required to connect waveguide (336) with transducer assembly (12), control module (367) may be configured to permit two full rotations of motor (350) to disconnect waveguide (336) with transducer assembly (12). Other suitable ways in which motor (350) may be automatically stopped and solenoid (360) may be automatically actuated will be apparent to those of ordinary skill in the art in view of the teachings herein.

With collar (339) now in the distal longitudinal position relative to body portion (338) and knob (340), and with shaft assembly (330) now disconnected from transducer assembly (12), the user may remove shaft assembly (330) from socket (324) of handle assembly (320) (Block 310N of FIG. 14). FIG. 15E shows shaft assembly (330) disengaged from socket (324) of handle assembly (320) and moved back to the first longitudinal position relative to handle assembly (320). Shaft assembly (330) may then be disposed of, reprocessed, replaced, and/or otherwise dealt with.

C. Exemplary Lateral Force Detecting Features

Shaft assemblies (230) described above are decoupled from their respective handle assemblies (220, 230) in response to longitudinally directed forces. In particular, shaft assembly (230) is decoupled from handle assembly (220) by pulling longitudinally distally on body portion (238) and knob (240); while shaft assembly (330) is decoupled from handle assembly (320) by pulling longitudinally distally on collar (339). In some versions of instruments (210, 310), it may be desirable to provide features that discriminate between longitudinally oriented forces on at least a portion of shaft assembly (230,330) and laterally oriented forces on at least a portion of shaft assembly (230, 330). As used herein, terms such as "laterally oriented forces" are not intended to be limited to forces that are oriented exactly perpendicularly to the longitudinal axis of shaft assembly (230, 330). Instead, terms such as "laterally oriented forces" are intended to include forces that have some lateral or transverse component, including forces that are oriented obliquely relative to the longitudinal axis of shaft assembly (230, 330). Furthermore, it may be desirable to provide features that prevent removal of shaft assemblies (230, 330) from handle assemblies (230, 320) in response to laterally oriented forces, thus ensuring that shaft assemblies (230, 330) are removed from handle assemblies (220, 320) only in response to longitudinally oriented forces on shaft assemblies (230, 330).

FIGS. 16-20 show an example of an instrument (410) that is configured to discriminate between longitudinally oriented forces on at least a portion of a shaft assembly (430) and laterally oriented forces on at least a portion of shaft assembly (430). Instrument (410) of the present example is configured to operate substantially similar to instruments (210, 310) discussed above except for the differences discussed below. In particular, instrument (410) is configured to mechanically secure shaft assembly (430) to a handle assembly (420) via a motor (450). Transducer assembly (12) of the present example is rotatably supported by a bushing (438), which is positioned within a housing (422) of handle assembly (420). Threaded stud (12E) of horn (12D) of transducer assembly (12) extends through a distal portion of housing (422) such that transducer assembly (12) may be connected with a waveguide (402) via threaded stud (12E). A flexible seal (432) is positioned about horn (12D) at the point where horn (12D) passes through housing (422). Flexible seal (432) allows horn (12D) to transfer stresses from shaft assembly (430) to transducer assembly (12).

Figure 17:
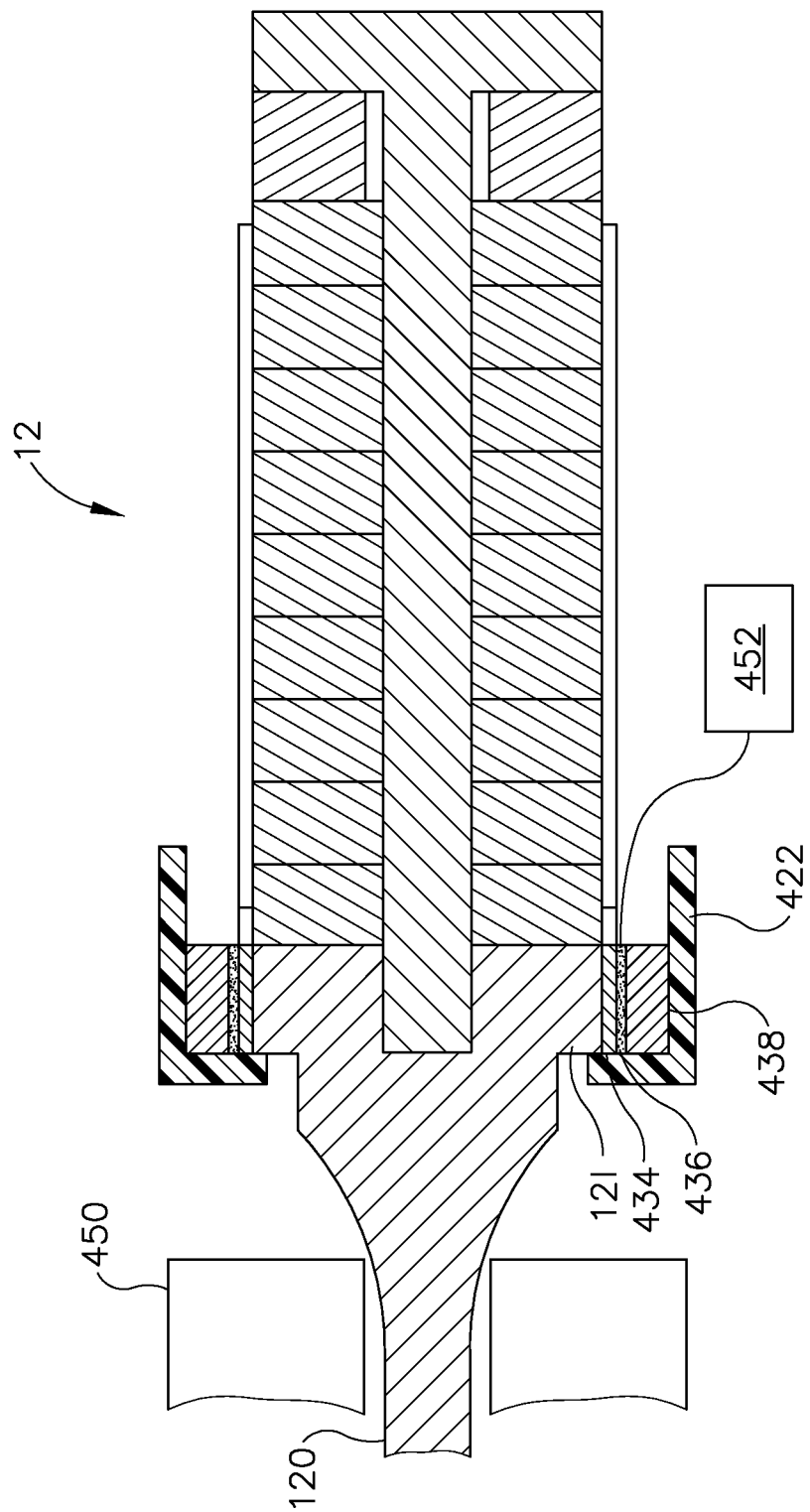
FIG. 17 depicts a detailed cross-sectional view of the instrument of FIG. 16.
Figure 18:
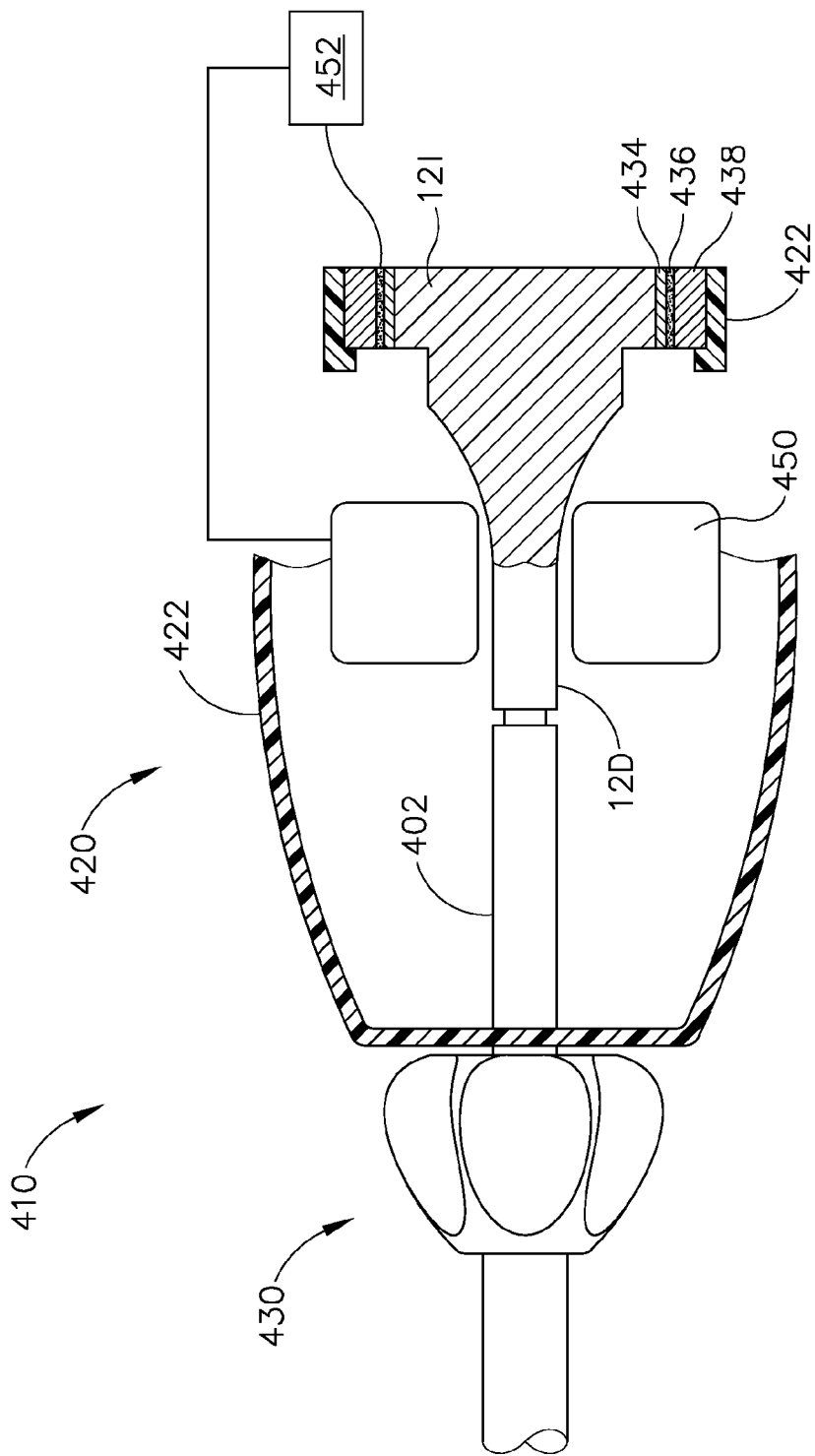
FIG. 18 depicts a top view of the instrument of FIG. 16.

As best seen in FIGS. 17-18, a lubricous layer (434) is disposed about an exterior surface of mounting flange (12I) of transducer assembly (12), within bushing (438). A sensing layer (436) is disposed about an exterior surface of lubricous layer (434), also within bushing (438). Sensing layer (436) is thus radially interposed between lubricous layer (434) and bushing (438). In some other versions, sensing layer (436) is radially interposed between lubricous layer (434) and mounting flange (12I). Sensing layer (436) may comprise a plurality of strain gauges, one or more NANOINK® sensors by NanoInk, Inc. of Skokie, Ill., one or more BEND SENSOR® sensors by Flexpoint Sensor Systems, Inc. of Draper, Utah, and/or any other suitable kind(s) of sensor(s). Various suitable kinds and numbers of sensors that may be used will be apparent to those of ordinary skill in the art in view of the teachings herein. Sensing layer (436) is in communication with a control module (452), which is operable to process signals from sensing layer (436). In some versions, control module (452) is further operable to selectively activate motor (450), based on signals from sensing layer (436) and/or based on other conditions. By way of example only, control module (452) may include a microprocessor, an ASIC, a printed circuit board, one or more features storing a control logic, and/or any other suitable components as will be apparent to those of ordinary skill in the art in view of the teachings herein.

Figure 19:
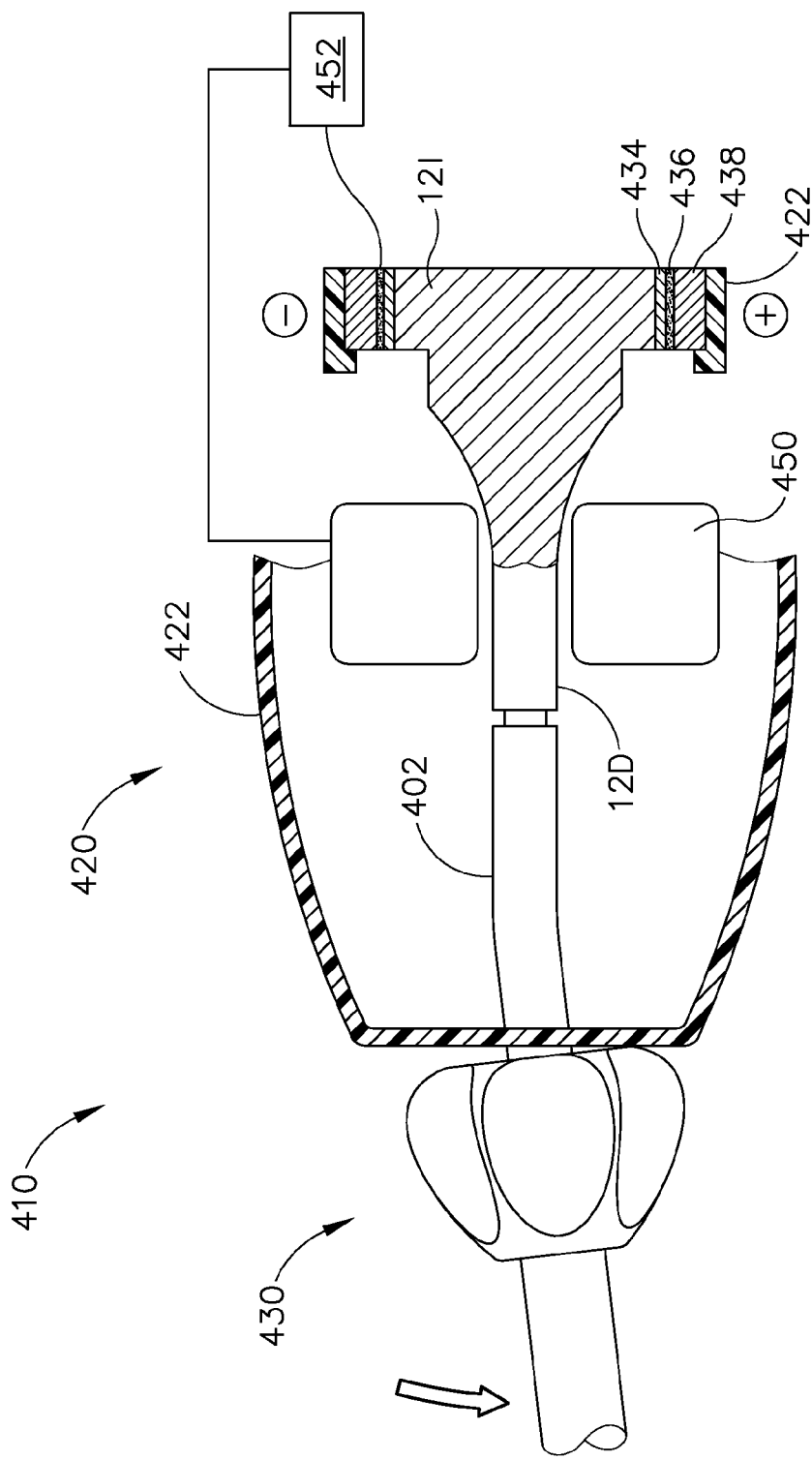
FIG. 19 depicts a top view of the instrument of FIG. 16 with a shaft assembly deflected by a lateral force.

In the present example, sensing layer (436) and control module (452) are together operable to sense non-longitudinal stresses in shaft assembly (430) and/or transducer assembly (12) as shown in FIG. 19. It should be noted that FIG. 18 shows shaft assembly (430) in a non-stressed state. It should also be noted that FIG. 19 depicts the stresses induced by laterally oriented forces as exaggerated lateral movement/deflection in shaft assembly (430) for the sake of clarity. In practice, sensing layer (436) and control module (452) may detect stresses induced by laterally oriented forces without any visible lateral movement/deflection actually occurring in shaft assembly (430). When sensing layer (436) and control module (452) detect stresses induced by laterally oriented forces, control module (452) may prevent shaft assembly (430) from being decoupled from handle assembly (420). For instance, control module (452) may be coupled with a mechanical lockout feature that selectively prevents shaft assembly (430) from being decoupled from handle assembly (420) when sensing layer (436) and control module (452) detect stresses induced by laterally oriented forces. As another merely illustrative example, control module (452) may selectively disable motor (450) when sensing layer (436) and control module (452) detect stresses induced by laterally oriented forces. Other suitable ways in which control module (452) may effectively prevent removal of shaft assembly (430) from handle assembly (420) when sensing layer (436) and control module (452) detect stresses induced by laterally oriented forces will be apparent to those of ordinary skill in the art in view of the teachings herein.

Figure 20:
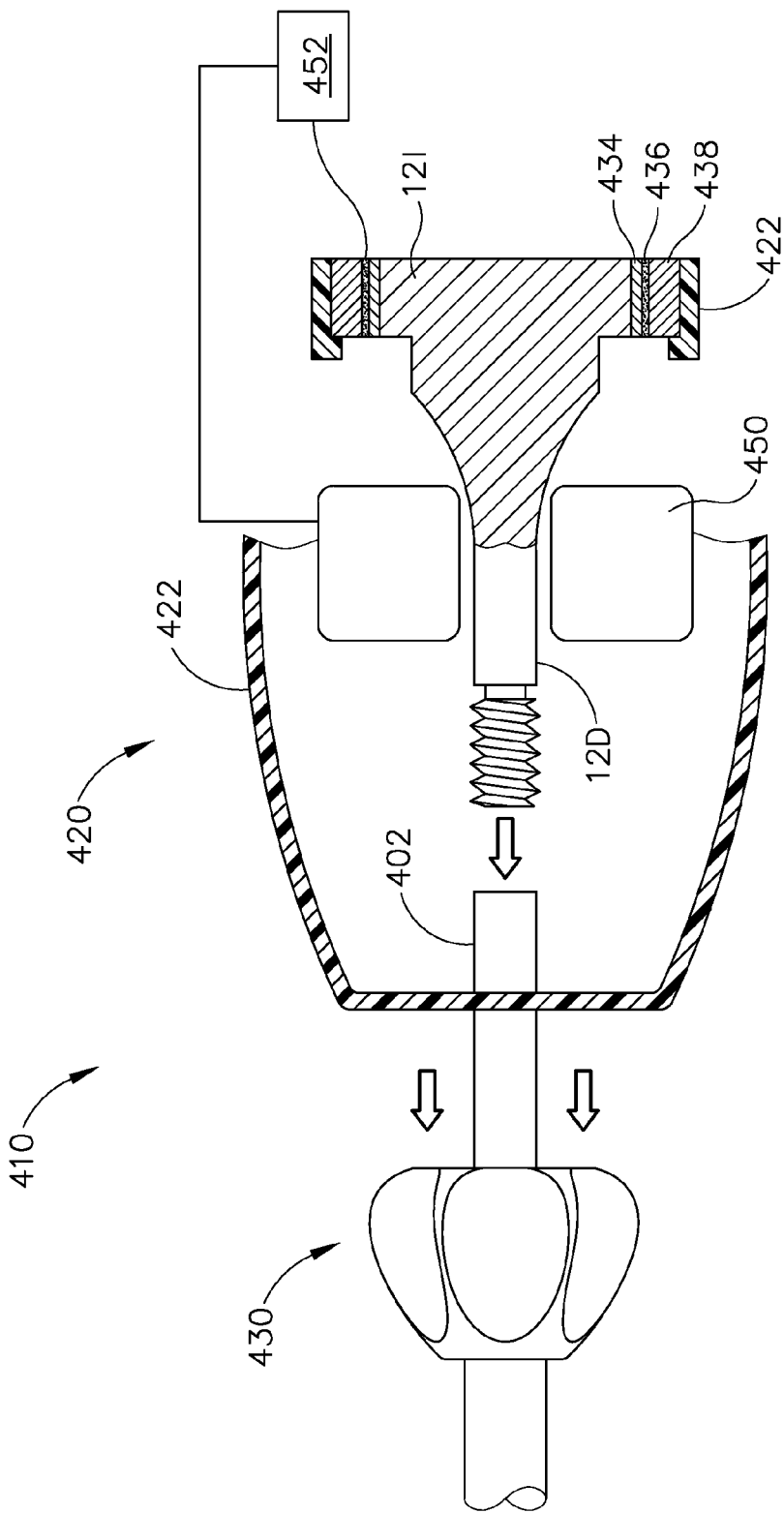
FIG. 20 depicts a top view of the instrument of FIG. 16 with the shaft assembly moved in a longitudinal direction.

As shown in FIG. 20, control module (452) allows shaft assembly (430) from handle assembly (420) when sensing layer (436) and control module (452) do not detect stresses induced by laterally oriented forces. In some versions, sensing layer (436) and control module (452) detect the presence of longitudinally oriented forces (e.g., longitudinally oriented forces that are substantially evenly distributed about the circumference of mounting flange (12I)). Control module (452) may thus activate motor (450) in response to the presence of longitudinally oriented forces. Alternatively, control module (452) may simply refrain from locking out removal of shaft assembly (430) from handle assembly (420) when sensing layer (436) and control module (452) detect the presence of longitudinally oriented forces. As yet another merely illustrative example, sensing layer (436) and control module (452) may be only sensitive to stresses induced by laterally oriented forces, such that sensing layer (436) does not detect longitudinally oriented forces.

Figure 25:
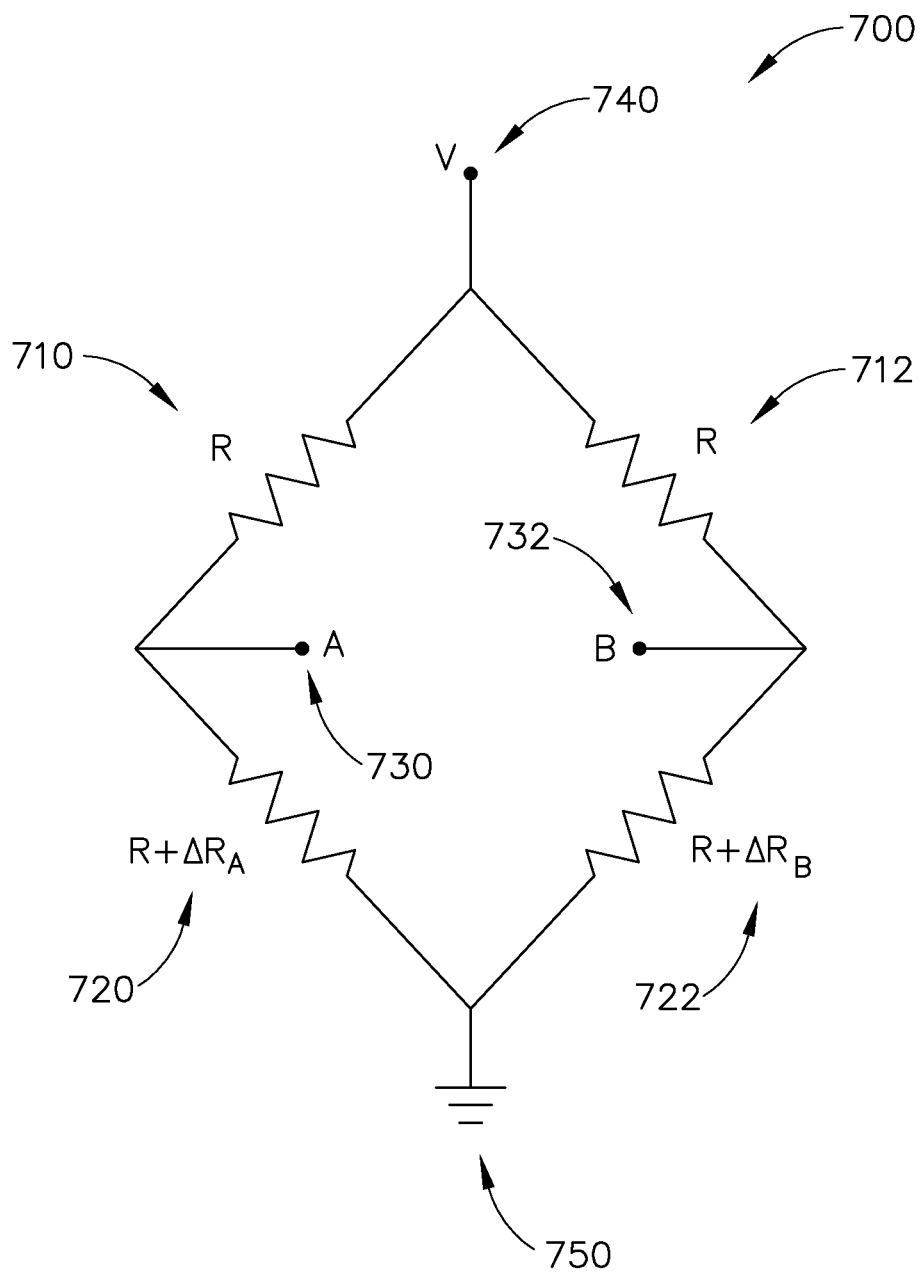
FIG. 25 depicts a schematic diagram of an exemplary bridge circuit that may be incorporated into the instrument of FIG. 20.

FIG. 25 shows an exemplary bridge circuit (700) that may be incorporated into instrument (410) to provide sensitivity to longitudinally oriented forces on at least a portion of a shaft assembly (430) and laterally oriented forces on at least a portion of shaft assembly (430). Circuit (700) of this example includes a pair of non-variable resistors (710, 712), a pair of variable resistors (720, 722), and a pair of outputs (730, 732). Circuit (700) further includes a power input (740) and a connection to ground (750). Non-variable resistors (710, 712) each have the same nominal resistance value (R) in the present example. By way of example only, non-variable resistors (710, 712) may each have a nominal resistance value (R) of approximately 120 ohms. Alternatively, any other suitable value may be used.

Variable resistor (720) has a resistance value $(R+\Delta R_A)$, where R is the same nominal value (R) noted above for non-variable resistors (710, 712) and $+\Delta R_A$ is an addend value. Variable resistor (722) has a resistance value $(R+\Delta R_B)$, where R is the same nominal value (R) noted above for non-variable resistors (710, 712) and $+\Delta R_B$ is an addend value. Variable resistors (720, 722) are provided by strain gauges in this example. For instance, such strain gauges may be provided in sensing layer (436) of instrument (410), on diametrically opposed lateral sides of the longitudinal axis of shaft assembly (430). These strain gauges may this provide variation in resistance based on laterally oriented stresses on shaft assembly (430).

In the present example, the addend value $(\Delta R_A)$ represents a resistance change caused by strain in the strain gauge that provides variable resistor (720). Thus, when the strain gauge that provides variable resistor (720) is under no strain, the addend value $(\Delta R_A)$ is zero. Variable resistor (720) thus provides a nominal resistance value (R) of 120 ohms when the strain gauge that provides variable resistor (720) is under no strain. Similarly, the addend value $(\Delta R_B)$ represents a resistance change caused by strain in the strain gauge that provides variable resistor (722). Thus, when the strain gauge that provides variable resistor (722) is under no strain, the addend value $(\Delta R_B)$ is zero. Variable resistor (722) thus provides a nominal resistance value (R) of 120 ohms when the strain gauge that provides variable resistor (722) is under no strain. In view of the foregoing, it should be understood that the resistance values $(R+\Delta R_A, R+\Delta R_B)$ of variable resistors (720, 722) are each 120 ohms either when shaft assembly (430) is not encountering any strain or when shaft assembly (430) is encountering strain that is only directed longitudinally.

A laterally oriented stress on shaft assembly (430) may provide diametrically opposing strains on the strain gauges that provide variable resistors (720, 722). In other words, the addend value $(\Delta R_B)$ may be the negative of the addend value $(\Delta R_A)$. In other words, the laterally oriented stress may provide an absolute addend value (AR), where $\Delta R=\Delta R_A$ and $\Delta R=-\Delta R_B$. Control module (452) may monitor the output voltage $(V_{AB})$ at outputs (730, 732), and selectively activate motor (450), or selectively enable activation of motor (450), based on the output voltage $(V_{AB})$ and/or based on other conditions. This output voltage $(V_{AB})$ will vary based on the absolute addend value (AR). In particular, $V_{AB}=\Delta R*V/R$, where $\Delta R$ is the absolute addend value, V is the voltage provided between power input (740) and ground (750), and R is the nominal resistance value (e.g., 120 ohms). It should be understood from the foregoing that the output voltage $(V_{AB})$ will be zero when the absolute addend value (AR) is zero. In other words, the output voltage $(V_{AB})$ will be zero when the strain gauges providing variable resistors (720, 722) are not picking up any lateral stress on shaft assembly (430). Control module (452) may thus only provide or enable activation of motor (450) when the output voltage ($V_{AB}$) is zero. Conversely, control module (452) may prevent activation of motor (450) when the output voltage ($V_{AB}$) is a non-zero value, which would indicate some lateral stress on shaft assembly (430).

Other suitable ways in which a strain sensing circuit may be constructed will be apparent to those of ordinary skill in the art in view of the teachings herein. Similarly, other suitable ways in which an instrument (410) may detect lateral forces on a shaft assembly (430) will be apparent to those of ordinary skill in the art in view of the teachings herein.

III. Exemplary Self-Guiding Stud

Figure 21:
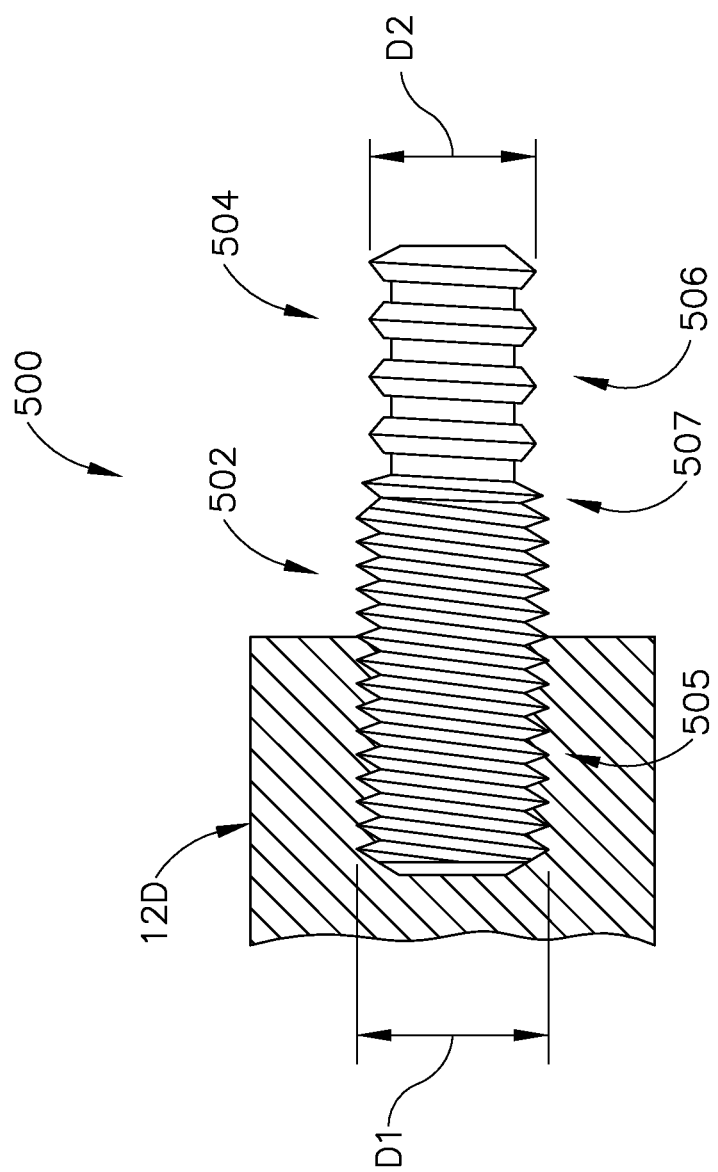
FIG. 21 depicts a side elevational view of an exemplary stud configured to couple the transducer of FIG. 5 with the transmission assembly of FIG. 7.

In some versions of transducer assembly (12) it may be desirable configured to provide improved self guidance into a threaded bore (104) of waveguide (102). FIG. 21 shows an example of such a self-guiding stud (500). A first portion (502) of stud (500) comprises threading (505). First portion (502) of stud (500) is threaded into a distal portion of horn (12D) of transducer assembly (12). A second portion (504) extends distally from the distal end of horn (12D). Second portion (504) comprises threading (506). Threading (505) defines an effective outer diameter (D1). Threading (506) defines an effective outer diameter (D2). Diameter (D1) is greater than diameter (D2). Threading (506) of second portion (504) gradually transitions into threading (505) of first portion (502) in a transition region (507) along a helical path about an exterior of stud (500). The helical path of this transition region (507) may extend along approximately 360° path, approximately 720°, or any other suitable angular range. It should be understood that increasing the angular range for the transition region (507) will make the transition more gradual.

Diameter (D2) is sized such that an appreciable amount of radial clearance exits between the distal end of stud (500) and an interior threading of threaded bore (104). Stud (500) may thus be more easily aligned within threaded bore (104) of waveguide (102). Furthermore, threading (506) may reduce the risk of cross-threading as stud (500) is threaded into threaded bore (104) of waveguide (102). As stud (500) is advanced into threaded bore (104), threading (506) may nevertheless mesh with the interior threading of threaded bore (104). In some instances, threading (505) is not exposed relative to the distal end of horn (12D), such that threading (506) is the only threading that meshes with the interior threading of threaded bore (104). In the present example, however, some length of threading (505) is exposed relative to the distal end of horn (12D). Thus, as stud (500) continues to advance into threaded bore (104), the portion of threading (505) that extends from horn (12D) may also eventually mesh with the interior threading of threaded bore (104). Transition region (507) may provide mechanical assistance to smoothly guide the interior threading of threaded bore (104) into engagement with threading (505). It should be understood that, in versions where a portion of threading (505) meshes with the interior threading of threaded bore (104), threading (506) need not necessarily also mesh with the interior threading of threaded bore (104). Other suitable configurations and relationships will be apparent to those of ordinary skill in the art in view of the teachings herein.

While self-guiding stud (500) is provided herein among other examples of where a waveguide (102) is coupled with a transducer assembly (12) via a motorized assembly, it should be understood that self-guiding stud (500) may also be used in versions where a waveguide (102) is coupled with a transducer assembly (12) manually. In other words, self-guiding stud (500) may be used in instruments where a waveguide (102) is coupled with a transducer assembly (12) manually, in a motorized fashion, or in any other suitable fashion.

IV. Exemplary Torque Sensing Features

Figure 22:
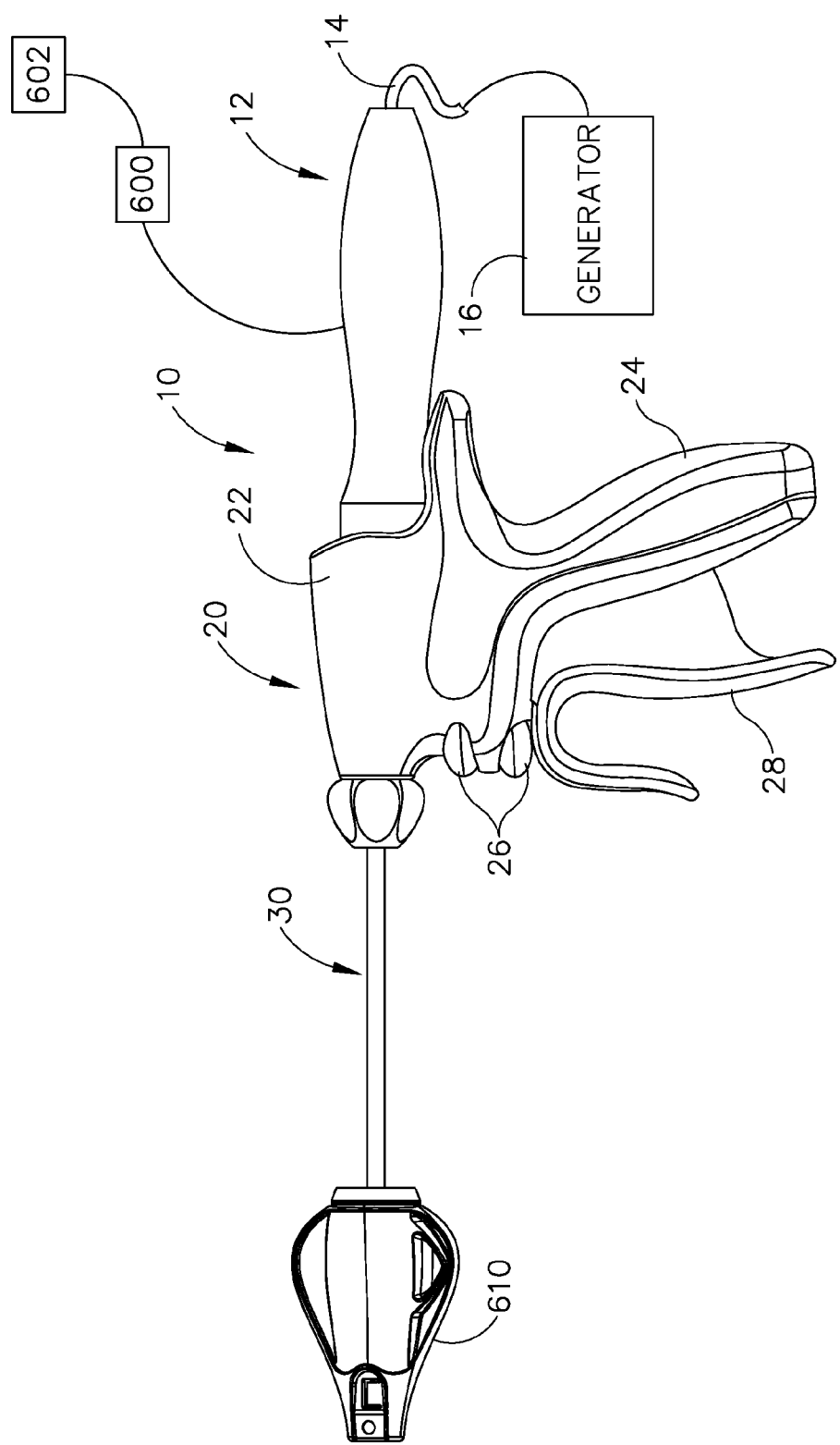
FIG. 22 depicts a schematic view of the instrument of FIG. 1 having a voltage detection feature.
Figure 23:
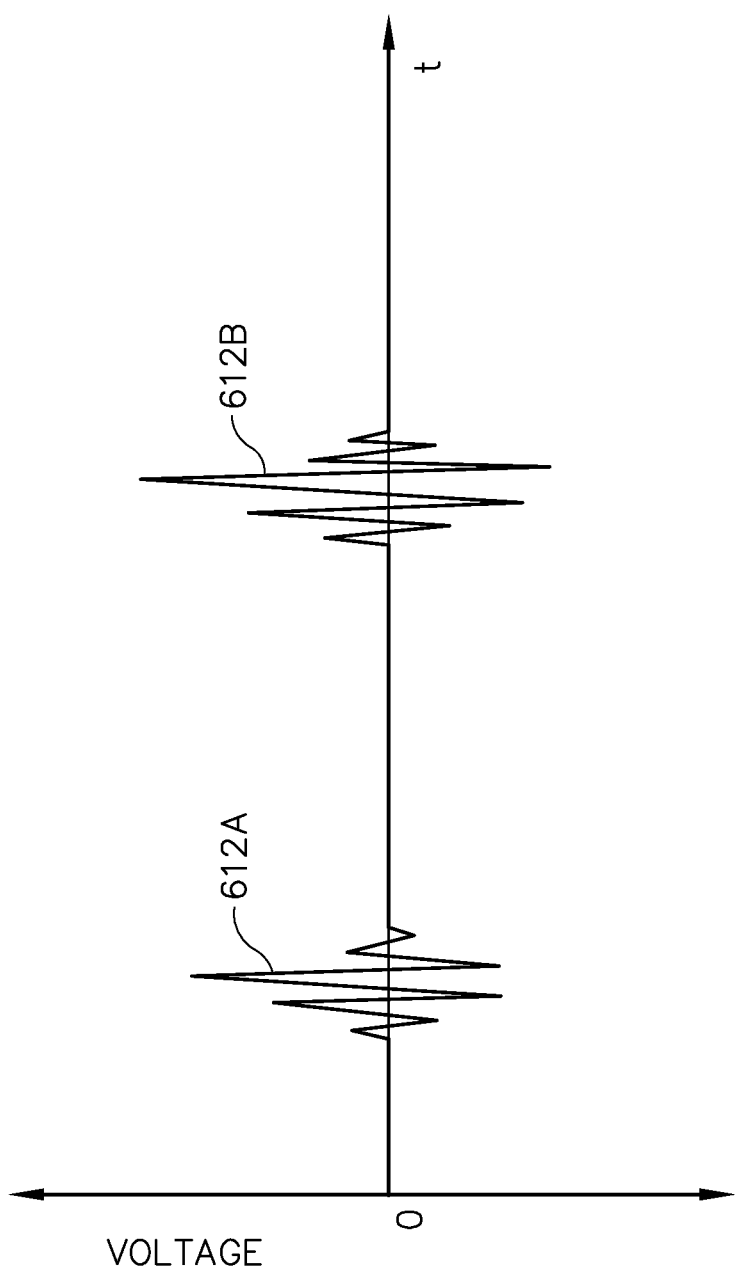
FIG. 23 depicts a chart showing voltage generated by piezoelectric elements of a transducer during assembly of the instrument of FIG. 1.
Figure 24:
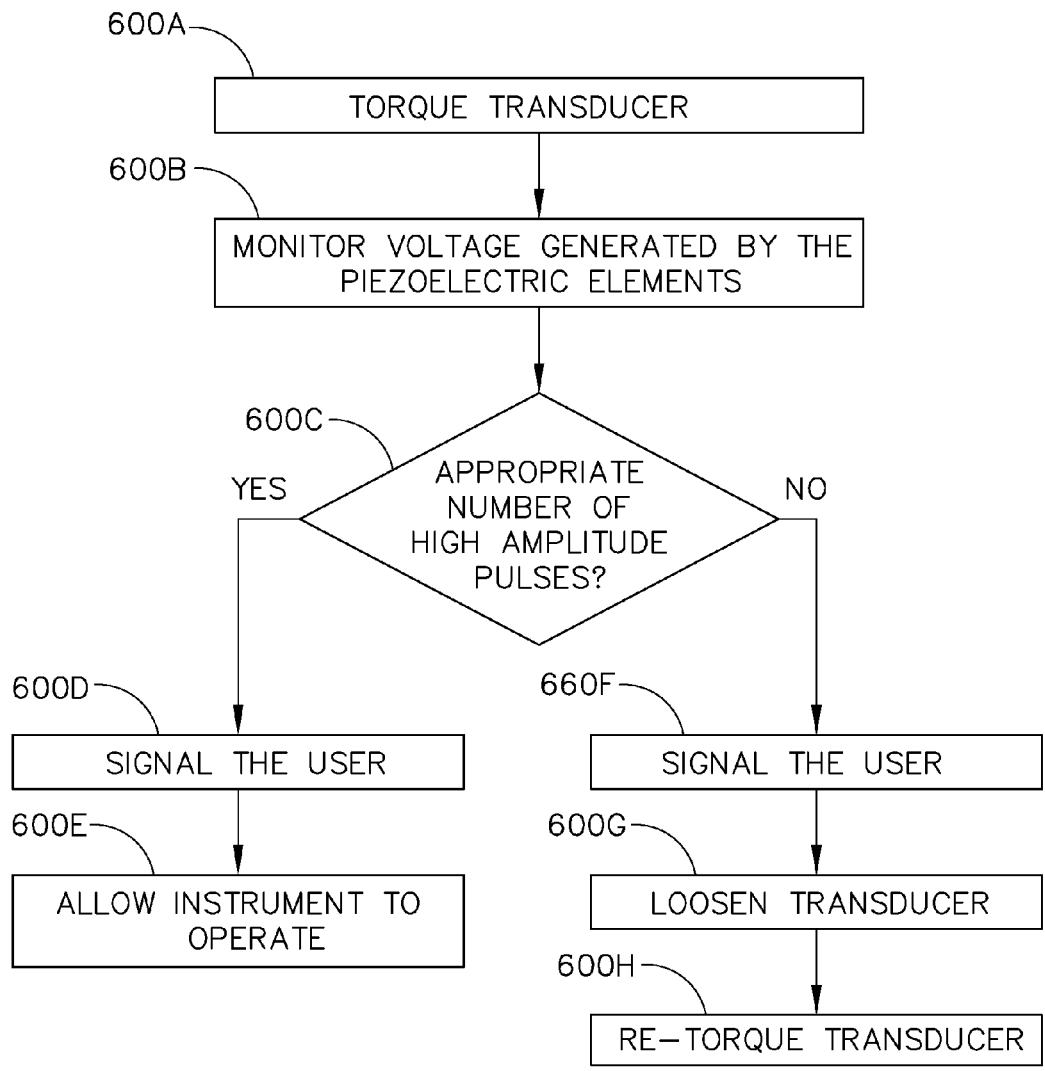
FIG. 24 depicts a flowchart showing steps of detecting and displaying appropriate coupling of a transducer to a waveguide.

In some versions of instrument (10), it may be desirable to provide a processing feature that signals to a user when an appropriate amount of torque has been applied to secure waveguide (102) to transducer assembly (12). FIGS. 22-24 show an example of such a processing feature (600), which is in communication with a user feedback device (602). In this example, a torque wrench (610) is used to manually secure waveguide (102) to transducer assembly (12). Torque wrench (610) is shown as being positioned over end effector (40), though it should be understood that a torque wrench may instead engage a portion of shaft assembly (30) (e.g., sliding down toward the proximal end of shaft assembly (30), etc.) and/or some other feature of instrument (10). Torque wrench (610) of the present example is configured to emit audible clicks as torque wrench (610) applies the appropriate amount of torque to secure waveguide (102) to transducer assembly (12). By way of example only, torque wrench (610) may be constructed and operable in accordance with at least some of the teachings of U.S. Pub. No. 2007/0191713, entitled "Ultrasonic Device for Cutting and Coagulating," published Aug. 16, 2007, now abandoned, the disclosure of which is incorporated by reference herein.

The features of torque wrench (610) that generate the audible clicks comprise snapping features that generate vibration pulses (e.g., one vibration pulse associated with each clicking sound). These vibration pulses generated by torque wrench (610) travel along waveguide (102) to piezoelectric stack (12J) of transducer assembly (12). Piezoelectric stack (12J) generates voltage pulses (612A, 612B) in response to the vibration pulses. Thus, each voltage pulse (612A, 612B) is associated with a respective click from torque wrench (610). As shown in FIG. 23, these voltage pulses (612A, 612B) comprise relatively high-amplitude short-duration pulses (612A, 612B). The peak-to-peak amplitude of each pulse (612A, 612B) of the present example is approximately 3 volts having a duration of approximately 20 milliseconds. A duration of approximately 400 milliseconds exists between a first pulse (612A) and a second pulse (612B) of the present example. Of course, these values are merely illustrative. Piezoelectric stack (12J) may instead generate pulses having various other kinds of parameters/characteristics in response to vibration pulses generated by torque wrench (610).

It should also be understood that the amplitude of pulses (612A, 612B) may be indicative of the amount of torque provided at the interface of waveguide (102) and transducer assembly (12). Thus, there may be variation in the amplitude of pulses (612A, 612B) as the operator actuates torque wrench (610). For instance, if the amplitude of the second pulse (612B) is greater than the amplitude of the first pulse (612A), this may indicate that torque wrench (610) has achieved greater torque between waveguide (102) and transducer assembly (12) on the second click. If the user continues to rotate torque wrench (610) relative to handle assembly (20) and transducer assembly (12), torque wrench (610) may continue to emit a series of clicks, while a corresponding series of pulses are generated by transducer assembly (12). The amplitude of these subsequent pulses may demonstrate a substantially consistent amplitude, which may indicate that the interface of waveguide (102) and transducer assembly (12) has reached the maximum, appropriate level of torque. In other words, the consistency in the amplitude of voltage pulses generated by transducer assembly (12) in response to clicks of torque wrench (610) may be indicative of the appropriate level of torque being achieved. In some instances, the amplitude of the voltage pulses may decrease within a series. Such a decrease in amplitude may be indicative of a cracked pin (33) and/or some other kind of mechanical fault within the acoustic drivetrain.

FIG. 24 shows an exemplary set of steps that processing feature (600) may proceed through to signal to a user that the waveguide has or has not been appropriately torqued. At the beginning of the process, the user torques waveguide (102) using torque wrench (610) to secure waveguide (102) to transducer assembly (12) (Block 600A). Processing feature (600) monitors the voltage generated by piezoelectric stack (12J) of transducer assembly (12) (Block 600B). If processing feature (600) detects the appropriate number of pulses (612A, 612B) generated by piezoelectric stack (12J) of transducer assembly (12) within a predetermined amount of time (Block 600C), processing feature (600) signals the user via a user feedback device (602) that waveguide (102) has been appropriately secured to transducer assembly (12) (Block 600D) and allows the user to operate instrument (10) (Block 600E).

If processing feature (600) does not detect the appropriate number of pulses (612A, 612B) generated by piezoelectric stack (12J) of transducer assembly (12) within the predetermined amount of time (Block 600C), processing feature (600) signals the user that waveguide (102) has not been appropriately secured to transducer (12) (Block 600F). If processing feature (600) does not detect the appropriate number of pulses (612A, 612B) generated by piezoelectric stack (12J) of transducer assembly (12) within the predetermined amount of time (Block 600C), processing feature (600) may further prevent transducer assembly (12) from being activated. At this point, the user must either continue torquing or loosen waveguide (102) (600G) from transducer assembly (12) and re-torque waveguide (12) (600H). Upon re-torquing waveguide (12), processing feature (600) will once again monitor the voltage generated by piezoelectric stack (12J) of transducer assembly (12) (Block 600B). Processing feature (600) may include noise filtering features configured to filter out voltage changes generated by vibrations/forces caused by things other than the clicking features of torque wrench (610).

While FIG. 22 depicts processing feature (600) and user feedback device (602) as being separate from handle assembly (20) and generator (16), it should be understood that processing feature (600) and/or user feedback device (602) may be integrated into handle assembly (20) and generator (16). It should further be understood that processing feature (600) and user feedback device (602) as may be incorporated into any of the instruments (10, 210, 310, 410) discussed above. Regardless of where or how it is incorporated, user feedback device (602) may provide user feedback in any suitable form or combination of forms, including but not limited to audible, visual, and/or haptic feedback. Various suitable ways in which user feedback device (602) may be implemented will be apparent to those of ordinary skill in the art in view of the teachings herein. Moreover, user feedback device (602) may simply be omitted if desired. For instance, processing feature (600) may just render generator (16), transducer assembly (12), and/or some other component(s)/feature(s) of instrument at least partially inoperable until processing feature (600) detects the appropriate number of pulses (612A, 612B) generated by piezoelectric stack (12J) within the predetermined amount of time.

In the process described above in relation to FIG. 24, processing feature (600) monitors for an appropriate number of pulses (612A, 612B) generated by piezoelectric stack (12J) of transducer assembly (12) within a predetermined amount of time (Block 600C). In addition to or as an alternative to monitoring the number of pulses (612A, 612B) generated by transducer assembly (12) within a predetermined amount of time, processing feature (600) may monitor the voltage amplitude of pulses (612A, 612B) generated by transducer assembly (12). For instance, processing feature (600) may detect whether two or more pulses (612A, 612B) in a series have a voltage amplitude that exceeds a predetermined threshold that is associated with an appropriate level of torque being achieved. Once processing feature (600) detects two or more pulses (612A, 612B) in a series having a voltage amplitude that exceeds the predetermined threshold, processing feature (600) may signal the user via a user feedback device (602) that waveguide (102) has been appropriately secured to transducer assembly (12) (Block 600D) and allow the user to operate instrument (10) (Block 600E).

In addition or in the alternative, processing feature (600) may monitor for consistency in the voltage amplitude of two or more pulses (612A, 612B) in a series. In some such versions, processing feature (600) first monitors for the voltage amplitude to exceed a predetermined threshold; and once processing feature (600) detects a first pulse (612A) having a voltage amplitude exceeding the predetermined threshold, processing feature (600) then monitors for consistency in voltage amplitude with respect to subsequent pulses (612B, etc.). In versions where processing feature (600) monitors for consistency in the voltage amplitude of two or more pulses (612A, 612B) in a series, processing feature (600) may trigger a response once processing feature (600) detects sufficient consistency in the voltage amplitude of two or more pulses (612A, 612B) in a series. Such a response may include signaling the user via a user feedback device (602) that waveguide (102) has been appropriately secured to transducer assembly (12) (Block 600D) and allowing the user to operate instrument (10) (Block 600E). In some versions, if processing feature (600) detects a drop in the voltage amplitude of two or more pulses (612A, 612B) in a series, processing feature (600) may alert the user of a fault condition. Other suitable ways in which processing feature (600) may process data relating to the voltage amplitude of two or more pulses (612A, 612B) in a series will be apparent to those of ordinary skill in the art in view of the teachings herein.

V. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for operating on tissue, the apparatus comprising:
   (a) a body assembly;
   (b) an ultrasonic transducer operable to convert electrical power into ultrasonic vibrations;
   (c) a shaft assembly extending distally from the body assembly, wherein the shaft assembly comprises a waveguide operable to transmit ultrasonic vibrations;
   (d) a motor operable to rotate the ultrasonic transducer to thereby selectively couple the ultrasonic transducer with the waveguide; and
   (e) an electrically powered locking feature disposed within the body assembly and configured to selectively prevent rotation of at least a portion of the shaft assembly relative to the body assembly by selectively moving within the body assembly and engaging the shaft assembly.

2. The apparatus of claim 1, wherein the locking feature comprises a solenoid configured to extend a locking member to thereby prevent rotation of at least a portion of the shaft assembly relative to the body assembly.

3. The apparatus of claim 1, wherein the body assembly comprises a sensor, wherein the sensor is configured to sense longitudinal positioning of the shaft assembly relative to the body assembly.

4. The apparatus of claim 3, wherein the sensor comprises a magnet.

5. The apparatus of claim 3, wherein the sensor is configured to activate the locking feature in response to proximal movement of the shaft assembly relative to the body assembly.

6. The apparatus of claim 3, wherein the sensor is configured to deactivate the locking feature in response to distal movement of the shaft assembly relative to the body assembly.

7. The apparatus of claim 1, wherein the shaft assembly comprises a longitudinally translatable member.

8. The apparatus of claim 7, wherein the translatable member is movable between a proximal longitudinal position and a distal longitudinal position.

9. The apparatus of claim 8, wherein the motor is configured to rotate the ultrasonic transducer as the translatable member is moved between the proximal longitudinal position and the distal longitudinal position.

10. The apparatus of claim 7, wherein the translatable member comprises a plurality of resilient arms configured to engage an interior surface of the shaft assembly.

11. The apparatus of claim 7, wherein the translatable member comprises at least one tab configured to engage an interior surface of the shaft assembly.

12. The apparatus of claim 11, wherein the interior surface of the shaft assembly defines a pair of annular recesses.

13. The apparatus of claim 12, wherein the at least one tab is configured to engage the pair of annular recesses.

14. The apparatus of claim 13, wherein the pair of annular recesses are configured to restrict translation of the translatable member.

15. The apparatus of claim 1, wherein the apparatus further comprises a stress sensing feature configured to sense laterally oriented forces within the shaft assembly.

16. The apparatus of claim 15, wherein the stress sensing feature is configured to prevent the shaft assembly from being detached from the body assembly in response to sensing non-longitudinal forces within the shaft assembly.

17. The apparatus of claim 1, wherein the shaft assembly is connected to the ultrasonic transducer by a threaded stud, wherein the threaded stud comprises a first threaded portion and a second threaded portion, wherein the first threaded portion defines a first effective outer diameter, wherein the second threaded portion defines a second effective outer diameter, wherein the first effective outer diameter is greater than the second effective outer diameter.

18. An apparatus for operating on tissue, the apparatus comprising:
(a) a body assembly;
(b) an ultrasonic transducer operable to convert electrical power into ultrasonic vibrations;
(c) a shaft assembly extending distally from the body assembly, wherein the shaft assembly comprises a waveguide operable to transmit ultrasonic vibrations;
(d) a motor operable to rotate the ultrasonic transducer to thereby selectively couple the ultrasonic transducer with the waveguide; and
(e) a locking feature configured to selectively linearly translate within the body assembly to thereby selectively prevent rotation of the shaft assembly relative to the body assembly.

19. An apparatus for operating on tissue, the apparatus comprising:
(a) a body assembly;
(b) a locking member, wherein the locking member is configured to translate within the body assembly through electrical power;
(c) an ultrasonic transducer operable to convert electrical power into ultrasonic vibrations;
(d) a shaft assembly extending distally from the body assembly, wherein the shaft assembly comprises a waveguide operable to transmit ultrasonic vibrations; and
(e) a motor operable to rotate the ultrasonic transducer to thereby selectively couple the ultrasonic transducer with the waveguide;
wherein the shaft assembly is configured to receive the locking member such that translation of the locking member within the body assembly prevents rotation of the shaft assembly relative to the body assembly.

20. The apparatus of claim 19, wherein the locking member comprises a solenoid.

* * * * *